United States Patent [19]

Wissner et al.

[11] Patent Number: 5,208,223
[45] Date of Patent: May 4, 1993

[54] PHOSPHOCHOLINE DERIVATIVE INHIBITORS OF PHOSPHOLIPASE $A_2$

[75] Inventors: Allan Wissner, Ardsley, N.Y.; Robert E. Schaub, Upper Saddle River, N.J.; Kenneth E. Green, Yorktown Heights; Philip R. Hamann, Garnerville, both of N.Y.

[73] Assignee: American Cyanamid Company, Stamford, Conn.

[21] Appl. No.: 865,395

[22] Filed: Jun. 3, 1992

Related U.S. Application Data

[62] Division of Ser. No. 612,745, Nov. 13, 1990, Pat. No. 5,144,045.

[51] Int. Cl.$^5$ .................. A61K 31/66; A61K 31/675; C07F 9/02; C07F 9/28
[52] U.S. Cl. .................................... 514/92; 514/77; 514/78; 514/109; 514/114; 548/119; 558/169
[58] Field of Search .................. 548/119; 558/169; 514/92, 114, 109

[56] References Cited

U.S. PATENT DOCUMENTS

| | | | |
|---|---|---|---|
| 4,640,913 | 2/1987 | Wissner | 514/77 |
| 4,697,031 | 9/1987 | Wissner | 558/169 |
| 4,699,990 | 10/1987 | Wissner | 558/169 |
| 4,703,130 | 10/1987 | Wissner | 558/169 |
| 4,762,942 | 8/1988 | Wissner | 514/77 |
| 4,883,816 | 11/1989 | Wissner | 558/169 |
| 4,894,367 | 1/1990 | Wissner | 514/78 |
| 4,900,731 | 2/1990 | Wissner et al. | 558/169 |
| 4,933,365 | 6/1990 | Marshall | 514/475 |
| 4,939,127 | 7/1990 | Wissner | 514/77 |
| 4,959,357 | 9/1990 | Reers | 514/103 |
| 4,962,096 | 10/1990 | Masaki | 514/92 |
| 5,144,045 | 9/1992 | Wissner et al. | 558/169 |

OTHER PUBLICATIONS

Flower, Biochem, Pharmac., 25, 285 (1976).
Lapetina, Annu. Rep. Med. Chem., 19, 213 (1984).
Dennis, The Enzymes, Academic Press, vol., 16, Chapter 9 (1983).
Wilkenson, AntiInflammatory Phospholipase $A_2$ Inhibitor Drugs to the Future, vol. 15, No. 2, p. 139-148 (1990).

Primary Examiner—Cecilia Tsang
Attorney, Agent, or Firm—Thomas S. Szatkowski

[57] ABSTRACT

Phospocholine derivatives having the formula:

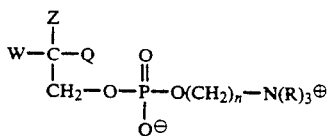

in which W, Z, Q and R are described in the specification are disclosed as useful for inhibiting the enzyme phospholipase $A_2$. Methods of making and using the compounds are also disclosed.

6 Claims, No Drawings

PHOSPHOCHOLINE DERIVATIVE INHIBITORS OF PHOSPHOLIPASE A$_2$

This is a divisional of co-pending application Ser. No. 07/612,745 filed on Nov. 13, 1990 now U.S. Pat. No. 5,144,045.

BACKGROUND OF THE INVENTION

1. Field of the Invention

The invention relates to novel phosphocholine derivatives which are inhibitors of the enzyme phospholipase A$_2$.

2. Description of the Prior Art

The enzyme phospholipase A$_2$ (phosphalide 2-acyl-hydrolase, PCA$_2$) is generally accepted as being the key enzyme responsible for exerting rate-determining regulatory control over the release of polyunsaturated fatty acids from phospholipids [Flower, R. Q., et al., Biochem. Pharmac., 25, 285 (1976); Lapetina, E. G., et al., Annu. Rep. Med. Chem., 19, 213 (1984)]. This enzyme has been isolated from many sources and is known to cleave snglycerophospholipids at the 2-position thus giving rise ultimately to the biosynthesis of platelet activating factor, prostaglandins, leukotrienes and prostacyclin [Dennis, E. A., The Enzymes; Academic Press: New York; Vol. 16, Chapter 9 (1983)]. The roles of these mediators in the inflammatory response associated with various diseases and physiological states is well known. Included among these diseases are asthma, arthritis, pancreatitis, myocardial ischemia, inflammation, pain, edema and their inflammatory related disorders.

Various compounds which are known to be inhibitors of phospholipase A$_2$ have been described in U.S. Pat. No. 4,959,357, 4,933,365 and in Wilkenson, Anti Inflammatory Phospholipase A$_2$ Inhibitors, Drugs of The Future, Vol. 15, No. 2, p 139-148 (1990). Various phosphocholine derivative compounds having anti hypertension activity have been disclosed in U.S. Pat. Nos. 4,640,913, 4,697,031, 4,699,990, 4,703,130, 4,939,127, 4,762,942, 4,883,816 and 4,894,367.

BRIEF SUMMARY OF THE INVENTION

The invention comprises novel phospholipase A$_2$ inhibiting compounds of the formula:

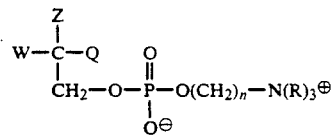

wherein:
- A) n is an integer from 2 to 6;
- B) R is selected from the group consisting of C$_1$-C$_4$ alkyl;
- C) Q is

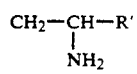

wherein R' is selected from the group consisting of C$_1$-C$_{24}$ alkyl, and W is a radical selected from the group consisting of hydrogen and hydroxyl and Z is CH$_2$—O—X wherein X is selected from the group consisting of C$_1$-C$_{24}$ alkyl;

D) Q is selected from the group consisting of

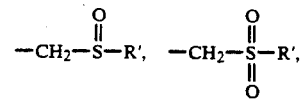

and -CH$_2$—S—R' wherein R' is selected from the group consisting of C$_1$-C$_{24}$ alkyl and W is a radical selected from the group consisting of hydrogen and hydroxyl and Z is selected from the group consisting of hydrogen and CH$_2$—OX wherein X is selected from the group consisting of C$_1$-C$_{24}$ alkyl;

E) Q is selected from the group consisting of:
(i)

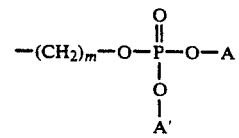

wherein m is O or 1, A and A' may or may not be the same but are each selected from the group consisting of C$_1$-C$_{24}$ alkyl, phenyl, C$_1$-C$_5$ alkoxy phenyl, C$_1$-C$_5$ alkyl phenyl, halogen substituted phenyl and triflouromethylphenyl;

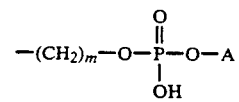

wherein M is O or 1, A is selected fron the group consisting of C$_1$-C$_{24}$ alkyl, phenyl, C$_1$-C$_5$ alkoxy phenyl, C$_1$-C$_5$ alkyl phenyl, halogen substituted phenyl and trifluoromethylphenyl;

(iii) —C≡C—R' wherein R' is selected from the group consisting of C$_1$-C$_{24}$ alkyl;

(iv)

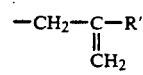

wherein R' is selected from the group consisting of C$_1$-C$_{24}$ alkyl;

(v) —CH$_2$—B(OH)$_2$
(vi) —CH$_2$—C≡CH$_2$
(vii)

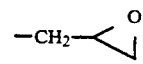

(viii)

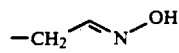

(ix)

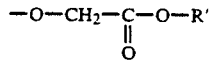

wherein R' is selected from the group consisting of $C_1-C_{24}$ alkyl;

(x)

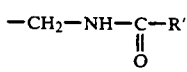

wherein R' is selected from the group consisting of $C_1-C_{24}$ alkyl;

(xi)

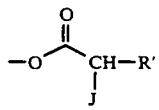

wherein R' is selected from the group consisting of $C_1-C_{24}$ alkyl and J is selected from the group consisting of chlorine, bromine, fluorine or hydrogen;

(xii)

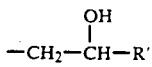

wherein R' is selected from the group consisting of $C_1-C_{24}$ alkyl;

(xiii)

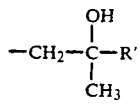

wherein R' is selected from the group consisting of $C_1-C_{24}$ alkyl;

(xiv)

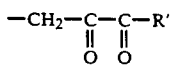

wherein R' is selected from the group consisting of $C_1-C_{24}$ alkyl;

and W is the radical hydrogen and Z is —CH$_2$—O—X wherein X is selected from the group consisting of $C_1-C_{24}$ alkyl;

F) W and Q are contained within a β-lactam ring:

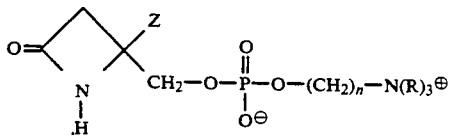

and Z is selected from the group consisting of $C_1-C_{24}$ alkyl,

G) W and Q are contained within an isoazaline ring:

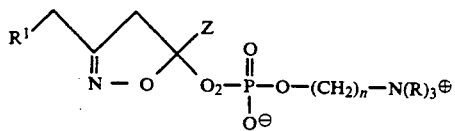

and Z is —CH$_2$—O—X wherein X and R' are selected from the group consisting of $C_1-C_{24}$ alkyl.

The invention also comprises novel methods of makeing the phospholipase A$_2$ inhibiting compounds described hereinabove.

The novel compounds described hereinabove have been proven to be specific inhibitors of the enzyme phospholipase A$_2$. These compounds are therefore useful for the treatment of any disease state or physiological disorder that results from the direct action of phospholipase A$_2$ or the mediators produced as a result of its activity. Consequently, use of these compounds for the treatment of pancreatitis, myocardial ischemia, inflammation, pain, edema, asthma, arthritis and any other disorder related to inflammation is indicated. The invention thus also comprises such methods of treatment.

DETAILED DESCRIPTION OF THE INVENTION

The preparation of the phospholipase A$_2$ inhibiting compounds according to the present invention is described hereinbelow in Flowcharts A through M wherein n, m, X, R', R', A, A' and J are as described hereinabove.

As indicated in the sequence of reactions outlined in Flowchart A, the alcohol 2 is reacted with acid 3 in the presence of an agent such as dicyclohexylcarbodiimide with a base such as N,N-dimethylaminopyridine in an inert solvent such as dichloromethane to produce ester 5. Alternatively, alcohol 2 can be reacted with anhydride 4 in the presence of a base such as sodium acetate in an inert solvent such as chloroform to produce ester 5.

Flowchart A

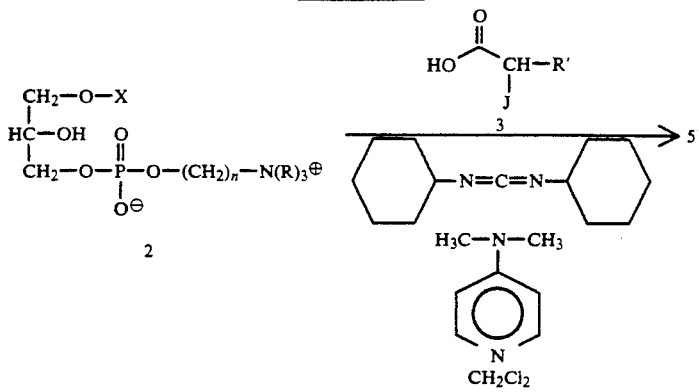

OR

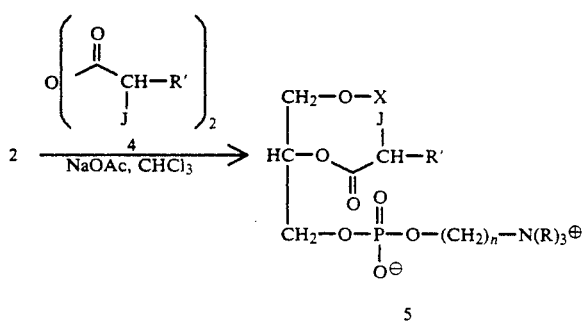

As indicated in the sequence of reactions outlined in Flowchart B, and α,β unsaturated ester like ethyl acrylate is reacted with thiol 7 in the presence of a base such as triethylamine in a solvent such as ethyl alcohol to produce the sulfide-ester 8. When 8 is reacted with a reducing agent such as lithium borohydride in a solvent such as tetrahydrofuran, the alcohol-sulfide 9 is produced.

Flowchart B

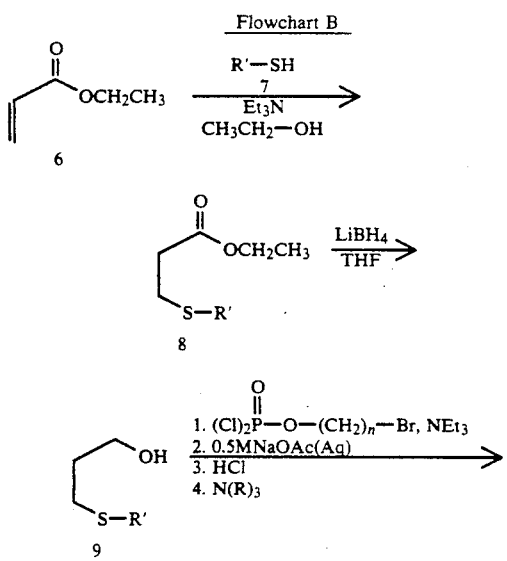

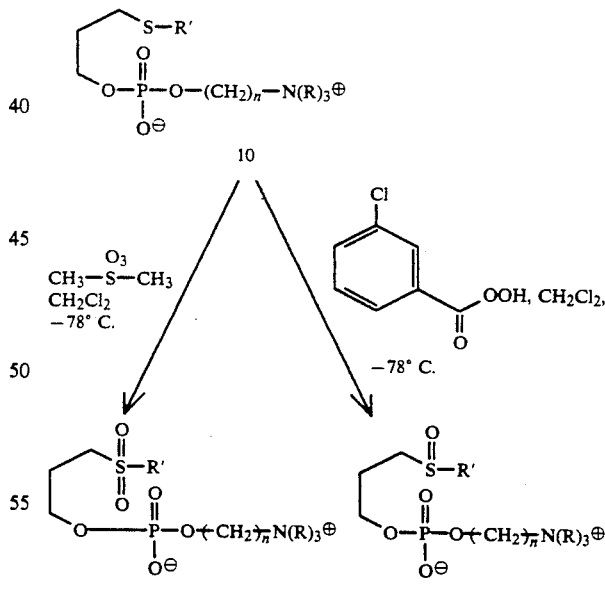

The alcohol-sulfide 9 is reacted with 2-bromoethyl phosphorodichlorodate in an inert solvent such as carbon tetrachloride in the presence of a base such as triethylamine. After approximately ten hours, the solvent is evaporated and a polar aprotic solvent such as tetrahydrofuran is added followed by an approximately equal volume of 0.5M sodium acetate. After approximately 10 hours, the solution is acidified with an acid such as hydrochloric acid and then extracted with an inert organic solvent such as ether. The residue which remains after evaporation of the organic solvent is dissolved in a solvent mixture such as chloroform, 2-propanol, dimethylformamide and trimethylamine is added to this mixture. After heating for approximately 5 hours at approximately 60° C., the phosphocholine derivative 10 is produced [Wissner, A., et al., J. Med. Chem., 27. 1174 (1984)]. When compound 10 is reacted with one equivalent of an oxidizing agent such as 3-chloroperoxybenzoic acid in an inert solvent such as dichloromethane at a reduced temperature of approximately −78° C., the sulfoxide 11 is produced. When the sulfide 10 is reacted with an excess amount of an oxidant such as ozone, wherein the intermediate ozonide must be reduced with a reductant such as dimethylsulfide, at a reduced temperature of approximately −78° C. in an inert solvent such as dichloromethane, the sulphone 12 is produced.

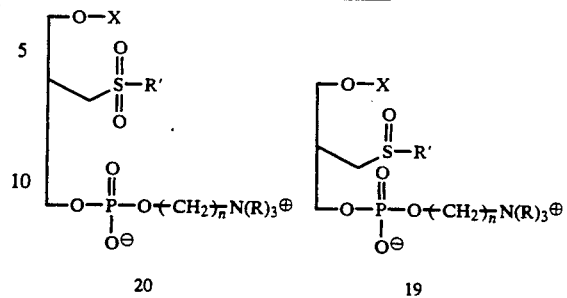

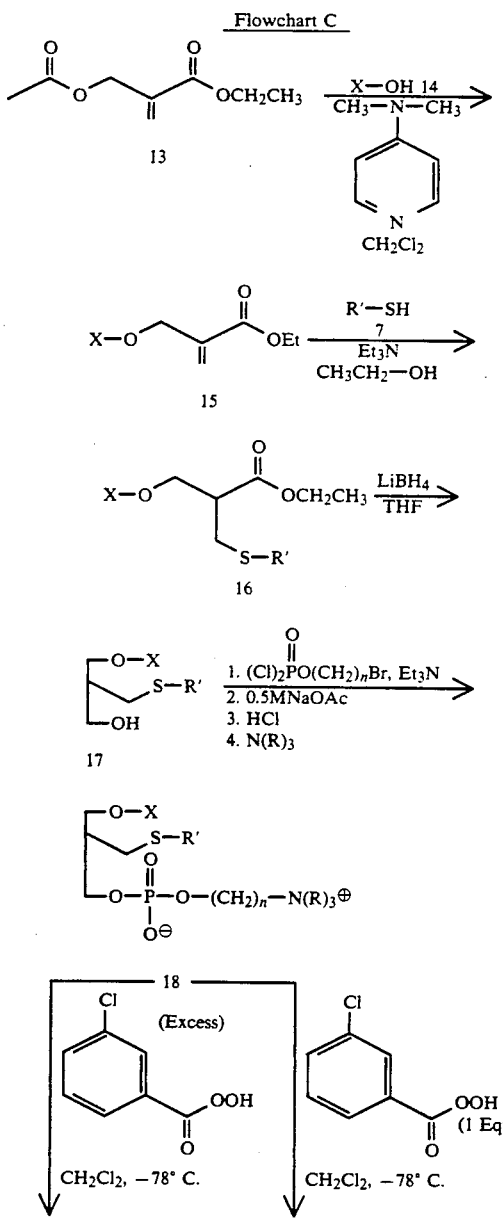

As indicated in the sequence of reactions outlined in Flowchart C, the functionalized ester 13 [previously described: J. Organometal. Chem. 308(3), $C_{27}$–$C_{32}$ (1986); Aust. J. Chem. 34(11), 2355 (1981); Pat. Specf. (Aust.) AU534112 B2, Jan. 5, 1984, 22 pp.] is reacted with alcohol 14 in the presence of a base such as N,N-dimethylaminopyridine in an inert solvent such as dichloromethane to produce 15. Compound 15 is reacted with thiol 7 in the presence of a base such as triethylamine in a solvent such as ethyl alcohol to produce 16. When compound 16 is reacted with a reducing agent such as lithium borohydride in a solvent such as tetrahydrofuran, alcohol 17 is produced. Following the sequence of reactions previously described in connection with Flowchart B, the alcohol 17 is converted to phosphocholine derivative 18. Reaction of sulfide 18 with one equivalent of an oxidizing agent such as 3-chloroperoxybenzoic acid in an inert solvent such as dichloromethane at a reduced temperature of approximately −78° C. produces sulfoxide 19. Reaction of sulfide 18 with an excess amount of an oxidizing agent such as 3-chloroperoxybenzoic acid in an inert solvent such as dichloromethane at a reduced temperature of approximately −78° C., produces sulphone 20.

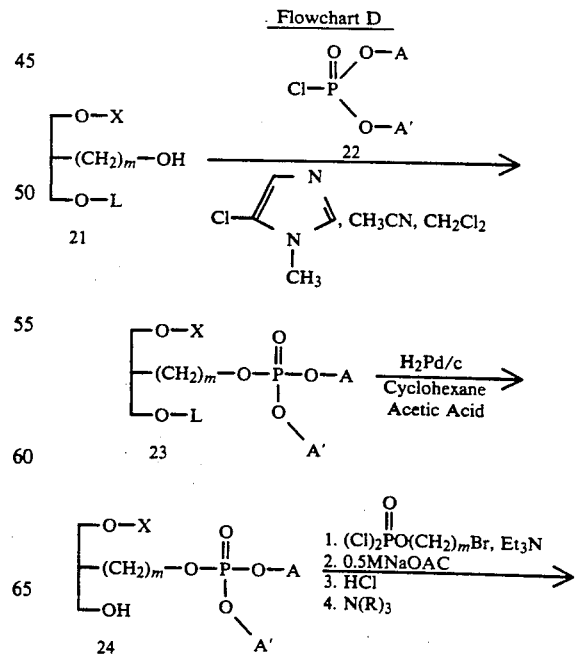

-continued
Flowchart D

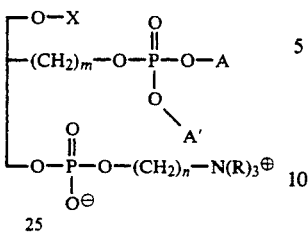
25

As indicated in the sequence of reactions outlined in Flowchart D, wherein L is selected from the group consisting of p-methoxytriphenylmethyl or benzyl, the alcohol 21 is reacted with phosphate 22 in the presence of a base such as N-methyl-5-chloroimidazole in a solvent system such as acetonitrile/dichloromethane to produce 23. Upon removal of the group L from 23 using, for example, hydrogenolytic conditions whereby compound 23 is placed under an atmosphere of hydrogen in the presence of a catalyst such as palladium on carbon in a solvent system such as cyclohexane/acetic acid; the alcohol 24 is produced. When 24 is subjected to the same set of reactions described hereinabove in connection with Flowchart B for attachment of a phosphocholine moiety, the phosphocholine derivative 25 is produced.

Alternatively, as indicated in the sequence of reactions outlined in Flowchart E the monomethyl derivative 29 may be prepared wherein X, A, L, m and n are as described hereinabove. This compound is useful for providing a route to the mono-acid 30.

Flowchart E

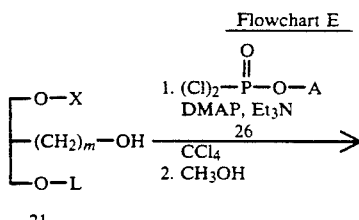
21

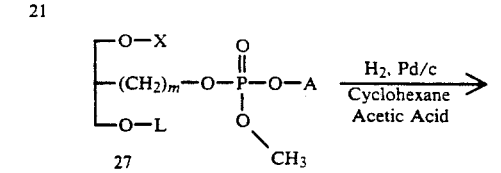
27

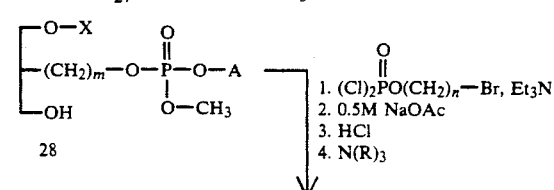
28

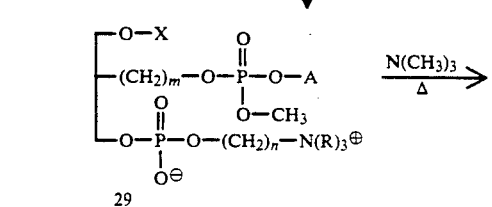
29

-continued
Flowchart E

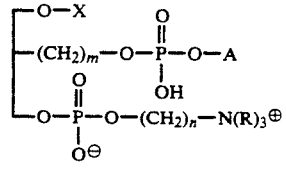
30

As indicated in the sequence of reactions outlined in Flowchart E, the alcohol 21 is reacted with dichlorophosphate 26 in the presence of a base such as dimethylaminopyridine and another base such as triethylamine in an inert solvent such as carbon tetrachloride. This mixture is then reacted with methyl alcohol to produce 27. Upon removal of the group L using, for example, hydrogenolytic conditions whereby compound 27 is placed under an atmosphere of hydrogen in the presence of a catalyst such as palladium on carbon in a solvent system such as cyclohexane, acetic acid, the alcohol 28 is produced. When 28 is subjected to the sequence of reactions described hereinabove in connection with Flowchart B for attachment of a phosphocholine moiety, compound 29 is produced. Reaction of 29 with an excess amount of trimethylamine at an elevated temperature produces 30.

Referring to Flowchart F, X is as described hereinabove as $C_1$-$C_{24}$ alkyl and Y is a leaving group selected from the group consisting of chlorine, bromine, iodo, $OSO_2CH_3$, and $OSO_2$-4-methylphenyl.

Flowchart F

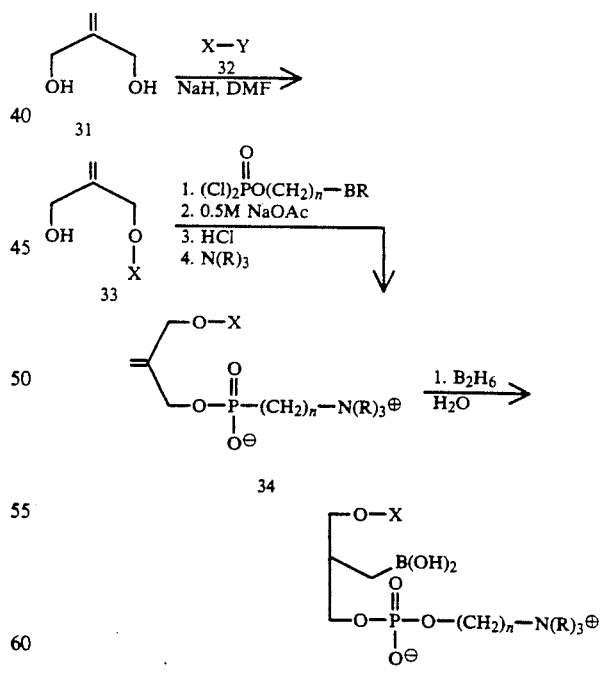

As indicated in the sequence of reactions outlined in Flowchart F, the alcohol 31 [Corey, E. J., et al., Tett. Lett., 3775 (1975)] is reacted with X-Y 32 wherein X is $C_1$-$C_{24}$ alkyl and Y is a leaving group selected from the group consisting of chlorine, bromine, iodo, $OSO_2CH_2$ and OSO$_2$-4-methylphenyl in a solvent such as dimethylformamide in the presence of a base such as sodiumhydride to produce 33. Alcohol 33 is subjected to the same sequence of reactions described hereinabove in connection with Flowchart B for attachment of a phosphocholine moiety to produce 34. When the olefinic moiety of 34 is reacted with an oxidant such as diborane wherein the intermediate borohydride is hydroolyzed with water, boronic acid 35 is produced.

presence of a base such as sodium carbonate in a solvent system such as ethyl alcohol-water produces 42.

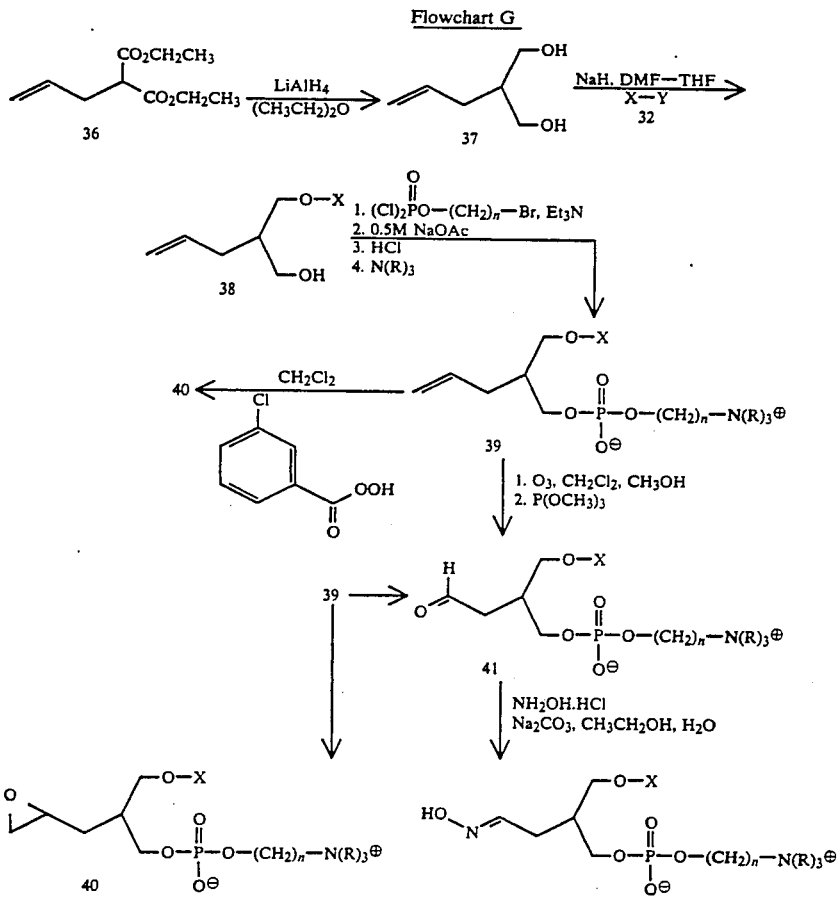

As indicated in the sequence of reactions outlined in Flowchart G, the malonate derivative 36 is reacted with a reductant such as lithium aluminum hydride in a solvent such as diethyl ether to produce the diol 37. When 37 is reacted with X-Y 32 in the presence of a base such as sodium hydride in a solvent mixture such as dimethylformamide (DMF)-tetrahydrofuran (THF), alcohol 38 is produced. When 38 is subjected to the sequence of reactions which have been previously outlined hereinabove in connection with Flowchart B for attachment of a phosphocholine group, 39 is produced. Reaction of 39 with an oxidant such as m-chloroperoxybenzoic acid in an inert solvent such as dichloromethane produces epoxide 40; whereas reaction of 39 with an oxidant such as ozone in a solvent system such as methyl alcohol-dichloromethane and subsequent reduction of the intermediate ozonide, inherent to such as oxidant, with a reductant such as trimethylphosphite produces 41. Reaction of 41 with hydroxylamine hydrochloride in the

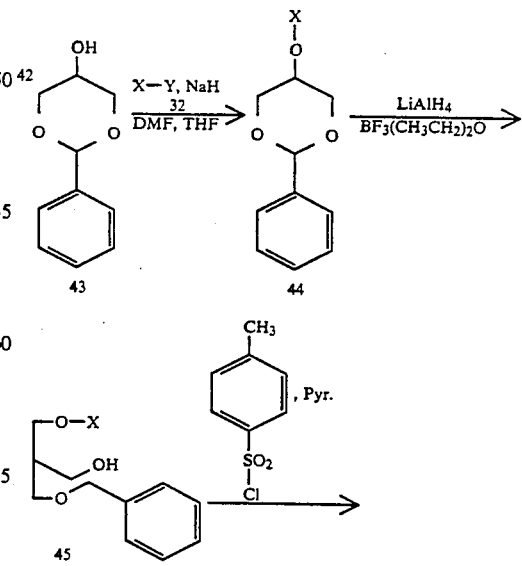

-continued
Flowchart H

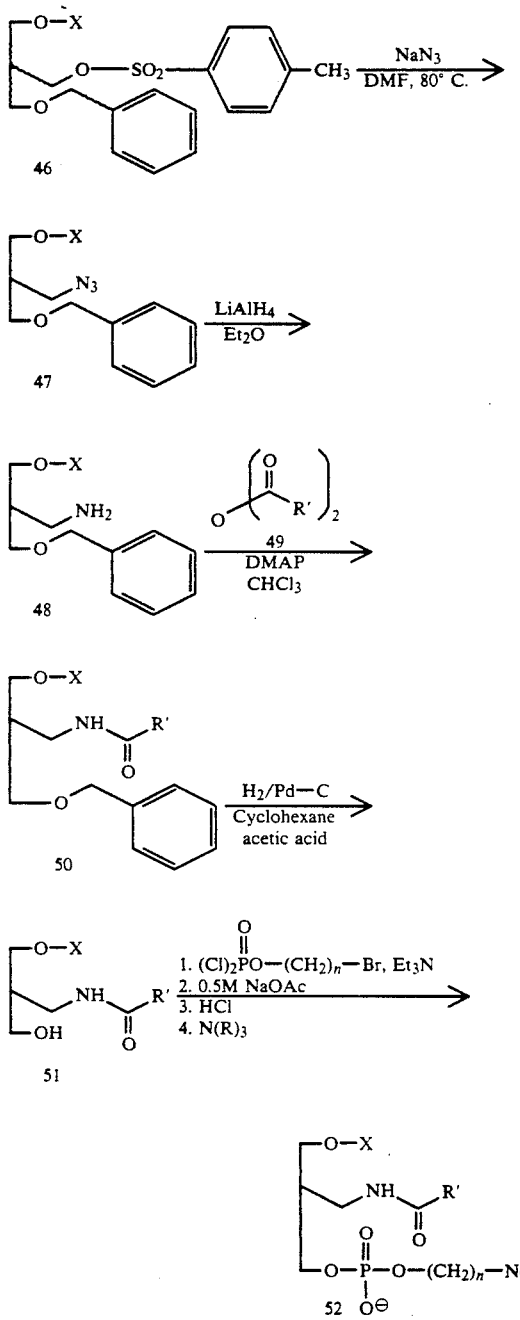

As indicated in the sequence of reactions in Flowchart H, alcohol 43 is reacted with X-Y 32 in the presence of a base such as sodium hydride and in a solvent system such as dimethylformamide (DMF)-tetrahydrofuran (THF) to produce 44. Acetal 44 is converted to an alcohol via reaction with a reductant such as lithium aluminum hydride boron trifluoride etherate to produce 45. The hydroxyl group of 45 is functionalized to become a leaving group with an agent such as p-toluenesulfonylchloride in the presence of a base such as pyridine to produce 46. When 46 is reacted with sodium azide in a solvent such as dimethylformamide (DMF), the azide derivative 47 is formed. Reduction of the azide group of 47 with a reductant such as lithium aluminum hydride in a solvent such as diethylether produces the amine 48. Reaction of 48 with anhydride 49 in the presence of a base such as dimethylaminopyridine in an inert solvent such as chloroform produces 50. Removal of the benzyl group via reduction using, for example, hydrogen and palladium on carbon in a solvent system such as cyclohexane-acetic acid, produces 51. When 51 is subjected to the sequence of reactions described hereinabove in connection with Flowchart B for attachment of a phosphocholine moiety, 52 is produced.

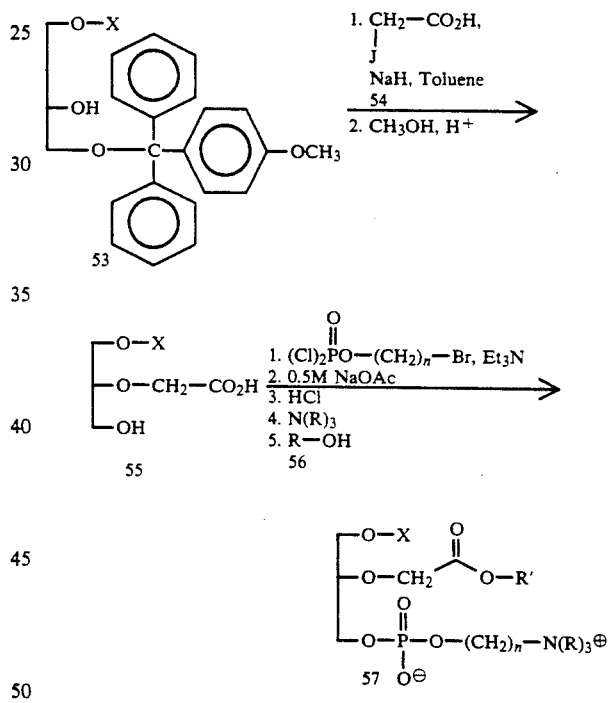

As indicated in the sequence of reactions in Flowchart I, alcohol 53 is reacted with acid 54 in the presence of a base such as sodium hydride in an inert solvent such as toluene. This reaction mixture is then hydrolyzed with an acidic methanol solution to produce 55. When 55 is subjected to the sequence of reactions previously described hereinabove in connection with Flowchart B for attachment of a phosphocholine moiety and this reaction mixture is treated with compound 56 (R'—OH wherein R' is selected from the group consisting of $C_1$-$C_{24}$ alkyl), the ester 57 is produced.

Referring to Flowchart J, R', X and Y are as described hereinabove and M is selected from the group consisting of alkyl $C_1$-$C_5$.

Flowchart J
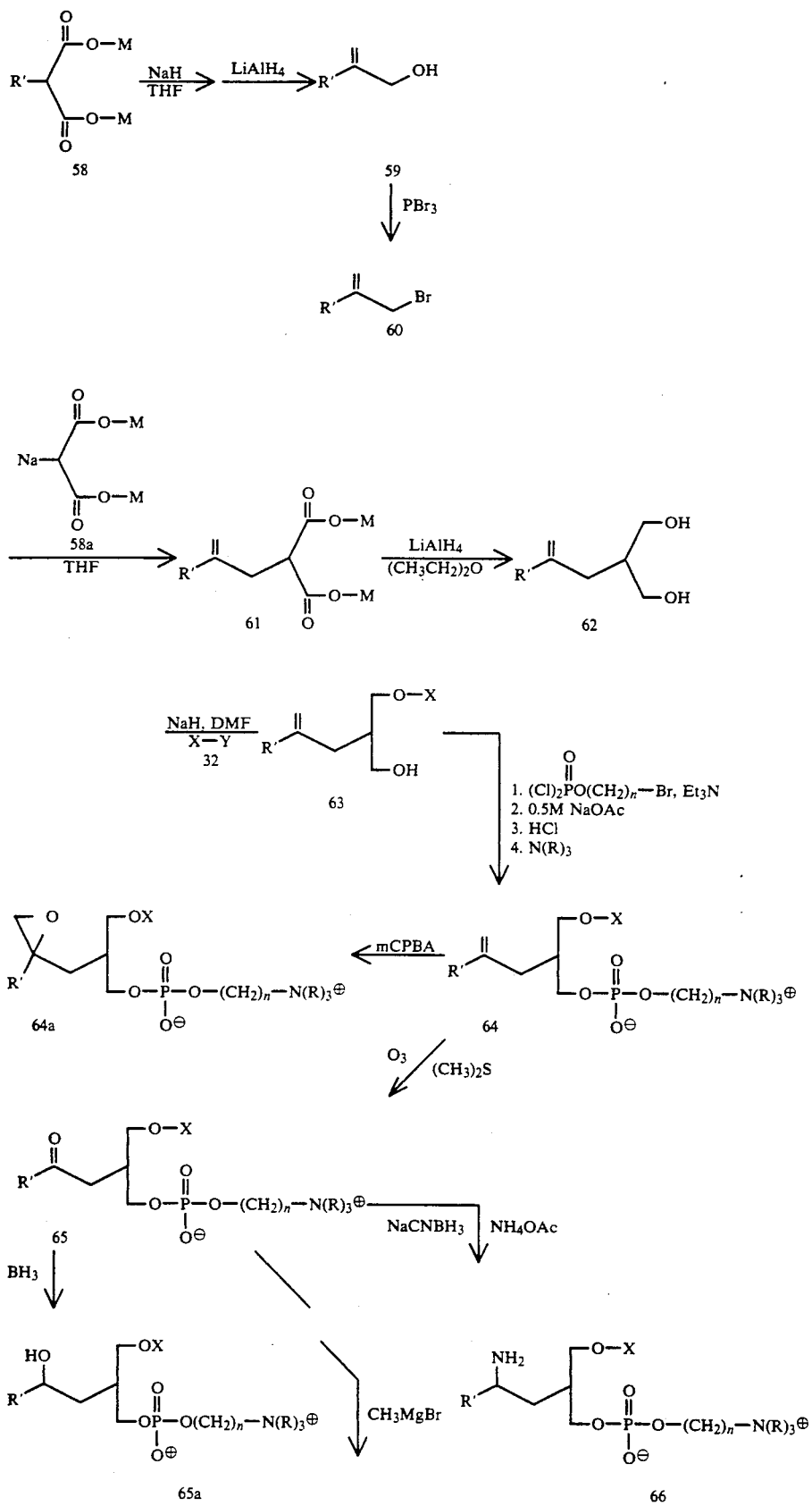

-continued
Flowchart J

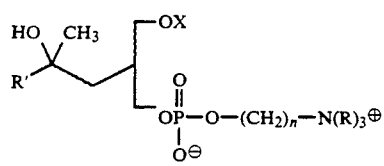

65b

As indicated in the sequence of reactions in Flowchart J, malonate derivative 58 is reacted With a base such as sodium hydride in an inert solvent such as tetrahydrofuran (THF). This reaction mixture is then reacted with a reductant such as lithium aluminum hydride to produce 59. The hydroxyl group of 59 is converted to a leaving group such as bromide via reaction with an agent such as phosphorous tribromide to produce 60. When 60 is reacted with a salt of 58 such as the sodium salt 58a in a solvent such as tetrahydrofuran (THF), 61 is produced. Reaction of 61 with a reductant such as lithium aluminum hydride in an inert solvent such as diethylether, produces diol 62. Deprotection of 62 with a base such as sodium hydride in a solvent such as dimethylformamide with X-Y 32 being present, produces 63. When alcohol 63 is subjected to the sequence of reactions previously described hereinabove in connection with Flowchart B for transformation of a hydroxyl group to a phosphocholine, 64 is produced. Reaction of 64 with an oxidant such as ozone wherein the intermediate ozonide is reduced with dimethylsulfide produces ketone 65 or by reaction with m-chloroperbenzoic acid gives epoxide 64a. When 65 is subjected to reductive amination conditions such as ammonium acetate sodium cyanoborohydride, the amine 66 is produced. When 65 is treated with borane, alcohol 65a is formed. Treatment of 65 with methylmagnesium bromide affords alcohol 65b.

Referring to Flowchart K, R', X, Y and M are as described hereinabove.

Flowchart K

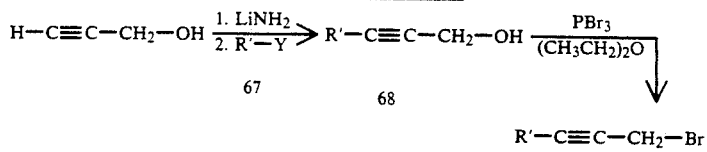

67      68

R'—C≡C—CH₂—Br

69

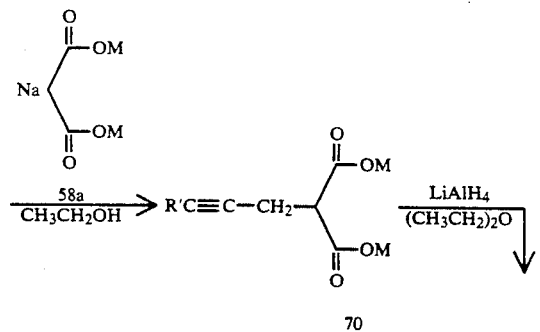

70

R'—C≡C—CH₂⟨OH, OH⟩

71

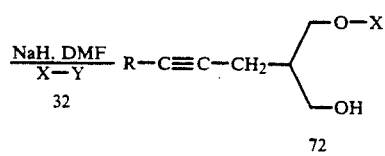

72

Flowchart K

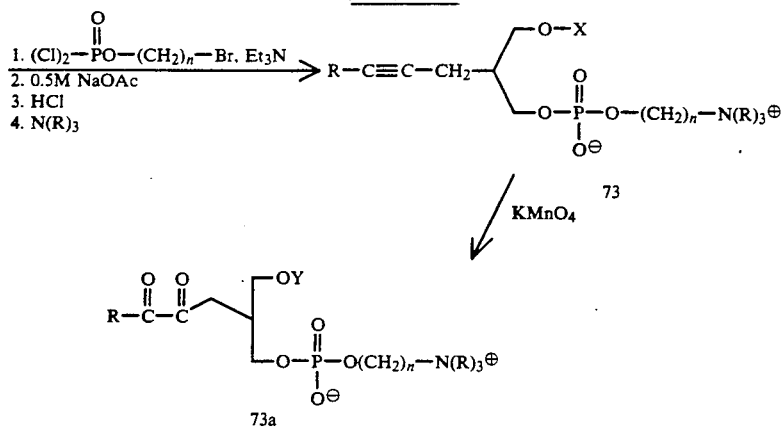

As indicated in the sequence of reactions outlined in Flowchart K, propargyl alcohol is reacted with a base such as lithium amide and then with R'-Y 67 to produce 68. The hydroxyl moiety of 68 is transformed to a leaving group such as bromide via the action of a reagent such as phosphorous tribromide in an inert solvent such as diethylether to give 69. Reaction of the propargylic bromide derivative 69 with 58a in a solvent such as ethyl alcohol produces 70. Reduction of the carboxylate groups of 70 with a reductant such as lithium aluminum hydride in an inert solvent such as diethylether produces 71. When 71 is treated with a base such as sodium hydride in a solvent such as dimethylformamide (DMF) and then reacted with X-Y 32, compound 72 is produced. Subjection of the alcohol 72 to the sequence of reactions previously described in connection with Flowchart B for transformation of an alcohol moiety to a phosphocholine moiety prduces 73. Reaction of 73 with potassium permanganate affords dione 73a.

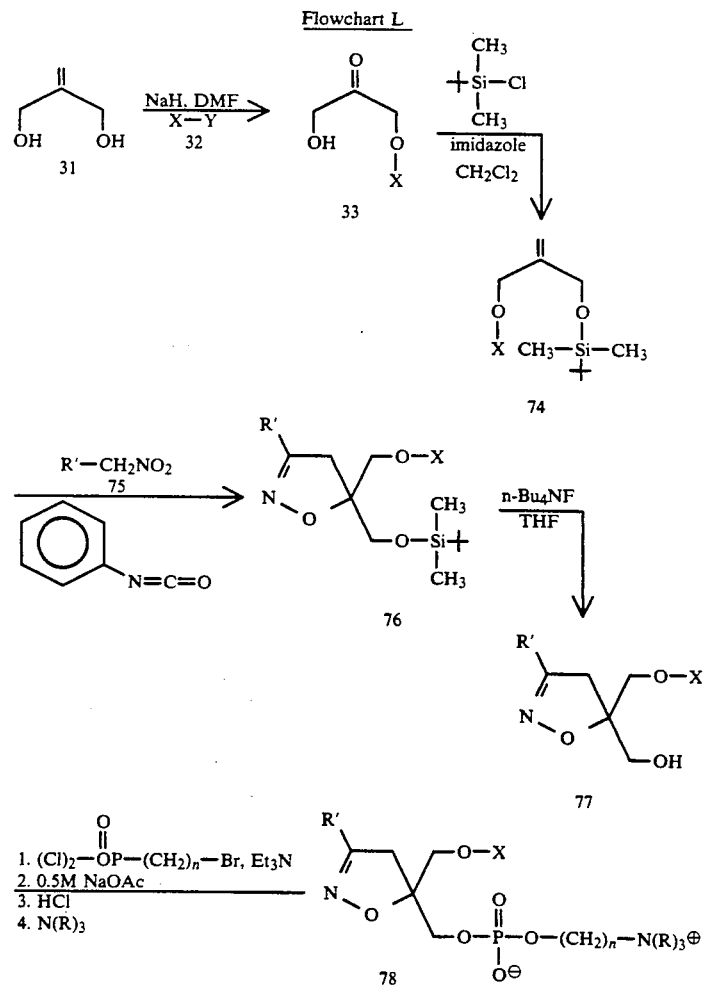

Flowchart L

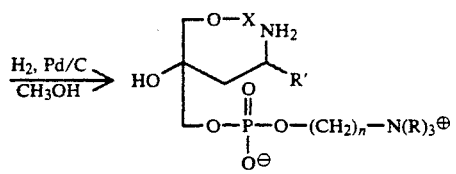

79

As indicated in sequence of reactions outlined in Flowchart L, the diol 31 [Corey, E. J., et al, Tett. Lett., 3775 (1975)] is reacted with a base such as sodium hydride in a solvent such as dimethylformamide in the presence of X-Y 32 to produce 33. Protection of the hydroxyl group of 33 with a moiety such as t-butyldimethylsilyl is accomplished by reaction of 33 with t-butyldimethylsilylchloride in a solvent such as dichloromethane in the presence of a base such as imidazole to produce 74. Compound 74 is reacted with a nitrile oxide which can be generated, for example, from nitro compound 75 and a dehydrating agent such as phenyl isocyanate to produce 76. Removal of the t-butyldimethylsilyl protecting group with a fluoride source such as tetra-n-butyl-ammonium fluoride in a solvent such as tetrahydrofuran (THF) produces 77. When 77 is subjected to the sequence of reactions previously described in connection with Flowchart B for attachment of a phosphocholine group, the phosphocholine derivative 78 is formed. Reduction of the isoxazoline ring using a catalyst such as palladium on carbon under an atmosphere of hydrogen in a solvent such as methanol produces 79.

Flowchart M

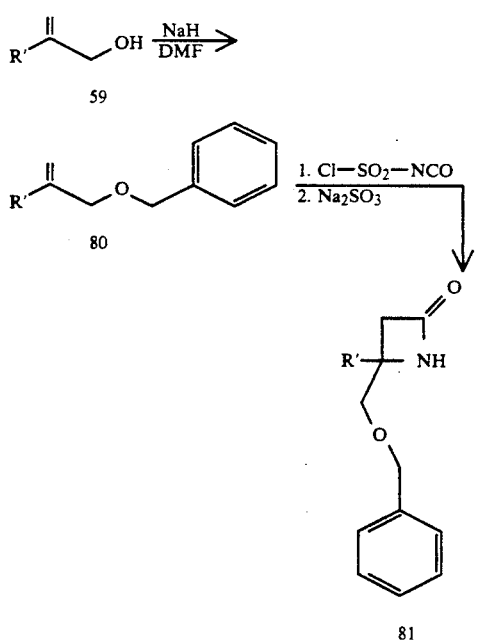

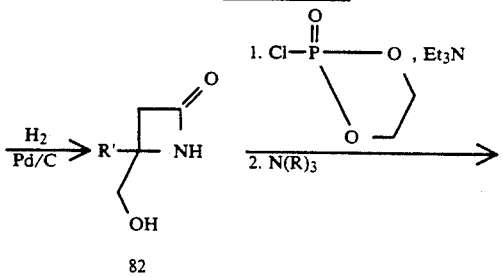

As indicated in the sequence of reactions outlined in Flowchart M, the alcohol 59 is reacted with a base such as sodium hydride in a solvent such as dimethylformamide (DMF) in the presence of benzyl bromide to produce 80. The olefinic moiety of 80 is transformed into a β-lactam ring via reaction with chlorosulfonylisocyanate and subsequent reduction of the intermediate with a reductant such as sodium sulfite to produce 81. Removal of the benzyl group of 81 under hydrogenolytic conditions using a catalyst such as palladium-on-carbon produces 82. Reaction of 82 with 2-chloro-2-oxo-1,3,2-dioxaphospholane [Edmundson, R. N.; Chem. Ind. (London) 1962, 1828] in the presence of a base such as triethylamine produces a cyclic phosphate which is opened by reaction with trimethylamine to produce 83.

The syntheses of the various starting materials cited hereinabove have been described previously and, in addition, require for their synthesis the use of synthetic methods and procedures widely known to those skilled in the art. Furthermore, descriptions of various applicable preparations have been described in U.S. Pat. Nos. 4,640,913, 4,697,031, 4,703,130, 4,699,990, 4,762,942, 4,883,816 and 4,894,367, copending application Serial No. 679,790 filed Dec. 10, 1984 and Tereshita, Z., et al., Life Sci., 32, 1975 (1983). The above patents, applications and citations describe the preparations of both optically active and racemic materials, therefore, the compounds of this invention can be prepared both as racemates and as individual R and S enantiomers.

The compounds of this invention were tested for pharmacological activity as described in the following tests.

IN VITRO PORCINE PANCREATIC PHOSPHOLIPASE (PLA2) ASSAY

Phospholipase $A_2$ activity was measured by a radiochemical assay in which labeled synthetic phosphatidylcholine substrate is converted by porcine pancreatic $PLA_2$ to free radiolabeled arachidonate and lyso PC. Radiolabeled arachidonate is extracted from the reaction mixture and separated from unreacted substrate by column chromatography or TLC. Radioactivity (cpm) in samples is quantitated by liquid scintillation counting. Specific details are as follows:

Labeled substrate(1-stearyl-2-$^3$H-arachidonylphosphatidylcholine; Amersham, sp. act. 84 (uCi/mmole, 0.025 to 0.2 uCi/assay tube and unlabeled substrates (Avanti), in sufficient quantity to give 20,000 cpm to 50,000 cpm and 10 $\mu$M to 1,000 $\mu$M final concentration/assay tube are dried under a stream of nitrogen. The $PLA_2$ and $mPLA_2$ assays utilized a 2 nM substrate concentration. The $mHPLA_2$ and $HPLA_2$ assays (vida infra) utilized a 10 $\mu$M substrate concentration and the $SmPLA_2$ assay utilized a substrate concentration ranging from 100 to 1000 $\mu$m. The substrate is then redissolved in 0.1M tris-HCl buffer, pH 9.0 containing 10 mM $CaCl_2$ and 10 mM Na taurocholate detergent. The mixture is sonicated in a Kontes Sonifier to yield a homogeneous dispersion. The "mixed" micellar substrate is clear. An aliquot is reserved for a cpm count (total substrate). The total reaction volume is 500 $\mu$L; siliconized glassware or plasticware is used throughout. Enzyme (Sigma, sp. act.>690 U/mg protein and preferably 900 U/mg protein) is diluted 1:750 or 1:1000 in 0.1M tris-HCl buffer, pH 9.0 (without $Ca^{++}$ and detergent). Enzyme dilution depends on substrate concentration and required enzyme concentration.

The substrate in buffer is kept on ice until the reaction is started. The reaction is started by adding 10 $\mu$L of diluted enzyme solution to 490 $\mu$L of micellar substrate solution. Samples are incubated in a 37° C. water bath for 15 minutes with gentle mixing. The reaction is terminated by the addition of 100 $\mu$L of 1M fresh trichloroacetic acid (TCA) solution and chilling the tubes on ice for 30 minutes.

Samples (600 $\mu$L) are extracted with 3 ml $CHCl_3$/MeOH (2:1) for thin layer chromatography or in hexane/ether (9:1) for column chromatography. The phases are separated by gentle centrifugation at 700 rpm$\times$5'. The organic phase is recovered.

THIN LAYER CHROMATOGRAPHY

Labeled arachidonate extracted with $CHCl_3$/MeOH is separated on silica gel G TLC plates (Analtech). Twenty $\mu$L of a 2 mg/ml internal standard solution of arachidonic acid (Sigma) is combined with 2-3 ml of the organic phase. The entire mixture is dried under nitrogen and redissolved in 50 $\mu$L of $CHCl_3$/MeOH (2:1). A 20 $\mu$L sample is counted in 10 ml of Beckman Redi-solv HP and spotted on silica gel G plates. The solvent system used to develop the plate is $CHCl_3$/MeOH/13.5N $NH_3$/$H_2O$ (70:30:4:1). Plates are developed in a glass chamber for 1-1½ hours, air dried, and the spots visualized in an iodine vapor chamber. Standards of phosphatidylcholine, lyso PC, and arachidonic acid (Sigma) are made as 2 mg/ml stocks in $CHCl_3$/MeOH (2:1) and spotted on plates. Spots corresponding to arachidonate and phospholipid are scraped and counted in 10 ml Beckman Redi-Solv HP scintillation fluid.

COLUMN CHROMATOGRAPHY

Samples are extracted with hexane/ether and the upper organic phase recovered. An aliquot is applied to a Silicar $CC_4$ (Malincrodt) column. Columns are prepared using 1 ml of a 1:1 slurry of silicar $CC_4$ in hexane/ether in a Pasteur pipet (approx. 2 cm height). Columns are rinsed with 500 $\mu$L of hexane/ether before adding the sample (300-600 $\mu$L) to the column. Columns are eluted with a total of 6 ml of hexane/ether. The 6 ml sample is counted in 10 ml of Beckman Redi-Solv HP scintillation fluid.

DRUG INHIBITORS IN ENZYME ASSAYS or the phospholipase $A_2$ assay, compounds are prepared as 1 mg/ml stock solutions in MeOH and diluted appropriately in PBS. Ten ul aliquots of the respective working stock solutions are either preincubated with phospholipase $A_2$ enzyme in buffer in the absence of $Ca^{++}$ or detergent for a specific time (enzyme preincubation design) or are blown down under a $N_2$ stream with the substrate prior to addition of buffer (mixed micellar design). Reactions are always begun by addition of enzyme (preincubated with compound or diluent or fresh) to substrate dispersion in buffer.

The assays are grouped as follows:
$PLA_2$ Assay: preincubation of drug+enzyme; substrate conc=2 nM
$MPLA_2$ Assay: mixed micelle design of drug+substrate connc=2 nM
$HPLA_2$ Assay: preincubation design; [s]=10 $\mu$m
$MHPLA_2$ Assay: mixed micelle design [s]=10 $\mu$m
$SMPLA_2$ Assay: mixed micelle design; [s]=100-100 $\mu$M The results of these tests are displayed in the following five tables.

TABLE I

| Compound | MHPLA$_2$ Dose $\mu$/ml | % Inh. | Avg. | IC$_{50}$ $\mu$/ml | Avg. | Subs. con. |
|---|---|---|---|---|---|---|
| 2,5,7-Trioxa-6-phosphanonan-9-aminium, 1-carboxy-3-[(hexadecyloxy)methyl]-6-hydroxy-N,N,N-trimethyl-, hydroxide, inner salt, 6-oxide | 10 | 6 | | | | 10 |
| | 25 | 13 | 30 | | | 10 |
| | | 46 | | | | 10 |
| N-[3-(Hexadecyloxy)-2-hydroxymethyl)propyl]octadecanamide | 25 | 35 | | | | 10 |
| 4-[(Hexadecyloxy)methyl]-7-hydroxy-N,N,N-trimethyl-1,1-diphenoxy-2,6,8-trioxa-1,7-diphosphadecan-10-aminium, hydroxide, inner salt, 1,7-dioxide | 25 | 33 | | | | 10 |
| 3,5-Dioxa-9-thia-4-phosphapentacosan-1-aminium, 4-hydroxy-N,N,N-trimethyl-, hydroxide, inner salt, | 25 | STIM | | | | 10 |

TABLE I-continued

| Compound | MHPLA$_2$ Dose μ/ml | % Inh. | Avg. | IC$_{50}$ μ/ml | Avg. | Subs. con. |
|---|---|---|---|---|---|---|
| 4-oxide | | | | | | |
| 7-[(Hexadecylthio)methyl]-4-hydroxy-N,N,N-trimethyl-3,5,9-trioxa-4-phosphapentacosan-1-aminium, hydroxide, inner salt, 4-oxide | 10<br>20<br>25 | STIM<br>STIM<br>81 | | | | 10<br>10<br>10 |
| 7-[(Hexadecylsulfonyl)methyl]-4-hydroxy-N,N,N-trimethyl-3,5,9-trioxa-4-phosphapentacosan-1-aminium, hydroxide, inner salt, 4-oxide | 25 | 19 | | | | 10 |
| 4-Hydroxy-N,N,N-trimethyl-3,5-dioxa-9-thia-4-phosphapentacosan-1-aminium, hydroxide, inner salt, 4,9-trioxide | 10<br>20<br>25 | 0<br>19<br>24 | | 62.0 | | 10<br>10<br>10 |
| 4-Hydroxy-N,N,N-trimethyl-3,5-dioxa-9-thia-4-phosphapentacosan-1-aminium, hydroxide, inner salt, 4,9-dioxide | 25 | 16 | | | | |
| 9-Ethoxy-7-[(hexadecyloxy)methyl]-N,N,N-trimethyl-4-hydroxy-3,5,10-trioxa-4,9-diphosphadodecan-1-aminium, hydroxide, inner salt, 4,9-dihydroxide | 10<br>10<br>20<br>25 | 18<br>18<br>44<br>45<br>42<br>34 | | 56.2<br>163.0 | | |
| 4-Hydroxy-N,N,N-trimethyl-7-(2-propanyl)-3,5,9-trioxa-4-phosphapentacosan-1-aminium, hydroxide, inner salt, 4-oxide | 25 | 19 | | 10 | | |
| 4-Hydroxy-7-[2-hydroxyimino)ethyl]-N,N,N-trimethyl-3,5,9-trioxa-4-phosphapentacosan-1-aminium, hydroxide, inner salt, 4-oxide | 10<br>20<br>25 | 0<br>8<br>28 | | | | 10<br>10<br>10 |
| 7-(Boronomethyl)-4-hydroxy-N,N,N-trimethyl-3,5,9-trioxa-4-phosphapentacosan-1-aminium, hydroxide, inner salt, 4-oxide | 25 | 9 | | | | 10 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide | 10<br>25 | 0<br>STIM | | | | 10 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide | 10<br>25<br>25<br>25<br>25 | 0<br>0<br>24<br>100<br>STIM | 62 | | | 10<br>10<br>10<br>10 |
| 3,5,8,10-Tetraoxa-4,9-diphosphahexacosan-1-aminium, 7-[(hexadecyloxy)methyl]-4,9-dihydroxy-N,N,N-trimethyl-, hydroxide, 4-(inner salt), 4,9-dioxide | 10<br>25<br>25 | STIM<br>STIM<br>STIM | | | | 10<br>10<br>10 |
| 3,5,8,10-Tetraoxa-4,9-diphosphahexacosan-1-aminium, 7-[(hexadecyloxy)methyl]-4,9-dihydroxy-N,N,N-trimethyl-, hydroxide, 4-(inner salt), 4,9-dioxide, (7S) | 10<br>25<br>25 | STIM<br>STIM<br>STIM | | | | 10<br>10<br>10 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide, 7(S)-, upper diastereomer | 25 | 0 | | | | 10 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide, (7R)-, upper diastereomer | 25 | 7 | | | | 10 |
| 3,5,8,10-Tetraoxa-4,9-diphosphahexacosan-1-aminium, 7-[(hexadecyloxy)methyl]-4,9-dihydroxy-N,N,N-trimethyl-, hydroxide, 4-(inner salt), 4,9-dioxide | 25 | 1 | | | | 10 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-oxide, | 25 | 9 | | | | 10 |

TABLE I-continued

| Compound | MHPLA$_2$ Dose μ/ml | % Inh. | Avg. | IC$_{50}$ μ/ml | Avg. | Subs. con. |
|---|---|---|---|---|---|---|
| (7S)-, lower diastereomer | | | | | | |
| 7-(2-Nonadecynyl)-4-hydroxy-N,N,N-trimethyl-3,5,9-trioxa-4-phosphapentacosan-1-aminium, hydroxide, inner salt, 4-oxide | 25 | 16 | | | | 10 |
| 7-(2,3-Dioxononadecyl)-4-hydroxy-N,N,N-trimethyl-3,5,9-trioxa-4-phosphapentacosan-1-aminium, hydroxide, inner salt, 4-oxide | 25 | 0 | | | | 10 |
| 3,5,8,10-Tetraoxa-4,9-diphosphapentadecan-1-aminium, 4-hydroxy-9-methoxy-N,N,N-trimethyl-7-[(pentyloxy)-methyl]-, hydroxide, inner salt, 4,9-dioxide | 25 | 0 | | | | 10 |
| 3,5,8,10-Tetraoxa-4,9-diphosphapentadecan-1-aminium, 4,9-dihydroxy-N,N,N-trimethyl-7-[(pentyloxy)methyl]-, hydroxide, 4-(inner salt), 4,9-dioxide | 25 | 12 | | | | 10 |
| 7-(2-Aminooctadecyl)-4-hydroxy-N,N,N-trimethyl-3,5,9-trioxa-4-phosphapentacosan-1-aminium, hydroxide, inner salt, 4-oxide | 10 | 93 | | 1.4 | | 10 |
| | 10 | 59 | 70 | 5.2 | 4.3 | 10 |
| | 10 | 59 | | 6.4 | | 10 |
| | 20 | 97 | | | | 10 |
| | 25 | 78 | | | | 10 |
| | 25 | 76 | 77 | | | 10 |
| | 25 | 78 | | | | 10 |
| 3,5,8,10-Tetraoxa-4,9-diphosphapentadecan-1-aminium, 7-[(hexadecyloxy)methyl]-4,hydroxy-9-methoxy-N,N,N-trimethyl-, hydroxide, 4-(inner salt), 4,9-dioxide, less polar isomer | 10 | STIM | | | | |
| | 25 | STIM | | | | |
| | 25 | STIM | | | | |
| 3,5,8,10-Tetraoxa-4,9-diphosphapentadecan-1-aminium, 7-[(hexadecyloxy)methyl]-4,hydroxy-9-methoxy-N,N,N-trimethyl-, hydroxide, 4-(inner salt), 4,9-dioxide, more polar isomer | 10 | 0 | | | | |
| | 25 | STIM | | | | |
| | 25 | STIM | | | | |
| 3,5,8,10-Tetraoxa-4,9-diphosphapentadecan-1-aminium, 7-[(hexadecyloxy)methyl]-4,9-dihydroxy-N,N,N-trimethyl-, hydroxide, 4-(inner salt), 4,9-dioxide, | 10 | STIM | | | | |
| | 25 | STIM | | | | |
| | 25 | STIM | | | | |
| 3,5,9-Trioxa-4-phosphapentacosan-1-aminium, 7-(3,3-difluoro-2-methylenenonadecyl)-4-hydroxy-N,N,N-trimethyl-, hydroxide, inner salt, 4-oxide | 25 | 11 | | | | |
| 3,5,9-Trioxa-4-phosphapentacosan-1-aminium, 7-(3,3-difluoro-2-oxononadecyl)-4-hydroxy-N,N,N-trimethyl-, hydroxide, inner salt, 4-oxide | 10 | 0 | | | | 10 |
| | 20 | 9 | | | | 10 |
| | 25 | 8 | | | | 10 |
| 3,5,9-Trioxa-4-phosphapentacosan-1-aminium, 7-(3,3-difluoro-2-hydroxynonadecyl)-4-hydroxy-N,N,N-trimethyl-, hydroxide, inner salt, 4-oxide | 25 | 11 | | | | 10 |
| (2R)-2-[[[(2-Hexadecyl-4-oxo-2-azetidinyl)methoxy]hydroxyphosphinyl]oxy]-N,N,N-trimethyl-ethanaminium, hydroxide, inner salt | 10 | STIM | | | | 10 |
| | 20 | 0 | | | | 10 |
| | 25 | 26 | | | | 10 |
| 3,5,9-Trioxa-4-phosphapentacosan-1-aminium, 7-[(bromoacetyl)oxy]-4-hydroxy-N,N,N-trimethyl-, hydroxide, inner salt, 4-oxide | 10 | 35 | | 7.9 | | 10 |
| | 10 | 24 | 32 | 26.6 | 50 | 10 |
| | 10 | 35 | | 35.5 | | 10 |
| | 10 | 34 | | 130.0 | | 10 |
| | 25 | 78 | | | | 10 |
| | 25 | 29 | | | | 10 |
| | 25 | 54 | 50 | | | 10 |
| | 25 | 43 | | | | 10 |
| | 25 | 52 | | | | 10 |
| | 25 | 50 | | | | 10 |
| | 25 | 44 | | | | 10 |
| 7-[(Chloroacetyl)oxy]-4-hydroxy-N,N,N-trimethyl-3,5,9-trioxa-4-phosphapentacosan-1-aminium, hydroxide, inner salt, 4-oxide | 10 | 27 | | | | 10 |
| | 25 | 3 | | | | 10 |
| | 25 | 35 | 3 | | | 10 |
| | 25 | 0 | | | | 10 |
| 10-Bromo-7-[(hexadecyloxy)methyl]-4-hydroxy-N,N,N-trimethyl-9-oxo- | 10 | 3 | 8 | | | 10 |
| | 10 | 14 | | | | 10 |

TABLE I-continued

| Compound | MHPLA₂ Dose μ/ml | % Inh. | Avg. | IC₅₀ μ/ml | Avg. | Subs. con. |
|---|---|---|---|---|---|---|
| 3,5,8-trioxa-4-phosphahexacosan-1-aminium, hydroxide, inner salt, 4-oxide | 25 | 0 | | | | 10 |
| | | 20 | 10 | | | 10 |
| | | 0 | | | | 10 |
| | | 19 | | | | 10 |
| | 50 | 37 | 137 | | | 10 |
| 7-[(Hexadecylsulfinyl)methyl]-4-hydroxy-N,N,N-triimethyl-3,5,9-trioxa-4-phosphapentacosan-1-aminium, hydroxide, inner salt, 4-oxide | 10 | 3 | | | | 10 |
| | 20 | 22 | | | | 10 |
| | 25 | 68 | | | | 10 |

TABLE II

| Compound | SMPLA₂ Dose μ/ml | % Inh. | Avg. | IC₅₀ μ/ml | Avg. | Subs. con. |
|---|---|---|---|---|---|---|
| 7-(2-Aminooctadecyl)-4-hydroxy-N,N,N-trimethyl-3,5,9-trioxa-4-phosphapentacosan-1-aminium, hydroxide, inner salt, 4-oxide | 25 | 63 | 61 | 15.1 | 20 | 100 |
| | 25 | 59 | | 25.0 | | 100 |
| 3,5,8,10-Tetraoxa-4,9-diphosphapentadecan-1-aminium, 7-[(hexadecyloxy)methyl]-4,9-dihydroxy-N,N,N-trimethyl-, hydroxide, 4-(inner salt), 4,9-dioxide | 10 | STIM | | | | 100 |
| | 10 | 7 | | | | 500 |
| | 10 | 22 | | | | 1000 |
| | 25 | STIM | | | | 100 |
| | 25 | 29 | | | | 500 |
| | 25 | 3 | | | | 1000 |
| | 50 | STIM | | | | 100 |
| | 50 | STIM | | | | 500 |
| | 50 | STIM | | | | 1000 |
| 10-Bromo-7-[(hexadecyloxy)methyl]-4-hydroxy-N,N,N-trimethyl-9-oxo-3,5,8-trioxa-4-phosphahexacosan-1-aminium, hydroxide, inner salt, 4-oxide | 10 | 8 | | | | 100 |
| | 10 | 0 | | | | 500 |
| | 10 | 5 | | | | 1000 |
| | 25 | 1 | | | | 100 |
| | 25 | 0 | | | | 500 |
| | 25 | 10 | | | | 1000 |
| | 50 | 18 | | | | 100 |
| | 50 | 8 | | | | 500 |
| | 50 | 6 | | | | 1000 |

TABLE III

| Compound | PLA₂ Dose μ/ml | % Inh. | Avg. | IC₅₀ μ/ml | Avg. | Subs. con. |
|---|---|---|---|---|---|---|
| 2,5,7-Trioxa-6-phosphanonan-9-aminium, 1-carboxy-3-[(hexadecyloxy)methyl]-6-hydroxy-N,N,N-trimethyl-, hydroxide, inner salt, 6-oxide | 20 | 44 | | | | 2 |
| N-[3-(Hexadecyloxy)-2-hydroxymethyl)propyl]octadecanamide | 20 | 24 | | | | 2 |
| | 25 | 93 | | | | 2 |
| 4-[(Hexadecyloxy)methyl]-7-hydroxy-N,N,N-trimethyl-1,1-diphenoxy-2,6,8-trioxa-1,7-diphosphadecan-10-aminium, hydroxide, inner salt, 1,7-dioxide | 10 | 75 | | 4.8 | | 2 |
| | 20 | 85 | | | | 2 |
| 3,5-Dioxa-9-thia-4-phosphapentacosan-1-aminium, 4-hydroxy-N,N,N-trimethyl-, hydroxide, inner salt, 4-oxide | 10 | 54 | | 6.2 | | 2 |
| | 10 | 39 | | | | 2 |
| | 10 | 43 | 4.5 | | | 2 |
| | 10 | 47 | | | | 2 |
| | 10 | 44 | | | | 2 |
| | 20 | 64 | | | | 2 |
| 7-[(Hexadecylthio)methyl]-4-hydroxy-N,N,N-trimethyl-3,5,9-trioxa-4-phosphapentacosan-1-aminium, hydroxide, inner salt, 4-oxide | 10 | 60 | 26 | | | 2 |
| | 10 | 23 | | | | 2 |
| | 10 | 14 | | | | 2 |
| | 10 | 20 | | | | 2 |
| | 10 | 13 | | | | 2 |
| | 20 | 61 | | 3.5 | | 2 |
| 2-[[(2-Bromoethoxy)hydroxyphosphinyl]oxy]ethyl hexadecyl phosphoric acid, methyl ester | 10 | 42 | 21 | | | 2 |
| | 10 | 1 | | | | 2 |
| 7-[(Hexadecylsulfonyl)methyl]-4-hydroxy-N,N,N-trimethyl-3,5,9-trioxa-4-phosphapentacosan-1-aminium, hydroxide, inner salt 4-oxide | 10 | 9 | 57 | 2.3 | | 2 |
| | 10 | 86 | | | | 2 |
| | 10 | 76 | | | | 2 |
| | 20 | 82 | | | | 2 |
| 3,9-Dihydroxy-N,N,N-trimethyl-3,5,8,10-tetraoxa-4,9-diphospha- | 10 | 4 | 20 | | | 2 |
| | 10 | 37 | | | | 2 |

TABLE III-continued

| Compound | PLA$_2$ Dose μ/ml | % Inh. | Avg. | IC$_{50}$ μ/ml | Avg. | Subs. con. |
|---|---|---|---|---|---|---|
| hexacosan-1-aminium, hydroxide, 4-(inner salt) 4,9-dioxide | 10 | 8 | 40 | | | 2 |
| 4,9-Dihydroxy-N,N,N-trimethyl-3,5,8,10-tetraoxa-4,9-diphosphaoctacosan-1-aminium, hydroxide, 4-(inner salt), 4,9-dioxide | 10 | 32 | | | | 2 |
| 4-Hydroxy-N,N,N-trimethyl-3,5-dioxa-9-thia-4-phosphapentacosan-1-aminium, hydroxide, inner salt, 4,9-trioxide | 10 | 65 | 69 | 4.9 | | 2 |
| | 10 | 74 | | | | 2 |
| | 20 | 88 | | | | 2 |
| 4-Hydroxy-N,N,N-trimethyl-3,5-dioxa-9-thia-4-phosphapentacosan-1-aminium, hydroxide, inner salt, 4,9-dioxide | 10 | 59 | 61 | 6.2 | | 2 |
| | 10 | 63 | | | | 2 |
| | 20 | 82 | | | | 2 |
| 9-Ethoxy-7-[(hexadecyloxy)methyl]-N,N,N-triimethyl-4-hydroxy-3,5,10-trioxa-4,9-diphosphadodecan-1-aminium, hydroxide, inner salt, 4,9-dihydroxide | 10 | 71 | 74 | 5.0 | | 2 |
| | 10 | 77 | | | | 2 |
| | 20 | 81 | | | | 2 |
| 4-Hydroxy-N,N,N-trimethyl-7-(2-propanyl)-3,5,9-trioxa-4-phosphapentacosan-1-aminium, hydroxide, inner salt, 4-oxide | 10 | 75 | 80 | 1.6 | | 2 |
| | 10 | 85 | | | | 2 |
| | 20 | 91 | | | | 2 |
| 4-Hydroxy-N,N,N-trimethyl-7-(oxiranylmethyl)-3,5,9-trioxa-4-phosphapentacosan-1-aminium, hydroxide, inner salt, 4-oxide | 10 | 71 | 74 | 2.4 | | 2 |
| | 10 | 77 | | | | 2 |
| | 20 | 88 | | | | 2 |
| 4-Hydroxy-N,N,N-trimethyl-7-(2-oxoethyl)-3,5,9-trioxa-4-phosphapentacosan-1-aminium, hydroxide, inner salt, 4-oxide | 10 | 47 | 43 | 13.2 | | 2 |
| | 10 | 39 | | | | 2 |
| | 20 | 62 | | | | 2 |
| 4-Hydroxy-7-[2-(hydroxyimino)ethyl]-N,N,N-trimethyl-3,5,9-trioxa-4-phosphapentacosan-1-aminium, hydroxide, inner salt, 4-oxide | 10 | 56 | 53 | 5.3 | | 2 |
| | 10 | 49 | | | | 2 |
| | 20 | 81 | | | | 2 |
| 7-(Boronomethyl)-4-hydroxy-N,N,N-trimethyl-3,5,9-trioxa-4-phosphapentacosan-1-aminium, hydroxide, inner salt, 4-oxide | 10 | 57 | | 5.6 | | 2 |
| | 20 | 77 | | | | 2 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide | 10 | 61 | 68 | 6.0 | 5.4 | 2 |
| | 10 | 70 | | 4.5 | | 2 |
| | 10 | 73 | | 5.8 | | 2 |
| | 20 | 65 | | | | |
| | 25 | 71 | 77 | | | |
| | 25 | 83 | | | | |
| | 50 | 73 | 80 | | | |
| | 50 | 88 | | | | |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide | 10 | 72 | 30 | 3.2 | 3 | 2 |
| | 10 | 78 | | 2.8 | | 2 |
| | 25 | 72 | 75 | | | 2 |
| | 25 | 85 | | | | 2 |
| | 50 | 68 | 77 | | | 2 |
| | 50 | 87 | | | | 2 |
| 4-Hydroxy-N,N,N-trimethyl-7-(2-methyleneoctadcyl)-3,5,9-trioxa-4-phosphapentacosan-1-aminium, hydroxide, inner salt, 4-oxide | 10 | 59 | 62 | 3.8 | | 2 |
| | 10 | 65 | | | | 2 |
| | 20 | 52 | | | | 2 |
| 4-Hydroxy-N,N,N-trimethyl-7-(2-oxooctadecyl)-3,5,9-trioxa-4-phosphapentacosan-1-aminium, hydroxide inner salt, 4-oxide | 10 | 59 | 60 | 5.8 | | 2 |
| | 10 | 61 | | | | 2 |
| | 20 | 62 | | | | 2 |
| 7-[(2-Hexadecyloxiranyl)methyl]-4-hydroxy-N,N,N-trimethyl-3,5,9-trioxa-4-phosphapentacosan-1-aminium, hydroxide, inner salt, 4-oxide | 10 | 78 | | 1.8 | | 2 |
| | 20 | 75 | | | | 2 |
| 4-Hydroxy-7-(2-hydroxy-2-methyloctadecyl)-N,N,N-trimethyl-3,5,9-trioxa-4-phosphapentacosan-1-aminium, hydroxide, inner salt, 4-oxide | 10 | 65 | 64 | 5.9 | | 2 |
| | 10 | 62 | | | | 2 |
| | 20 | 66 | | | | 2 |
| 4-Hydroxy-7-(2-hydroxyoctadecyl)-N,N,N-trimethyl-3,5,9-trioxa-4-phosphapentacosan-1-aminium, hydroxide, inner salt, 4-oxide | 10 | 80 | | 1.6 | | 2 |
| | 20 | 80 | | | | 2 |
| 4-Hydroxy-7-(2-hydroxyoctadecyl)-N,N,N-trimethyl-3,5,9-trioxa-4-phosphapentacosan-1-aminium, | 10 | 80 | | 1.7 | | 2 |
| | 20 | 80 | | | | 2 |

TABLE III-continued

| Compound | PLA$_2$ Dose μ/ml | % Inh. | Avg. | IC$_{50}$ μ/ml | Avg. | Subs. con. |
|---|---|---|---|---|---|---|
| hydroxide, inner salt, 4-oxide isomer | | | | | | |
| 3,5,8,10-Tetraoxa-4,9-diphospha- | 10 | 19 | 22 | | | 2 |
| hexacosan-1-aminium, 7-[(hexa- | 10 | 9 | | | | 2 |
| decyloxy)methyl]-4-hydroxy-9- | 10 | 48 | | | | 2 |
| methoxy-N,N,N-trimethyl-, | 10 | 14 | | | | 2 |
| hydroxide, inner salt, 4,9- | 20 | 32 | 34 | 13.7 | | 2 |
| dioxide (7R)-, lower diastereomer | 20 | 14 | | | | 2 |
| | 20 | 55 | | | | 2 |
| 3,5,8,10-Tetraoxa-4,9-diphospha- | 10 | 14 | 17 | | | 2 |
| hexacosan-1-aminium, 7-[(hexa- | 10 | 2 | | | | 2 |
| decyloxy)methyl]-4,9-dihydroxy- | 10 | 34 | | | | 2 |
| N,N,N-trimethyl-, hydroxide, | 20 | 15 | 16 | | | 2 |
| 4-(inner salt), 4,9-dioxide, (7S) | 20 | 2 | | | | 2 |
| | 20 | 32 | | | | 2 |
| | 25 | 8 | | | | 2 |
| 3,5,8,10-Tetraoxa-4,9-diphospha- | 10 | 70 | 29 | | | 2 |
| hexacosan-1-aminium, 7-[(hexa- | 10 | 17 | | | | 2 |
| decyloxy)methyl]-4-hydroxy-9- | 10 | 0 | | | | 2 |
| methoxy-N,N,N-trimethyl-, | 20 | 74 | 26 | | | 2 |
| hydroxide, inner salt, 4,9- | 20 | 4 | | | | 2 |
| dioxide, 7(S)-, upper diastereo- | 20 | 0 | | | | 2 |
| mer | | | | | | |
| 3,5,8,10-Tetraoxa-4,9-diphospha- | 10 | 79 | 30 | | | 2 |
| hexacosan-1-aminium, 7-[(hexa- | 10 | 12 | | | | 2 |
| decyloxy)methyl]-4-hydroxy-9- | 10 | 0 | | | | 2 |
| methoxy-N,N,N-trimethyl-, | 20 | 76 | 28 | | | 2 |
| hydroxide, inner salt, 4,9- | 20 | 7 | | | | 2 |
| dioxide, (7R)-, upper | 20 | 0 | | | | 2 |
| diastereomer | 25 | 93 | | 2.0 | | 2 |
| 3,5,8,10-Tetraoxa-4,9-diphospha- | 10 | 71 | 27 | | | 2 |
| hexacosan-1-aminium, 7-[(hexa- | 10 | 0 | | | | 2 |
| decyloxy)methyl]-4,9-dihydroxy- | 10 | 6 | | | | 2 |
| N,N,N-trimethyl-, hydroxide, | 20 | 72 | | | | 2 |
| 4-(inner salt), 4,9-dioxide | 20 | 4 | | | | 2 |
| | 25 | 91 | | 2.5 | | 2 |
| 3,5,8,10-Tetraoxa-4,9-diphospha- | 10 | 72 | 25 | | | 2 |
| hexacosan-1-aminium, 7-[(hexa- | 10 | 3 | | | | 2 |
| decyloxy)methyl]-4-hydroxy-9- | 10 | 0 | | | | 2 |
| methoxy-N,N,N-trimethyl-, | 20 | 78 | 39 | 3.3 | | 2 |
| hydroxide, inner salt, 4,9-oxide | 20 | 0 | | | | 2 |
| (7S)-, lower diastereomer | 25 | 91 | | | | 2 |
| 7-(2-Nonadecynyl)-4-hydroxy- | 10 | 57 | | 4.9 | | 2 |
| N,N,N-trimethyl-3,5,9-trioxa- | 20 | 60 | | | | 2 |
| 4-phosphapentacosan-1-aminium, | | | | | | |
| hydroxide, inner salt, 4-oxide | | | | | | |
| 7-(2,3-Dioxononadecyl)-4-hydroxy- | 10 | 61 | | 5.4 | | 2 |
| N,N,N-trimethyl-3,5,9-trioxa-4- | 20 | 61 | | | | 2 |
| phosphapentacosan-1-aminium, | | | | | | |
| hydroxide, inner salt, 4-oxide | | | | | | |
| 3,5,8,10-Tetraoxa-4,9-diphospha- | 10 | 5 | | | | 2 |
| pentadecan-1-aminium, 4-hydroxy- | 20 | 11 | | | | 2 |
| 9-methoxy-N,N,N-trimethyl-7- | | | | | | |
| [(pentyloxy)-methyl]-, hydroxide, | | | | | | |
| inner salt, 4,9-dioxide | | | | | | |
| 3,5,8,10-Tetraoxa-4,9-diphospha- | 10 | 20 | | | | 2 |
| pentadecan-1-aminium, 4,9-di- | 20 | 17 | | | | 2 |
| hydroxy-N,N,N-trimethyl-7- | | | | | | |
| [(pentyloxy)methyl]-, hydroxide, | | | | | | |
| 4-(inner salt), 4,9-dioxide | | | | | | |
| 7-(2-Aminooctadecyl)-4-hydroxy- | 10 | 95 | | 0.5 | | 2 |
| N,N,N-trimethyl-3,5,9-trioxa-4- | 20 | 95 | | | | 2 |
| phosphapentacosan-1-aminium, | | | | | | |
| hydroxide, inner salt, 4-oxide | | | | | | |
| 3,5,8,10-Tetraoxa-4,9-diphospha- | 10 | 76 | | 5.2 | | 2 |
| pentadecan-1-aminium, 7-[(hexa- | 20 | 83 | | | | 2 |
| decyloxy)methyl]-4-hydroxy-9- | | | | | | |
| methoxy-N,N,N-trimethyl-, | | | | | | |
| hydroxide, 4-(inner salt), | | | | | | |
| 4,9-dioxide, less polar isomer | | | | | | |
| 3,5,8,10-Tetraoxa-4,9-diphos- | 10 | 82 | | 2.5 | | 2 |
| phapentadecan-1-aminium, 7- | 20 | 89 | | | | 2 |
| [(hexadecyloxy)methyl]-4-hy- | | | | | | |
| droxy-9-methoxy-N,N,N-trimethyl-, | | | | | | |
| hydroxide, 4-(inner salt, 4,9- | | | | | | |
| dioxide, more polar isomer | | | | | | |
| 3,5,8,10-Tetraoxa-4,9-diphos- | 10 | 21 | | | | 2 |
| phapentadecan-1-aminium, 7- | 20 | 41 | | | | 2 |
| [(hexadecyloxy)methyl]-4,9- | | | | | | |
| dihydroxy-N,N,N-trimethyl-, | | | | | | |

TABLE III-continued

| Compound | PLA$_2$ Dose μ/ml | % Inh. | Avg. | IC$_{50}$ μ/ml | Avg. | Subs. con. |
|---|---|---|---|---|---|---|
| hydroxide, 4-(inner salt), 4,9-dioxide | | | | | | |
| 3,5,9-Trioxa-4-phosphapenta-cosan-1-aminium, 7-(3,3-di-fluoro-2-methylenenonadecyl)-4-hydroxy-N,N,N-trimethyl-, hydroxide, inner salt, 4-oxide | 10 | 38 | | | | 2 |
| | 20 | 38 | | | | 2 |
| 3,5,9-Trioxa-4-phosphapentacosan-1-aminium, 7-(3,3-difluoro-2-oxononadecyl)-4-hydroxy-N,N,N-trimethyl-, hydroxide, inner salt, 4-oxide | 10 | 38 | | | | 2 |
| | 20 | 41 | | | | 2 |
| 3,5,9-Trioxa-4-phosphapentacosan-1-aminium, 7-(3,3-difluoro-2-hydroxynonadecyl)-4-hydroxy-N,N,N-trimethyl-, hydroxide, inner salt, 4-oxide | 10 | 45 | | | | 2 |
| | 20 | 49 | | | | 2 |
| 7-(2-Aminobutyl)-4,7-dihydroxy-N,N,N-trimethyl-3,5,9-trioxa-4-phosphapentacosan-1-aminium, hydroxide, inner salt, 4-oxide | 10 | 89 | | 1.3 | | 2 |
| | 20 | 94 | | | | 2 |
| (2R)-2-[[[(2-Hexadecyl-4-oxo-2-azetidinyl)methoxy]hydroxyphosphinyl]oxy]-N,N,N-trimethyl-ethanaminium, hydroxide, inner salt | 10 | 82 | | 1.4 | | 2 |
| | 20 | 79 | | | | 2 |
| 7-[(Hexadecylsulfinyl)methyl]-4-hydroxy-N,N,N-trimethyl-3,5,9-trioxa-4-phosphapentacosan-1-aminium, hydroxide, inner salt, 4-oxide | 10 | 23 | 66 | 1.4 | | 2 |
| | 10 | 88 | | | | 2 |
| | 10 | 88 | | | | 2 |
| | 20 | 93 | | | | 2 |

TABLE IV

| Compound | HPLA$_2$ Dose μ/ml | % Inh. | Avg. | IC$_{50}$ μ/ml | Avg. | Subs. con. |
|---|---|---|---|---|---|---|
| 3,5,8,10-Tetraoxa-4,9-diphospha-hexacosan-1-aminium, 7-[(hexadecyloxy)methyl]-4,9-dihydroxy-N,N,N-trimethyl-hydroxide, 4-(inner salt), 4,9-dioxide | 10 | STIM | | | | 10 |
| | 10 | STIM | | | | 10 |
| | 10 | 0 | | | | 10 |
| | 10 | 3 | | | | 10 |
| | 20 | STIM | | | | 10 |
| | 20 | STIM | | | | 10 |
| | 20 | 0 | | | | 10 |
| | 20 | 0 | | | | 10 |
| | 50 | STIM | | | | 10 |
| | 50 | STIM | | | | 10 |
| | 50 | 0 | | | | 10 |
| | 50 | 0 | | | | 10 |
| 3,5,8,10-Tetraoxa-4,9-diphospha-hexacosan-1-aminium, 7-[(hexadecyloxy)methyl]-4,9-dihydroxy-N,N,N-trimethyl-hydroxide, 4-(inner salt), 4,9-dioxide | 10 | STIM | | | | 10 |
| | 10 | STIM | | | | 10 |
| | 10 | 0 | | | | 10 |
| | 10 | 0 | | | | 10 |
| | 20 | STIM | | | | 10 |
| | 20 | STIM | | | | 10 |
| | 20 | 0 | | | | 10 |
| | 20 | 0 | | | | 10 |
| | 50 | STIM | | | | 10 |
| | 50 | STIM | | | | 10 |
| | 50 | 0 | | | | 10 |
| | 50 | STIM | | | | 10 |
| 3,5,8,10-Tetraoxa-4,9-diphospha-hexacosan-1-aminium, 7-[(hexadecyloxy)methyl]-4-hydroxy-9-methoxy-N,N,N-trimethyl-, hydroxide, inner salt, 4,9-dioxide, 7(S)-, upper diastereomer | 10 | 1 | 22 | | | 10 |
| | 10 | 20 | | | | 10 |
| | 10 | 36 | | | | 10 |
| | 10 | 22 | | | | 10 |
| | 20 | 18 | 18 | | | 10 |
| | 20 | 0 | | | | 10 |
| | 20 | 12 | | | | 10 |
| | 20 | 42 | | | | 10 |
| | 50 | 28 | 23 | | | 10 |
| | 50 | 34 | | | | 10 |
| | 50 | 8 | | | | 10 |
| | 50 | 23 | | | | 10 |
| 3,5,8,10-Tetraoxa-4,9-diphospha-hexacosan-1-aminium, 7-[(hexadecyloxy)methyl]-4-hydroxy-9-methoxy-N,N,N-trimethyl-, hydroxide, inner salt, 4,9-dioxide, (7R)-, upper | 10 | 18 | 17 | | | 10 |
| | 10 | 0 | | | | 10 |
| | 10 | 17 | | | | 10 |
| | 10 | 34 | | | | 10 |
| | 20 | 26 | 21 | | | 10 |
| | 20 | 0 | | | | 10 |

TABLE IV-continued

| Compound | HPLA$_2$ Dose μ/ml | % Inh. | Avg. | IC$_{50}$ μ/ml | Avg. | Subs. con. |
|---|---|---|---|---|---|---|
| diastereomer | 20 | 16 | | | | 10 |
| | 20 | 41 | | | | 10 |
| | 50 | 42 | 30 | | | 10 |
| | 50 | 23 | | | | 10 |
| | 50 | 9 | | | | 10 |
| | 50 | 44 | | | | 10 |
| 3,5,8,10-Tetraoxa-4,9-diphospha-hexacosan-1-aminium, 7-[(hexadecyloxy)methyl]-4,9-dihydroxy-N,N,N-trimethyl-, hydroxide, 4-(inner salt), 4,9-dioxide | 10 | 5 | 18 | | | 10 |
| | 10 | 14 | | | | 10 |
| | 10 | 3 | | | | 10 |
| | 10 | 48 | | | | 10 |
| | 20 | 16 | 22 | | | 10 |
| | 20 | 13 | | | | 10 |
| | 20 | 10 | | | | 10 |
| | 20 | 47 | | | | 10 |
| | 50 | 19 | 32 | | | 10 |
| | 50 | 52 | | | | 10 |
| | 50 | 9 | | | | 10 |
| | 50 | 47 | | | | 10 |
| 3,5,8,10-Tetraoxa-4,9-diphospha-hexacosan-1-aminium, 7-[(hexadecyloxy)methyl]-4-hydroxy-9-methoxy-N,N,N-trimethyl-, hydroxide, inner salt, 4,9-oxide, (7S)-, lower diastereomer | 10 | 11 | 18 | | | 10 |
| | 10 | 21 | | | | 10 |
| | 10 | 6 | | | | 10 |
| | 10 | 32 | | | | 10 |
| | 20 | 14 | 12 | | | 10 |
| | 20 | 0 | | | | 10 |
| | 20 | 2 | | | | 10 |
| | 20 | 32 | | | | 10 |
| | 50 | 24 | 25 | | | 10 |
| | 50 | 15 | | | | 10 |
| | 50 | 8 | | | | 10 |
| | 50 | 52 | | | | 10 |
| 7-[(Hexadecylsulfinyl)methyl]-4-hydroxy-N,N,N-trimethyl-3,5,9-trioxa-4-phosphapentacosan-1-aminium, hydroxide, inner salt, 4-oxide | 10 | 27 | 22 | | | 10 |
| | 10 | 17 | | | | 10 |
| | 20 | 33 | 33 | | | 10 |
| | 20 | 34 | | | | 10 |
| | 50 | 36 | 42 | | | 10 |
| | 50 | 47 | | | | 10 |

TABLE V

| Compound | MPLA$_2$ Dose μ/ml | % Inh. | Avg. | IC$_{50}$ μ/ml | Avg. | Subs. con. |
|---|---|---|---|---|---|---|
| N-[3-(Hexadecyloxy)-2-hydroxy-methyl)propyl]octadecanamide | 25 | STIM | | | | 2 |
| | 25 | 93 | | | | 2 |
| 4-[(Hexadecyloxy)methyl]-7-hydroxy-N,N,N-triimethyl-1,1-diphenoxy-2,6,8-trioxa-1,7-diphosphadecan-10-aminium, hydroxide, inner salt, 1,7-dioxide | 25 | 62 | 79 | | | 2 |
| | 25 | 97 | | | | 2 |
| 3,5-Dioxa-9-thia-4-phosphapenta-cosan-1-aminium, 4-hydroxy-N,N,N-trimethyl-, hydroxide, inner salt, 4-oxide | 10 | 46 | | 7.7 | | 2 |
| | 20 | 83 | | | | 2 |
| | 25 | 74 | 80 | | | 2 |
| | 25 | 86 | | | | 2 |
| 7-[(Hexadecylthio)methyl]-4-hydroxy-N,N,N-trimethyl-3,5,9-trioxa-4-phosphapentacosan-1-aminium, hydroxide, inner salt, 4-oxide | 10 | 59 | | 5.6 | | 2 |
| | 20 | 69 | | | | 2 |
| | 25 | 79 | | | | 2 |
| | 25 | STIM | | | | 2 |
| 7-[(Hexadecylsulfonyl)methyl]-4-hydroxy-N,N,N-trimethyl-3,5,9-trioxa-4-phosphapenta-cosan-1-aminium, hydroxide, inner salt, 4-oxide | 25 | 80 | 72 | | | 2 |
| | 25 | 64 | | | | 2 |
| 4-Hydroxy-N,N,N-trimethyl-3,5-dioxa-9-thia-4-phosphapentaco-san-1-aminium, hydroxide, inner salt, 4,9-trioxide | 10 | 24 | | 19.1 | | |
| | 20 | 62 | | | | |
| 4-Hydroxy-N,N,N-trimethyl-3,5-dioxa-9-thia-4-phosphapentaco-san-1-aminium, hydroxide, inner salt, 4,9-dioxide | 25 | 73 | 71 | | | 2 |
| | 25 | 68 | | | | 2 |
| 9-Ethoxy-7-[(hexadecyloxy)methyl]-N,N,N-trimethyl-4-hydroxy-3,5,10-trioxa-4,9-diphosphadodecan-1-aminium, hydroxide, inner salt, 4,9-dihydroxide | 10 | 36 | | 16.8 | | 2 |
| | 20 | 60 | | | | 2 |
| | 25 | 66 | 78 | | | 2 |
| | 25 | 90 | | | | 2 |
| 4-Hydroxy-N,N,N-trimethyl-7-(2-propanyl)-3,5,9-trioxa-4-phos-phapentacosan-1-aminium, hydrox- | 25 | STIM | | | | 2 |
| | 25 | 85 | | | | 2 |

TABLE V-continued

| Compound | MPLA$_2$ Dose μ/ml | % Inh. | Avg. | IC$_{50}$ μ/ml | Avg. | Subs. con. |
|---|---|---|---|---|---|---|
| ide, inner salt, 4-oxide | | | | | | |
| 4-Hydroxy-N,N,N-trimethyl-7-(oxiranylmethyl)-35,9-trioxa-4-phosphapentacosan-1-aminium, hydroxide, inner salt, 4-oxide | 25<br>25 | STIM<br>85 | | | | 2<br>2 |
| 4-Hydroxy-7-[2-(hydroxyimino)ethyl]-N,N,N-trimethyl-3,5,9-trioxa-4-phosphapentacosan-1-aminium, hydroxide, inner salt, 4-oxide | 10<br>20<br>25 | 19<br>57<br>51<br>60 | 55 | | | 2<br>2<br>2<br>2 |
| 7-(Boronomethyl)-4-hydroxy-N,N,N-trimethyl-3,5,9-trioxa-4-phosphapentacosan-1-aminium, hydroxide, inner salt, 4-oxide | 25<br>25 | 33<br>55 | 44 | | | 2<br>2 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide | 25<br>25 | 14<br>89 | 52 | | | 2<br>2 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide | 25<br>25 | STIM<br>54 | | | | 2<br>2 |
| 3,5,8,10-Tetraoxa-4,9-diphosphahexacosan-1-aminium, 7-[(hexadecyloxy)methyl]-4,9-dihydroxy-N,N,N-trimethyl-, hydroxide, 4-(inner salt), 4,9-dioxide | 25<br>25 | 28<br>0 | | | | 2<br>2 |
| 3,5,8,10-Tetraoxa-4,9-diphosphahexacosan-1-aminium, 7-[(hexadecyloxy)methyl]-4,9-dihydroxy-N,N,N-trimethyl-, hydroxide, 4-(inner salt), 4,9-dioxide, (7S) | 25<br>25 | 22<br>8 | | | | 2<br>2 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide, 7(S)-, upper diastereomer | 25<br>25 | STIM<br>95 | | | | 2<br>2 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide, (7R)-, upper diastereomer | 25<br>25 | STIM<br>93 | | | | 2<br>2 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide (7R)-, lower diastereomer | 25<br>25 | 83<br>91 | | | | 2<br>2 |
| 3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-oxide, (7S)-, lower diastereomer | 25<br>25 | 30<br>91 | | | | 2<br>2 |
| 7-(2-Nonadecynyl)-4-hydroxy-N,N,N-trimethyl-3,5,9-trioxa-4-phosphapentacosan-1-aminium, hydroxide, inner salt, 4-oxide | 25<br>25 | 65<br>STIM | | | | 2<br>2 |
| 7-(2,3-Dioxononadecyl)-4-hydroxy-N,N,N-trimethyl-3,5,9-trioxa-4-phosphapentacosan-1-aminium, hydroxide, inner salt, 4-oxide | 25<br>25 | 25<br>STIM | | | | 2<br>2 |
| 3,5,8,10-Tetraoxa-4,9-diphosphapentadecan-1-aminium, 4-hydroxy-9-methoxy-N,N,N-trimethyl-7-[(pentyloxy)-methyl]-, hydroxide, inner sale, 4,9-dioxide | 25<br>25 | STIM<br>STIM | | | | 2<br>2 |
| 3,5,8,10-Tetraoxa-4,9-diphosphapentadecan-1-aminium, 4,9-dihydroxy-N,N,N-trimethyl-7-[(pentyloxy)-methyl]-, hydroxide, | 25<br>25 | STIM<br>STIM | | | | 2<br>2 |

TABLE V-continued

| Compound | MPLA$_2$ Dose μ/ml | % Inh. | Avg. | IC$_{50}$ μ/ml | Avg. | Subs. con. |
|---|---|---|---|---|---|---|
| inner salt, 4,9-dioxide | | | | | | |
| 7-(2-Aminooctadecyl)-4-hydroxy- | 10 | 97 | 65 | | | 2 |
| N,N,N-trimethyl-3,5,9-trioxa-4- | 10 | 34 | | | | 2 |
| phosphapentacosanaminium, | 20 | 98 | 85 | | | 2 |
| hydroxide, inner salt, 4-oxide | 20 | 72 | | | | 2 |
| | 25 | 92 | | | | 2 |
| | 25 | STIM | | | | 2 |
| 3,5,8,10-Tetraoxa-4,9-diphospha- | 25 | 33 | | | | 2 |
| pentadecan-1-aminium, 7-[(hexa- | 25 | STIM | | | | |
| decyloxy)methyl]-4-hydroxy-9- | | | | | | |
| methoxy-N,N,N-trimethyl-, hy- | | | | | | |
| droxide, 4-(inner salt), 4,9- | | | | | | |
| dioxide, less polar isomer | | | | | | |
| 3,5,8,10-Tetraoxa-4,9-diphos- | 25 | 61 | | | | |
| phapentadecan-1-aminium, | 25 | STIM | | | | |
| 7-[(hexadecyloxy)methyl]-4- | | | | | | |
| hydroxy-9-methoxy-N,N,N- | | | | | | |
| trimethyl-, hydroxide, 4-(inner | | | | | | |
| salt), 4,9-dioxide, more | | | | | | |
| polar isomer | | | | | | |
| 3,5,8,10-Tetraoxa-4,9-diphos- | 25 | STIM | | | | |
| phapentadecan-1-aminium, | 25 | 100 | | | | |
| 7-[(hexadecyloxy)methyl]-4,9- | | | | | | |
| dihydroxy-N,N,N-trimethyl-, | | | | | | |
| hydroxide, 4-(inner salt), | | | | | | |
| 4,9-dioxide | | | | | | |
| 3,5,9-Trioxa-4-phosphapentacosan- | 25 | 80 | | | | |
| 1-aminium, 7-(3,3-difluoro-2- | 25 | STIM | | | | |
| methylenenonadecyl)-4-hydroxy- | | | | | | |
| N,N,N-trimethyl-, hydroxide, | | | | | | |
| inner salt, 4-oxide | | | | | | |
| 3,5,9-Trioxa-4-phosphapentacosan- | 10 | 88 | | | | |
| 1-aminium, 7-(3,3-difluoro-2-oxo- | 20 | 89 | | | | |
| nonadecyl)-4-hydroxy-N,N,N-tri- | 25 | 80 | | | | |
| methyl-, hydroxide, inner salt, | 25 | STIM | | | | |
| 4-oxide | | | | | | |
| 3,5,9-Trioxa-4-phosphapentacosan- | 25 | 82 | | | | |
| 1-aminium, 7-(3,3-difluoro-2- | 25 | STIM | | | | |
| hydroxynonadecyl)-4-hydroxy- | | | | | | |
| N,N,N-trimethyl-, hydroxide, | | | | | | |
| inner salt, 4-oxide | | | | | | |
| 7-(2-Aminobutyl)-4,7-dihydroxy- | 10 | 25 | | 19.2 | | |
| N,N,N-trimethyl-3,5,9-trioxa-4- | 20 | 61 | | | | |
| phosphapentacosan-1-aminium, | | | | | | |
| hydroxide, inner salt, 4-oxide | | | | | | |
| (2R)-2-[[[(2-Hexadecyl-4-oxo-2- | 10 | STIM | | | | |
| azetidinyl)methoxy]hydroxyphos- | 20 | STIM | | | | |
| phinyl]oxy]-N,N,N-trimethyl-, | | | | | | |
| hydroxide, inner salt, 4-oxide | | | | | | |
| 3,5,9-Trioxa-4-phosphapentacosan- | 10 | 52 | | 4.9 | | |
| 1-aminium, 7-[(bromoacetyl)oxy]-4- | 20 | 85 | | | | |
| hydroxy-N,N,N-trimethyl-, hydrox- | | | | | | |
| ide, inner salt, 4-oxide | | | | | | |
| 7-[(Chloroacetyl)oxy]-4-hydroxy- | 10 | 46 | | 9.7 | | |
| N,N,N-trimethyl-3,5,9-trioxa-4- | 20 | 72 | | | | |
| phosphapentacosan-1-aminium, | | | | | | |
| hydroxide, inner salt, 4-oxide | | | | | | |
| 10-Bromo-7-[(hexadecyloxy)methyl]- | 10 | 82 | | 1.5 | | |
| 4-hydroxy-N,N,N-trimethyl-9-oxo- | 20 | 82 | | | | |
| 3,5,8-trioxa-4-phosphahexacosan-1- | | | | | | |
| aminium, hydroxide, inner salt, | | | | | | |
| 4-oxide | | | | | | |
| 7-[(Hexadecylsulfinyl)methyl]-4- | 10 | 71 | | 2.9 | | |
| hydroxy-N,N,N-trimethyl-3,5,9- | 20 | 84 | | | | |
| trioxa-4-phosphapentacosan-1- | 25 | 98 | | | | |
| aminium, hydroxide, inner salt | 25 | 84 | | | | |
| 4-oxide | | | | | | |

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to this invention are prepared so that an oral dosage unit contains between about 1 and 250 mg of active compound.

The tablets, capsules and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to active ingredient, sucrose as a sweetening agent, methyl and propylparabens as preservatives, a dye and flavoring such as cherry or orange flavor.

These active compounds may also be administered parenterally. Solutions or suspensions of these active compounds can be prepared in water sutably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing for example, water, ethanol, polyol (e.g. glycerol, propylene glycol and liquid polyethylene glycol), suitable mixtures thereof, and vegetable oils.

The invention will be further described by the following examples.

EXAMPLE 1

2-[(Hexadecyloxylmethyl]-2-propenoic acid, ethyl ester

To a mixture of 1.1 g of 1-hexadecanol and 400 mg of 2-[(acetyloxy)methyl]-2-propenoic acid, ethyl ester in 15 ml of dichloromethane is added 550 mg of dimethylaminopyridine. This mixture is stirred overnight, then the solvent is evaporated and the residue subjected to preparative tlc (25% ethyl acetate/petroleum ether), to give 324 mg of the desired compound.

EXAMPLE 2

3-(Hexadecyloxy)-2-[(hexadecylthio)methyl]propanoic acid, ethyl ester

To a solution of 20 g of 2-[(hexadecyloxy)methyl]-2-propenoic acid, ethyl ester and 10 ml of triethylamine in 60 ml of ethanol is added 53 ml of hexadecyl mercaptan. This mixture is stirred overnight, then the solvents removed and the residue purified by HPLC [hexane:ethyl acetate (9:1)], to give 32.9 g of the desired compound as a white waxy solid.

EXAMPLE 3

3-(Hexadecyloxy)-2-[(hexadecylthio)methyl]-1-propanol

To a slurry of 1.04 g of lithium borohydride in 20 ml of tetrahydrofuran is added 29 g of 3-(hexadecyl-oxy)-2-[(hexadecylthio)methyl]propanoic acid, ethyl ester. This mixture is refluxed overnight, poured into water and purified by chromatography on silica gel [hexane:ethyl acetate (30:1)], to give 18.4 g of the desired compound.

EXAMPLE 4

2-Bromoethyl-3-(hexadecyloxy)-2-[(hexadecylthio)methyl]phosphoric acid, propyl ester To a stirred solution of 15.0 g of 3-(hexadecyloxy)-2-[(hexadecylthio)methyl]-1-propanol and 9.6 g of 2-bromoethyl phosphorochloridate in 100 ml of carbon tetrachloride is added 5.7 ml of triethylamine. This mixture is stirred for 3 hours, then filtered through diatomaceous earth and the solvents evaporated. The residue is dissolved in 25 ml of tetrahydrofuran, 100 ml of 2.5M aqueous sodium acetate added and this mixture is stirred overnight. Dilute aqueous hydrochloric acid and brine are added and this solution was extracted with ethyl acetate, to give 18.3 g of the desired product, mp. 48°–50° C.

EXAMPLE 5

7-[(Hexadecylthio)methyl]-4-hydroxy-N,N,N-trimethyl-3 trioxa-4-phosphapentacosan-1-aminium, hydroxide, inner salt, 4-oxide A mixture of 25.76 g of 2-bromoethyl-3-(hexadecyloxy)-2-[(hexadecylthio)methyl]phosphoric acid, propyl ester, 200 ml of acetonitrile, 150 ml of chloroform and 173 ml of trimethylamine is heated at 60° C. overnight. The solvent is evaporated, 150 ml of methanol, 4.0 g of silver carbonate and 3.0 g of ion exchange resin are added and this mixture is stirred for 2 hours, filtered and the solvent evaporated. The residue is purified by chromatography, to give 8.5 g of the desired compound as a white solid.

EXAMPLE 6

3-(Hexadecylthio)propanoic acid, ethyl ester

A mixture of 17.7 ml of hexadecyl mercaptan, 3.0 g of ethyl acrylate and 2 ml of triethylamine is stirred overnight, the solvent evaporated and the residue purified by HPLC, to give 19.99 g of the desired compound as a white solid.

EXAMPLE 7

3-(Hexadecylthio)-1-propanol

To a slurry of 147.4 mg of lithium borohydride in ml of tetrahydrofuran is added 2.4 g of 3-(hexadecylthio)propanoic acid, ethyl ester. This mixture is refluxed overnight, poured into water and extracted with ethyl acetate, to give 2.1 g of the desired compound.

EXAMPLE 8

2-Bromoethyl-3-(hexadecylthio)phosphoric acid, propyl ester

To a stirred solution of 2.0 g of 3-(hexadecylthio)-1-propanol and 2.7 g of 2-bromoethyl phosphorochloridate in 25 ml of carbon tetrachloride is added 1.6 ml of triethylamine. This solution is stirred for 3 hours, filtered through diatomaceous earth and the solvent evaporated. A 25 ml portion of tetrahydrofuran and 25 ml of aqueous 2.5M sodium acetate are added to the residue. This mixture is stirred overnight, dilute aqueous hydrochloric acid and brine are added and the solution is extracted with ethyl acetate, to give 3.0 g of the desired compound, mp. 46°–49° C.

EXAMPLE 9

7-[(Hexadecylsulfonyl)methyl]-4-hydroxy-N,N,N-trimethyl-3,5,9-trioxa-4-phosphapentacosan-1-aminium, hydroxide, inner salt, 4-oxide A solution of 200 mg of 7-[(hexadecylthio)methyl]-4-hydroxy-N,N,N-trimethyl-3,5,9-trioxa-4- phosphapentacosan-1-aminium, hydroxide, inner salt, 4-oxide in chloroform:methanol (1:1) is subjected to ozonolysis at −12° C. at 96 volts and a flow rate of 0.5 ml per minute for 25 minutes, to give 204 mg of the desired compound.

EXAMPLE 10

7-[(Hexadecylsulfinyl)methyl]-4-hydroxy-N,N,N-trimethyl-3,5,9-trioxa-4-phosphapentacosan-1-aminium, hydroxide, inner salt, 4-oxide To a solution of 1.0 g of 7-[(hexadecylthio)methyl]-4-hydroxy-N,N,N-trimethyl-3,5,9-trioxa-4-phosphapentacosan-1-aminium, hydroxide, inner salt, 4-oxide in 5 ml of dichloromethane is added a solution of 323 mg of m-chloroperbenzoic acid in 3 ml of dichloromethane. This mixture is stirred overnight, then evaporated and the residue purified by chromatography, to give 1.05 g of the desired compound as a white waxy solid.

EXAMPLE 11

4-Hydroxy-N,N,N-trimethyl-3,5-dioxa-9-thia-4-phosphapentacosan-1-aminium, hydroxide, inner salt, 4-oxide A mixture of 3.0 g of 2-bromoethyl-3-(hexadecylthio)phosphoric acid, propyl ester, 36 ml of acetonitrile, 33 ml of chloroform and 20 g of trimethylamine is heated overnight at 60° C. and then evaporated. To the residue is added 35 ml of methanol, 1.0 g of silver carbonate and 1.0 g of ion exchange resin. This mixture is stirred for 2 hours, filtered and the solvent evaporated. The residue is purified by chromatography, to give 1.5 g of the desired compound as a white solid.

EXAMPLE 12

4-Hydroxy-N,N,N-trimethyl-3,5-dioxa-9-thia-4-phosphapentacosan-1-aminium, hydroxide, inner salt, 4.9.9-trioxide To a solution of 400 mg of 4-hydroxy-N,N,N-trimethyl-3,5-dioxa-9-thia-4-phosphapentacosan-1-aminium, hydroxide, inner salt, 4-oxide in 10 l of dichloromethane containing two drops of methanol is added 174 mg of m-chloroperbenzoic acid in 3 ml of dichloromethane. The solution is stirred overnight, then evaporated and the residue subjected to chromatography, to give 414 mg of the desired compound as a white wax.

EXAMPLE 13

4-Hydroxy-N,N,N-trimethyl-3,5-dioxa-9-thia-4-phosphapentacosan-1-aminium, hydroxide, inner salt, 4.9-dioxide To a solution of 192.4 mg of 4-hydroxy-N,N,N-trimethyl-3,5-dioxa-9-thia-4-phosphapentacosan-1-aminium, hydroxide, inner salt, 4-oxide in 5 ml of chloroform at −78° C. is added a solution of 68 mg of m-chloroperbenzoic acid in 5 ml of chloroform. This mixture is allowed to warm to room temperature then evaporated. The residue is purified by chromatography, to give 173 mg of the desired compound as a white wax.

EXAMPLE 14

2-[(Hexadecyloxy)methyl]-3-(phenylmethoxy)-4-methylbenzenesulfonate-1-propanol

To a solution of 23 g of 3-[(hexadecyloxy)methyl]-4-(phenylmethoxy)-butanol and 25 ml of triethylamine in 50 ml of dichloromethane at 0° C., is added 11.633 g of p-toluenesulfonyl chloride in 20 ml of dichloromethane. This solution is stirred overnight and then poured into water. The organic layer is separated, then evaporated and purified by chromatography, to give 31 g of the desired compound as a dark yellow oil.

EXAMPLE 15

[[(3-Hexadecyloxy)-2-(iodomethyl)propoxylmethyl]-benzene

A mixture of 5.3g of 3-[(hexadecyloxy)methyl]-4-(phenylmethoxy)-4-toluenesulfonyloxybutane, 4.2 g of sodium iodide and 50 ml of acetone is stirred at reflux for 2 days, then poured into water and extracted with dichloromethane. The extract is washed with saturated aqueous sodium bisulfite, dried and evaporated. The residue is purified by chromatography, to give 3.5 g of the desired compound as a light yellow oil.

EXAMPLE 16

2-[(Hexadecyloxy)methyl]-3-(phenylmethoxy)propyl]-phosphonic acid, diethyl ester To 20 mg of washed sodium in 3 ml of toluene under nitrogen is added 0.118 ml of diethyl phosphite. This mixture is stirred for 2 hours, then heated to 80° C. for 30 minutes, giving a clear solution. To this solution is added 200 mg of [[(3-hexadecyloxy)-2-(iodomethyl)-propoxy]methyl]benzene in 1 ml of toluene at 80° C. This mixture is heated at 80° C. overnight, then the solvent is evaporated. Water and ether are added to the residue. The ether layer is separated, dried and evaporated. This residue is purified by chromatography, giving 117 mg of the desired compound as a clear oil.

EXAMPLE 17

[3-(Hexadecyloxy)-2-(hydroxymethyl)propyl]phosphonic acid, diethyl ester

A 7.7 g portion of 2-[(hexadecyloxy)methyl]-3-(phenylmethoxy)propyl]phosphonic acid, diethyl ester is hydrogenated over 500 mg of 10% palladium-on-carbon in 20 ml of methanol and 20 ml of acetic acid, to give 6.5 g of the desired compound.

EXAMPLE 18

2-Bromomethyl-3-(diethoxyphosphinyl)-2-((hexadecyloxy) methyl]phosphoric acid, propyl ester To 5.0 g of [3-(hexadecyloxy)-2-(hydroxymethyl) propyl]phosphonic acid, diethyl ester in 50 ml of carbon tetrachloride is added 5.0 g of 2-bromomethyl phosphorodichloridate, followed by 3 ml of triethylamine. This mixture is stirred for 2.5 hours, then filtered through diatomaceous earth and the solvent evaporated. The residue is mixed with 50 ml of tetrahydrofuran and 50 ml of aqueous 0.5N sodium acetate and stirred overnight. Dilute hydrochloric acid, brine and ethyl acetate are added. The organic layer is separated, dried and evaporated, to give 6.8 g of the desired compound as a yellow oil.

EXAMPLE 19

9-Ethoxy-7-[(hexadecyloxy)methyl]-N,N,N-trimethyl-4-hydroxy-3,5,10-trioxa-4,9-diphosphadodecan-1-aminium. hydroxide, inner salt, 4,9-dihydroxide A mixture of 6.8 g of 2-bromoethyl-3-(diethoxyphosphinyl)-2-[(hexadecyloxy)methyl]phosphoric acid, propyl ester, 30 ml of acetonitrile, 30 ml of chloroform and 5.0 g of trimethylamine is mixed in a glass bomb and heated overnight at 60° C. The solvent is evaporated, 100 ml of methanol and 1.0 of silver carbonate added and this mixture stirred at room temperature for 2 hours. The mixture is filtered through diatomaceous earth and then evaporated, to give a white solid which is purified by chromatography to yield 4.4 of the desired compound as a white wax.

EXAMPLE 20

2-[(Hexadecyloxy)methyl]-2-propen-1-ol

To 18.5 g of washed sodium hydride in 500 ml of dry dimethylformamide in a water bath is added dropwise, 67.4 g of 2-butene-1,2-diol. A solution of 235 g of hexadecylbromide in 100 ml of dimethylformamide is added dropwise. This mixture is stirred at room temperature for 2 days then poured into water and extracted with ether. The ether extract is separated, dried, evaporated and purified by chromatography, to give 30 g of the desired compound.

EXAMPLE 21

(1,1-Dimethylethyl)[[2-[(hexadecyloxy)methyl]-2-propenyl]oxy]dimethylsilane

To a solution of 5.0 g of 2-[(hexadecyloxy)-methyl]-2-propen-1-ol in 50 ml of dry N,N-dimethylformamide is added 6.05 g of tert-butyldimethylsilyl chloride followed by 8 g of imidazole. This mixture is stirred overnight, then diluted with ether, washed with saturated aqueous sodium bicarbonate, water and brine, dried and evaporated, to give 6.49 g of the desired compound.

EXAMPLE 22

5-[[[(1,1-Dimethylethyl)dimethylsilyl]oxy]methyl]-3-ethyl-5-[(hexadecyloxy)methyl]-4,5-dihydroisoxazole To a solution of 2.0 g of (1,1-dimethylethyl)[[2-[(hexadecyloxy)methyl]-2-propenyl]oxy]dimethylsilane, 623 mg of propyl nitrite and 3 ml of triethylamine in a water bath is slowly added a solution of 1.07 g of phosphorous oxychloride in 2 ml of chloroform. This solution is warmed to room temperature, stirred overnight, then poured into water, dichloromethane and brine. The organic layer is separated, dried and evaporated. The residue is subjected to flash chromatography, to give 1.0 g of the desired compound.

EXAMPLE 23

(S)-3-Ethyl-4,5-dihydro-5-[(hexadecyloxy)methyl]-5-isoxazolemethanol

To a solution of 500 mg of 5-[[[(1,1-dimethylethyl)-dimethylsilyl]oxy]methyl]-3-ethyl-5-[(hexadecyloxy)-methyl]-4,5-dihydroisoxazole in 10 ml of tetrahydrofuran is added 2.13 ml of 1M tetrabutylammonium fluoride in tetrahydrofuran. After 2 hours the reaction is poured into water, ether and brine. The organic layer is separated, dried and evaporated, to give 300 mg of the desired compound.

EXAMPLE 24

(5S)-2-[[[[3-Ethyl-5-[(hexadecyloxy)methyl]-4,5-dihydro-5-isoxazolyl]methoxy]hydroxyphosphinyl]oxy]-N,N,N-trimethylethanaminium, hydroxide, inner salt To a solution of 1.1 g of (S)-3-ethyl-4,5-dihydro-5-[(hexadecyloxy)methyl]-5-isoxazolemethanol in 15 ml of dry carbon tetrachloride under argon is added 1.02 g of 2-bromoethyl phosphorochloridate and 5 ml of triethylamine. This mixture is stirred for 2 hours, filtered through diatomaceous earth and the solvent evaporated. To the residue is added 5 ml of tetrahydrofuran and 5 ml of 0.5N aqueous sodium acetate. This mixture is stirred overnight. Dilute hydrochloric acid and ethyl acetate are added, the organic layer separated, washed with brine, dried and evaporated. The residue is placed in a bomb with 21 ml of acetonitrile, 21 ml of chloroform and 20 g of trimethylamine and heated at 65° C. for 5 hours. The solvents are evaporated. Methanol and silver carbonate are added, the mixture stirred for 2 hours, filtered and evaporated, to give, after chromatography, 900 mg of the desired compound.

EXAMPLE 25

7-(2-Aminobutyl)-4,7-dihydroxy-N,N,N-trimethyl-3,5,9-trioxa-4-phosphapentacosan-1-aminium, hydroxide, inner salt, 4-oxide A mixture of 500 mg of (5S)-2-[[[[3-ethyl-5-[(hexadecyloxy)methyl]-4,5-dihydro-5-isoxazolyl]methoxy]-hydroxyphosphinyl]oxy]-N,N,N-trimethylethanaminium, hydroxide, inner salt, 50 mg of 10% palladium-on-carbon and 15 ml of methanol is hydrogenated for 20 hours, then filtered and evaporated, to give 500 mg of the desired compound as a clear oil.

EXAMPLE 26

2-[(Phenylmethoxy)methyl]-1-octadecene

To 1.4 g of washed sodium hydride in 100 ml of dry N,N-dimethylformamide is added a solution of 10 g of 1-octadecenol in 100 ml of dimethylformamide followed by 5.8 g of benzyl bromide. This mixture is stirred for 15 hours, then water added and the mixture extracted with ether. The ether extract is dried, evaporated and purified by chromatography, to give 9.0 g of the desired compound.

EXAMPLE 27

(R)-4-Hexadecyl-4-[(phenylmethoxy)methyl]-2-azetidinone

To a solution of 3.0 g of 2-[(phenylmethoxy)methyl]-1-octadecene in 10 ml of benzene under argon is added 1.05 ml of chlorosulfonyl isocyanate. The mixture is stirred overnight and then poured into a solution of 22 g of sodium bisulfite, 100 ml of water, 5 ml of 10% sodium hydroxide and 100 ml of ether. This mixture is stirred for 2 hours, and the organic layer separated, dried and evaporated. The residue is purified by chromatography, to give 1.1 g of the desired compound as a colorless oil.

EXAMPLE 28

(R)-4-Hexadecyl-4-(hydroxymethyl)-2-azetidinone

A mixture of 400 mg of (R)-4-hexadecyl-4-[(phenylmethoxy)methyl]-2-azetidinone, 50 mg of 10% palladium-on-carbon and 20 ml of methanol:acetic acid (1:1) is hydrogenated for 16 hours, then filtered and evaporated. The residue is recrystallized from petroleum ether/ethyl acetate, to give 300 mg of the desired compound as a white solid, mp. 82° C.

EXAMPLE 29

(2R)-2-[[[(2-Hexadecyl-4-oxo-2-azetidinyl)methoxy]hydroxyphosphinyl]oxy]-N,N,N-trimethylethanaminium, hydroxide, inner salt To a mixture of 265 mg of (R)-4-hexadecyl-4-(hydroxymethyl)-2-azetidinone and 86 mg of triethylamine in 4 ml of dry benzene at 0° C. under argon is added 121 mg of 2-chloro-2-oxo-1,3,2-dioxaphospholine. The mixture is warmed to room temperature, stirred overnight, filtered through diatomaceous earth and evaporated. The residue is dissolved in 15 ml of dry acetonitrile, 1 ml of trimethylamine is added and this mixture placed in a bomb and heated overnight at 65° C. The product is purified by chromatography, to give 90 mg of the desired compound as a white solid.

EXAMPLE 30

2-Nonadecyn-1-ol

A mixture of 56.1 g of propargyl alcohol in 100 ml of tetrahydrofuran and 15.6 g of lithium in 1 liter of ammonia containing a trace of ferric chloride is stirred for 1 hour. A 76.4 ml portion of hexadecyl bromide is added and the mixture refluxed for 8 hours then evaporated. The residue is dissolved in ether and washed with 10% hydrochloric acid, dried and purified by flash chromatography, to give 47.4 g of the desired compound as white platelets, mp. 60° C.

EXAMPLE 31

1-Bromo-2-nonadecyne

A mixture of 18.8 g of 2-nonadecyn-1-ol, 110 ml of ether, 1.14 ml of pyridine and 5.7 ml of phosphorous tribromide in 25 ml of ether is heated at reflux for 2 hours, then stirred at room temperature for 2 hours, poured into water and washed with hydrochloric acid. The solution is evaporated and filtered through silicon dioxide with hexane, to give 16.9 g of the desired product as a white solid, mp. 34°-35° C.

EXAMPLE 32

2-Nonadecyvylpropanedioic acid, diethyl ester

A mixture of 16.5 g of 1-bromo-2-nonadecyne in 50 ml of ethanol is added to 3.0 g of 60% sodium hydride and 11.4 ml of diethyl malonate in 100 ml of ethanol. This mixture is stirred one hour and then evaporated. The residue is washed with ether, twice with dilute hydrochloric acid and brine. The residue is then purified by flash chromatography, (5% ethyl acetate:petroleum ether), to give 12.1 g of the desired compound as white needles, mp. 33°-34° C.

EXAMPLE 33

2-(2-Nonadecynyl)-1,3-propanediol

A mixture of 1.8 g of lithium aluminum hydride in 150 ml of ether is prepared at 0° C. To this is added a solution of 11.7 g of 2-nonadecynylpropanedioic acid, diethyl ester in ether. This mixture is refluxed for 4 hours then the reaction is quenched with aqueous sodium sulfate. After stirring for 2 days, the reaction is diluted with ethyl acetate and filtered. The residue is treated with methanol, 1N sodium hydroxide and tetrahydrofuran and then evaporated. The residue is dissolved in ether and washed with brine and purified by flash chromatography, (4:6 ethyl acetate:petroleum ether), to give 5.3 g of the desired product as white plates, mp. 55° C.

EXAMPLE 34

2-[(Hexadecyloxy)methyl]-4-heneicosyn-1-ol

A mixture of 5.0 g of 2-(2-nonadecynyl)-1,3-propanediol, 75 ml of N,N-dimethylformamide, 710 mg of 60% sodium hydride and 5.4 ml of hexadecyl bromide is heated at 70° C. for 2 hours and then evaporated. The residue is purified by flash chromatography with an ethyl acetate:petroleum ether gradient to give 5.8 g of the desired compound as white crystals, mp. 46°-47° C.

EXAMPLE 35

7-(2-Nonadecynyl)-4-hydroxy-N,N,N-trimethyl-3,5,9-trioxa-4-phosphapentacosan-1-aminium, hydroxide, inner salt, 4-oxide A mixture of 4.0 g of 2-[(hexadecyloxy)methyl]-4-heneicosyn-1-ol, 50 ml of carbon tetrachloride, 1.6 ml of triethylamine and 1.38 ml of 2-bromoethyl phosphorochloridate is stirred for 4 hours at room temperature and the solvent evaporated. The residue is diluted with 100 ml of tetrahydrofuran and 100 ml of 0.5M sodium acetate and stirred overnight, then evaporated. This residue is acidified and extracted three times with ether. The extracts are combined, evaporated and the residue added to a mixture of 50 ml of chloroform, 50 ml of acetonitrile and 25 g of trimethylamine. The mixture is heated at 60° C. for 4.5 hours, then evaporated and purified by flash chromatography (3:7 methyl alcohol: chloroform with 5% water), to give 4.2 g of the desired compound as an amorphous solid.

EXAMPLE 36

7-(2,3-Dioxononadecyl)-4-hydroxy-N,N,N-trimethyl-3,5,9- trioxa-4-phosphapentacosan-1-aminium, hydroxide, inner salt, 4-oxide A mixture of 500 mg of 7-(2-nonadecynyl)-4- hydroxy-N,N,N-trimethyl-3,5,9-trioxa-4-phosphapentacos-an-aminium, hydroxide, inner salt, 4-oxide, 5 ml of dichloromethane and 0.25 ml of acetic acid is heated at reflux. A 100 mg portion of tricaprylylmethyl ammonium chloride is added followed by 500 mg of ground potassium permangamate. The reaction is heated at reflux for 1 hour. The crude reaction mixture is subjected to flash chromatography (3:7 methyl alcohol:chloroform with 5% water) to give 135 mg of the desired compound as a yellow amorphous solid.

EXAMPLE 37

2-Methylene-1-octadecanol

This compound is prepared by the process of Marshall, Journal of Organic Chemistry, 32, 113 (1967).

EXAMPLE 38

2-(Bromomethyl)-1-octadecene

A mixture of 20 g of 2-methylene-1-octadecanol, 150 ml of ether and 12.6 ml of pyridine is cooled to −15° C. in an ice-methanol bath. A solution of 7.3 ml of phosphorous tribromide in 50 ml of ether is added slowly over 1 hour, and the mixture is allowed to warm to room temperature overnight. The mixture is recooled to 0° C., 1.9 ml of water added and then allowed to warm to room temperature over 6 hours. The mixture is washed, filtered and evaporated, to give 19.2 g of the desired compound as a clear oil.

EXAMPLE 39

2-(Methyleneoctadecyl)propanedioic acid, diethyl ester

A mixture of 3.7 g of 50% sodium hydride, 100 ml of tetrahydrofuran and 10.1 ml of diethylmalonate is cooled with a water bath. A solution of 19.2 g of 2-(bromomethyl)-1-octadecene in 50 ml of tetrahydrofuran is added dropwise and this mixture stirred overnight at room temperature. A 2.6 g portion of 50% sodium hydride is added and the mixture refluxed overnight, then diluted with ether and washed with dilute hydrochloric acid, water and brine. Flash chromatography (5% ethyl acetate:hexane) gives 8.52 g of the desired compound as a clear oil.

EXAMPLE 40

2-(2-Methyleneoctadecyl)-1,3-propanediol

A solution of 1.03 g of lithium aluminum hydride in 50 ml of ether is cooled in a water bath. A mixture of 6.78 g of 2-(methyleneoctadecyl)propanedioic acid, diethyl ester in 50 ml of ether is added. This mixture is stirred at reflux for 2 hours, then overnight at room temperature and finally at reflux for 4 hours. The mixture is stirred with sodium sulfate decahydrate, then filtered and recrystallized from ethyl acetate/hexane, to give 4.87 g of the desired compound as white crystals, mp. 64°-65° C.

EXAMPLE 41

2-[(Hexadecyloxy)methyl]-4-methylene-1-eicosanol

A solution of 80 mg of 60% sodium hydride in 20 ml of N,N-dimethylformamide is stirred at room temperature. A 680 mg portion of 2-(2-methyleneoctadecyl)-1,3-propanediol and 0.61 ml of hexadecylbromide are added and the mixture warmed very slowly to 60°-70° C. The mixture is evaporated, dissolved in ether, and is washed with water and brine then flash chromatographed (5% ethyl acetate:petroleum ether), to give 550 mg of the desired compound as colorless crystals, mp. 37°-38° C.

EXAMPLE 42

4-Hydroxy-N,N,N-trimethyl-7-(2-methyleneoctadecyl)-3,5,9-trioxa-4-phosphaoentacosan-1-aminium, hydroxide, inner salt, 4-oxide A mixture of 10.2 g of 2-[(hexadecyloxy)methyl]-4-methylene-1-eicosanol, 100 ml of carbon tetrachloride, 4.0 ml of triethylamine and 6.41 g of 2-bromoethyl phosphorodichloridate is stirred for 3 hours, then filtered and evaporated. To the residue is added 200 ml of tetrahydrofuran and 200 ml of 0.5M aqueous sodium acetate. This mixture is stirred for 2 hours, the tetrahydrofuran evaporated and the residue acidified with hydrochloric acid and extracted with ether. The extract is dried and evaporated. The residue is combined with 150 ml of acetonitrile, 150 ml of chloroform and 50 g of trimethylamine and refluxed for 4 hours. The solution is evaporated and the residue stirred with 200 ml each of methanol and tetrahydrofuran and 2.5 g of silver carbonate for 90 minutes, then filtered and evaporated. The residue is purified by flash chromatography (30% methyl alcohol:chloroform up to 5% water:30% methyl alcohol:chloroform), to give 10.1 g of the desired compound as an amorphous white solid.

EXAMPLE 43

4-Hydroxy-N,N,N-trimethyl-7-(2-oxooctadecyl)-3,5,9-trioxa-4-phosphapentacosan-1-aminium, hydroxide inner salt, 4 oxide A mixture of 5.0 g of 4-hydroxy-N,N,N-trimethyl-7-(2-methyleneoctadecyl)-3,5,9-trioxa-4-phosphapentacosan-1-aminium, hydroxide, inner salt, 4-oxide, 200 ml of chloroform and 22 ml of ethanol is subjected to ozonolysis at −40° C. until the solution turns blue. The reaction is flushed with oxygen, 1.6 ml of trimethyl phosphite added at 0° C. and then evaporated. The residue is purified by flash chromatography (30% methyl alcohol:chloroform up to 5% water:30% methyl alcohol:chloroform), to give 4.0 g of the desired compound as an amorphous white solid.

EXAMPLE 44

7-(2-Aminooctadecyl)-4-hydroxy-N,N,N-trimethyl-3,5,9-trioxa-4-phosphapentacosanaminium, hydroxide, inner salt, 4-oxide A mixture of 200 mg of 4-hydroxy-N,N,N-trimethyl-7-(2-methyleneoctadecyl)-3,5,9-trioxa-4-phosphapentacosan-1-aminium, hydroxide, inner salt, 4-oxide, 2 ml of methanol, 1 ml of chloroform, 300 mg of ammonium acetate and 15 mg of sodium cyanoborohydride is stirred for 36 hours and then evaporated and chromatographed (30% methyl alcohol:chloroform up to 5% water:30% methyl alcohol:chloroform, up to 5% ammonium hydroxide:30% methyl alcohol:chloroform), to give 160 mg of the desired compound as a white amorphous solid.

EXAMPLE 45

4-Hydroxy-7-(2-hydroxy-2-methyloctadecyl)-N,N,N-trimethyl-3,5,9-trioxa-4-phosphapentacosan-1-aminium, hydroxide, inner salt, 4-oxide A mixture of 410 mg of 4-hydroxy-N,N,N-trimethyl-7-(2-oxooctadecyl)-3,5,9-trioxa-4-phosphapentacosan-1-aminium, hydroxide, inner salt, 4-oxide, 10 ml of tetrahydrofuran, 5 ml of toluene and 1.5 ml of hexamethyl phosphoramide is stirred at 0° C. A 1 ml portion of 3M methyl magnesium bromide is added in portions, and the mixture is stirred at room temperature overnight. The mixture is recooled to 0° C., 1 ml of methyl magnesium bromide, 0.6 ml of acetic acid in tetrahydrofuran and an excess of sodium bicarbonate is added sequentially and the mixture is evaporated. The residue is purified by chromatography (3:7 methyl alcohol:chloroform up to 5% water in 3:7 methyl alcohol:chloroform), to give 200 mg of the desired compound as an amorphous white solid.

EXAMPLE 46

7-[(2-Hexadecyloxiranyl)methyl]-4-hydroxy-N,N,N-trimethyl-3,5,9-trioxa-4-phosphapentacosan-1-aminium, hydroxide, inner salt, 4-oxide A mixture of 290 mg of 3-chloroperoxybenzoic acid, 1.3 g of sodium bicarbonate and 15 ml of chloroform is stirred rapidly at 0° C. A 730 mg portion of 4-hydroxy-N,N,N-trimethyl-7-(2-methyleneoctadecyl)-3,5,9-trioxa-4-phosphapentacosan-1-aminium, hydroxide, inner salt, 4-oxide is added and this mixture is stirred at room temperature for 5 hours, then at 0° C. overnight. A 75 ml portion of methyl sulfide is added and the mixture flash chromatographed (3:7 methyl alcohol:chloroform up to 5% water in 3:7 methyl alcohol:chloroform), to give 700 mg of the desired compound as an off-white amorphous solid.

EXAMPLE 47

4-Hydroxy-7-(2-hydroxyoctadecyl)-N,N,N-trimethyl-3,5,9-trioxa-4-phosphapentacosan-1-aminium, hydroxide, inner salt, 4-oxide and isomer A mixture of 732 mg of 4-hydroxy-N,N,N-trimethyl-7-(2-oxooctadecyl)-3,5,9-trioxa-4-phosphapentacosan-1-aminium, hydroxide, inner salt, 4-oxide and 10 ml of chloroform is stirred at 0° C. A 25 ml portion of diborane in tetrahydrofuran is added, and the mixture stirred at room temperature then evaporated. The residue is flash chromatographed (3:7 methyl alcohol:chloroform up to 5% water in 3:7 methyl alcohol:chloroform), to give 210 mg and 150 mg of the respective isomeric forms as white amorphous solids.

EXAMPLE 48

[[3-Azido-2-[(hexadecyloxy)methyl]propoxy]methyl]benzene

A mixture of 16.3 g of 2-[(hexadecyloxy)methyl]-3-(phenylmethoxy)-4-methylbenzenesulfonate-1-propanol, 9.22 g of sodium azide and 130 ml of N,N-dimethylformamide is stirred at 80° C. for 3.5 hours and then at room temperature overnight. The mixture is poured into water and extracted with ether. The ether layer is dried and the solvent removed. The residue is purified by chromatography, to give 8.9 g of the desired compound as an oil.

EXAMPLE 49

2-[(Hexadecyloxy)methyl]-3-(phenylmethoxy)-1-propanamine

To a solution of 0.87 g of lithium aluminum hydride in 80 ml of ether under argon is added, with stirring, over 30 minutes, a solution of 8.5 g of [[3- azido-2-[(hexadecyloxy)methyl]propoxy]methyl]benzene in 80 ml of ether. This mixture is refluxed for 3 hours, then cooled to 0° C. and 8 ml of saturated aqueous sodium sulfate solution is added. The mixture is filtered and the filtrate evaporated, to give 8.0 g of the desired compound as an oil.

EXAMPLE 50

N-[2-[(Hexadecyloxy)methyl]-3-(phenylmethoxy) propyl]octadecanamide

A mixture of 8.0 g of 2-[(hexadecyloxy)methyl]-3-(phenylmethoxy)-1-propanamine, 12.6 g of stearic anhydride, 2.56 g of dimethylaminopyridine and 30 ml of chloroform is stirred overnight, and the solvent evaporated. Ether is added to the residue and this solution washed with dilute hydrochloric acid and saturated aqueous sodium bicarbonate. The solvent is removed and the residue purified by chromatography and then recrystallized from methanol, to give 11.0 g of the desired compound as a white solid, mp. 56°-57° C.

EXAMPLE 51

N-[3-(Hexadecyloxy)-2-hydroxymethyl)propyl]octadecanamide

A mixture of 10.5 g of N-[2-[(hexadecyloxy)methyl]-3-(phenylmethoxy)propyl]octadecanamide, 1.5 g of 5% palladium-on-carbon, 250 ml of cyclohexane and 27 ml of glacial acetic acid is shaken in a Parr apparatus for 24 hours and then filtered. The filtrate is evaporated and the residue recrystallized from methanol, to give 7.9 g of the desired product as a white solid, mp. 74°-75° C.

EXAMPLE 52

7-[(Hexadecyloxy)methyl]-4-hydroxy-N,N,N-trimethyl-10-oxo-3,5-dioxa-9-aza-4-phosphaheptacosan-1-aminium, hydroxide, inner salt, 4-oxide A mixture of 5.0 g of N-[3-(hexadecyloxy)-2-hydroxymethyl)propyl]octadecanamide, 1.31 g of 2-chloro-1,3,2-dioxaphospholane-2-oxide, 1.02 g of triethylamine and 200 ml of ether is stirred overnight, then diluted with more ether and ethyl acetate, washed with brine and dried. The solvent is removed and the residue heated at 65° C. with 50 ml of chloroform, 100 ml of acetonitrile and 60 ml of 33% trimethylamine in acetonitrile in a pressure bottle overnight. An additional 40 ml of trimethylamine is added, the mixture is heated at 70° C. for 30 minutes and then the solvent is removed. The residue is purified by chromatography, to give 2.3 g of the desired compound.

EXAMPLE 53

2-[(Hexadecyloxy)methyl]-4-penten-1-ol

To a suspension of 19.1 g of 50% sodium hydride under argon in 300 ml of N,N-dimethylformamide is added dropwise over a period of 1 hour, with stirring a solution of 37 g of 4-penten-1-ol, 2-methanol (prepared as described by B. K. Wasson, et. al., J. Chem. Soc., 39, 923 (1961)) in 200 ml of tetrahydrofuran. After stirring another 30 minutes, 126.34 g of hexadecyloxytosylate is added followed by 500 ml of tetrahydrofuran. This mixture is stirred for 2.5 hours, then heated to 80° C. for 20 minutes and then at room temperature overnight. Water is added and the mixture extracted with ether. The ether extract is dried and then evaporated. The residue is distilled using a Kugelrohr. The fraction distilling at 200°-210° C. 1 mm is collected, purified by chromatography and then redistilled, to give 11.35 g of the desired compound.

EXAMPLE 54

4-Hydroxy-N,N,N-trimethyl-7-(2-propanyl)-3,5,9-trioxa-4-phosphapentacosan-1-aminium, hydroxide, inner salt, 4-oxide A mixture of 10.3 g of 2-[(hexadecyloxy)methyl]-4-penten-1-ol, 9.14 g of 2-bromoethyl phosphorochloridate, 3.83 g of triethylamine, and 225 ml of carbon tetrachloride is stirred for 10 minutes and then refrigerated overnight. The mixture is stirred with 250 ml of tetrahydrofuran and 250 ml of 0.5M aqueous sodium acetate for 2 hours and most of the tetrahydrofuran is removed. The residue is acidified with hydrochloric acid and extracted with ether. The ether extract is dried and evaporated. The residue is refluxed in a mixture of 150 ml of acetonitrile, 120 ml of chloroform and 50 g of trimethylamine for 4 hours and then evaporated. The residue is dissolved in 200 ml of methanol and stirred with 20 g of ion exchange resin and 2 g of silver carbonate for 1 hour then filtered and evaporated. The residue is purified by chromatography to give 10.2 g of the desired compound as a colorless solid.

EXAMPLE 55

4-Hydroxy-N,N,N-trimethyl-7-(2-oxoethyl)-3,5,9-trioxa-4-phosphapentacosan-1-aminium, hydroxide, inner salt, 4-oxide A solution of 2.0 g of 4-hydroxy-N,N,N-trimethyl-7-(2-propenyl)-3,5,9-trioxa-4-phosphapentacosan-1-aminium, hydroxide, inner salt, 4-oxide in 35 ml of methanol and 25 ml of dichloromethane is stirred at −78° C. as ozone was bubbled through for 30 minutes. The mixture is allowed to warm to −40° C., then re-cooled to −78° C. and 0.98 g of trimethylphosphite is added. The mixture is allowed to warm to room temperature and the solvent removed. The residue is purified by chromatography, to give 1.0 g of the desired compound as a white powder.

EXAMPLE 56

4-Hydroxy-7-[2-(hydroxyimino)ethyl]-N,N,N-trimethyl-3,5,9-trioxa-4-phosphaoentacosan-1-aminium, hydroxide, inner salt, 4-oxide A mixture of 0.45 g of 4-hydroxy-N,N,N-trimethyl-7-(2-oxoethyl)-3,5,9-trioxa-4-phosphapentacosan-1-aminium, hydroxide, inner salt, 4-oxide, 0.12 g of hydroxylamine hydrochloride, 0.055 g of sodium carbonate, 6 ml of ethanol and 3 ml of water is stirred for 40 minutes and then refrigerated overnight. Another 0.12 g of hydroxylamine hydrochloride and 0.05 g of sodium carbonate are added and the mixture stirred for 4 hours. The mixture is diluted with ethanol, passed through a column of ion exchange resin and the solvent removed. The residue is dissolved in chloroform, filtered through diatomaceous earth and evaporated. The residue is triturated with ether and the solid collected, to give 0.45 g of the desired compound as a hydroscopic white powder.

EXAMPLE 57

4-Hydroxy-N,N,N-trimethyl-7-(oxiranylmethyl)-3,5,9-trioxa-4-phosphapentacosan-1-aminium, hydroxide, inner salt, 4-oxide A mixture of 3.0 g of 4-hydroxy-N,N,N-trimethyl-7-(2-propenyl)-3,5,9-trioxa-4-phosphapentacosan-1-aminium, hydroxide, inner salt, 4-oxide, 2.25 g of m-chloroperbenzoic acid and 30 ml of dichloromethane is stirred for 24 hours and then refrigerated for 18 hours. The solvent is removed and the residue purified by chromatography, then triturated with ether, to give 1.8 g of the desired compound as a white powder.

EXAMPLE 58

2-[[Hydroxy[(2-methylenenonadecyl)oxy]phosphinyl]oxy]-N,N,N-trimethylethaniminium, hydroxide, inner salt To a solution of 3.8 g of 2-[(hexadecyloxy)methyl]-2-propen-1-ol in 100 ml of carbon tetrachloride is added 3.91 g of 2-bromoethyl phosphorochloridate and 1.64 g of triethylamine. The mixture is stirred overnight in a refrigerator, then filtered and the solvent removed. A 100 ml portion of 0.5M aqueous sodium acetate and 100 ml of tetrahydrofuran are added and this mixture stirred for 1 hour. The tetrahydrofuran is removed, the mixture acidified with sulfuric acid and extracted with ether. The ether extract is washed with brine, dried and evaporated. The residue is stirred at reflux in 60 ml of acetonitrile, 50 ml of chloroform and 20 g of trimethylamine for 4 hours, then evaporated. The residue is stirred in 100 ml of methanol containing 10 g of ion exchange resin and 1.0 g of silver carbonate, then filtered and the solvent removed. This residue is purified by chromatography, to give 2.4 g of the desired compound as a white solid.

EXAMPLE 59

7-(Boronomethyl)-4-hydroxy-N,N,N-trimethyl-3,5,9-trioxa-4-phosphapentacosan-1-aminium, hydroxide, inner salt, 4-oxide To a stirred solution of 46 ml of 0.98 molar borane in tetrahydrofuran at 0° C. under argon is added over 20 minutes, a solution of 2.4 q of 2-[[hydroxy[(2methylenenonadecyl)oxy]phosphinyl]oxy]-N,N,N-trimethylethaniminium, hydroxide, inner salt in 75 ml of dry dichloromethane. This mixture is stirred for 1.5 hours at 0° C., then the excess tetrahydrofuran and borane are removed. A 50 ml portion of tetrahydrofuran:water (10:1) is added and the solvent removed. Methanol is added and evaporated. The residual oil is chromatographed and the product triturated with ether, to give 0.72 g of the desired product as a white powder.

EXAMPLE 60

2-[(Hexadecyloxy)methyl]-3-(phenylmethoxy)propyl phosphoric acid, diphenyl ester To a solution of 1.0 g of 3-[(hexadecyloxy)methyl]-4-(phenylmethoxy)-butanol in a mixture of 10 ml of dry acetonitrile and 10 ml of dry dichlormethane is added 831 mg of 5-chloro-1-methyl imidazole followed by 830 mg of diphenyl chlorophosphate. This mixture is stirred overnight under argon. An 830 mg portion of diphenyl chlorophosphate is added and stirring continued. The solvent is removed and the residue purified by chromatography, to give 1.27 g of the desired compound as a colorless oil.

EXAMPLE 61

3-(Hexadecyloxy)-2-(hydroxymethyl)propyl phosphoric acid, diphenyl ester

A solution of 1.27 g of 2-[(hexadecyloxy)methyl]-3-(phenylmethoxy)propyl phosphoric acid, diphenyl ester in 50 ml of cyclohexane and 5 ml of glacial acetic acid is hydrogenated over 500 mg of 5% palladium-on-carbon in a Parr apparatus at an initial pressure of 25 psi for 18 hours. The mixture is filtered and washed with cyclohexane. The combined filtrate and wash is evaporated to give an oil. This oil is evaporated twice from toluene, to give 685 mg of the desired compound as an oil.

EXAMPLE 62

4-[(Hexadecyloxy)methyl]-7-hydroxy-N,N,N-trimethyl-1,1-diphenoxy-2.6.8 trioxa-1.7-diophosphadecan-10-aminium, hydroxide, inner salt, 1,7-dioxide To a solution of 0.65 g of 3-(hexadecyloxy)-2-(hydroxymethyl)propyl phosphoric acid, diphenyl ester in 15 ml of carbon tetrachloride, stirred in an ice bath under argon is added 0.48 ml of triethylamine followed by the dropwise addition of 0.42 g of phosphoryl dichloride in 2 ml of carbon tetrachloride. This mixture is stirred overnight at room temperature, then 10 ml of toluene is added and the mixture is filtered and washed with toluene. The filtrate and wash are combined and taken to dryness. The residue is stirred in 50 ml of tetrahydrofuran and 50 ml of 0.5M aqueous sodium acetate for 2 hours, then the tetrahydrofuran is removed in vacuo. The aqueous residue is acidified with dilute hydrochloric acid and extracted twice with ether. The ether extracts are combined, dried and evaporated to an oil.

A mixture of this oil in 30 ml of chloroform and 60 ml of a solution of 50 g of trimethylamine in 100 ml of acetonitrile is stirred at reflux for 5 hours and then cooled overnight. The solvent is removed and the residual oil stirred with 160 mg of silver carbonate and 30 ml of methanol for 2 hours, then filtered. The filtrate is evaporated and the residue purified by chromatography, to give 267 mg of the desired compound as a glass.

EXAMPLE 63

Hexadecyl methyl-2-(phenylmethoxy)phosphoric acid, ethyl ester

To a solution of 28.4 1 of phosphorous oxychloride in 200 ml of carbon tetrachloride is added dropwise a solution of 50 g of 1-hexadecanol in 125 ml of carbon tetrachloride. This mixture is stirred overnight, and the solvent removed. The residue is evaporated twice from toluene in vacuo to give the phosphonyl dichloride as a dark oil.

A mixture of 156.75 g of dry ethylene glycol and 64.37 g of 87.2% potassium hydroxide is warmed and stirred until a complete solution. The mixture is then stirred in a 90° C. oil bath and 130.51 g of benzyl chloride is added dropwise over 2 hours. This mixture is then stirred at 130° C. for 2 hours, cooled and 500 ml of water added. The oil is extracted twice with ether. The extracts are combined and evaporated. The residue is distilled, giving 83.2 g of ethylene glycol monobenzyl ether.

To a solution of 34.4 g of phosphorodichloridic acid, hexadecyl ester in 150 ml of carbon tetrachloride, stirred in an ice bath, is added dropwise, at a fast rate, 27 ml of triethylamine. A solution of 10 g of ethylene glycol monobenzyl ether in 50 ml of carbon tetrachloride is added dropwise. After 5 minutes, the mixture is removed from the ice bath and stirred for 2 hours. A 100 ml portion of dry toluene is added and the mixture filtered and washed with toluene. The filtrate and wash are combined and evaporated. A 50 g portion of the residue is dissolved in 350 ml of methanol and treated with 29 ml of triethylamine for 1 hour, then evaporated. The residue is purified by chromatography, to give 16.2 g of the desired compound as a pale yellow oil.

EXAMPLE 64

Hexadecyl 2-hydroxyethyl phosphoric acid, methyl ester

A solution of 11.2 g of hexadecyl methyl 2-(phenylmethoxy)phosphoric acid, ethyl ester in 50 ml of glacial acetic acid and 100 ml of methanol is hydrogenated over 1.0 g of 10% palladium-on-carbon in a Parr apparatus at an initial pressure of 30 psi for 5 hours. Hydrogenation is repeated overnight. The mixture is filtered, the filtrate evaporated and the residue evaporated twice from toluene, to give 7.1 g of the desired compound as a waxy solid.

EXAMPLE 65

2-[[(2-Bromoethoxy)hydroxyphosphinyl]oxy]ethyl hexadecyl phosphoric acid, methyl ester To a solution of 4.52 g of 2-bromoethyl phosphorochloridate in 190 ml of dry carbon tetrachloride, stirred in an ice bath under argon, is added dropwise, 2.7 ml of triethylamine and a solution of 7.1 g of hexadecyl-2-hydroxyethyl phosphoric acid, methyl ester in 30 ml of dry carbon tetrachloride. This mixture is stirred for 5 minutes, then the ice bath is removed and stirring continued at ambient temperature for 2 hours. A 100 ml portion of dry toluene is added and the mixture is filtered and washed with toluene. The combined filtrate and wash is evaporated. The residue is hydrolyzed in a mixture of 150 ml of tetrahydrofuran and 150 ml of 0.5M aqueous sodium acetate with stirring for 2 hours. The tetrahydrofuran is removed and the aqueous phase acidified with dilute hydrochloric acid and extracted twice with ether. The extracts are combined, washed with saturated aqueous sodium chloride, dried, filtered and evaporated. The residue is purified by chromatography, to give 5.17 g of the desired compound.

EXAMPLE 66

3,9-Dihydroxy-N,N,N-trimethyl-3,5,8,10-tetraoxa-4,9-diphosphahexacosan-1-aminium, hydroxide, 4-(inner salt) 4,9-dioxide To a solution of 5.0 g of 2-[[(2-bromoethoxy)hydroxyphosphinyl]oxy]ethyl hexadecyl phosphoric acid, methyl ester in 100 ml of dry acetonitrile and 90 ml of dry chloroform is added 50 g of anhydrous trimethylamine. This solution is stirred at reflux for 4 hours, then the solvent is removed. The residue is stirred for 2 hours in 50 ml of methanol containing 1.215 g of silver carbonate, then filtered and washed with methanol. The combined filtrate and wash is taken to dryness. The residue is purified by chromatography (65:43:10 chloroform:methyl alcohol:water), to give 2.6 g of the desired compound.

EXAMPLE 67

Methyl octadecyl 2-(phenylmethoxy)phosphoric acid, ethyl ester

To a solution of 36.3 g of phosphoryl dichloride in 130 ml of carbon tetrachloride, while stirring in an ice bath is added dropwise, at a fast rate, 25.7 ml of triethylamine. A solution of 10 g of phosphorodichloridic acid, octadecyl ester in 50 ml of carbon tetrachloride is added dropwise. This mixture is stirred for 5 minutes, then the ice bath is removed and stirring continued at room temperature for 2 hours. A 100 ml portion of toluene is added, the mixture filtered and washed with toluene.

The combined filtrates and wash are refrigerated then evaporated. The residue is dissolved in 350 ml of methanol, 28 ml of triethylamine added and this solution stirred under argon for 1 hour. The solvent is removed, the residue dissolved in ethyl acetate:hexane (1:1) and then evaporated to give an oil. The oil is purified by chromatography, to give 25.8 g of the desired compound as a waxy solid.

EXAMPLE 68

2-Hydroxyethyl methyl phosphoric acid, octadecyl ester

A solution of 10.0 g of methyl octadecyl 2-(phenylmethoxy)phosphoric acid, ethyl ester in 100 ml of methanol and 50 ml of glacial acetic acid is hydrogenated over 1.0 g of 10% palladium-on-carbon at an initial pressure of 30 psi for 24 hours. The mixture is filtered and washed with methanol. The combined filtrate and wash is evaporated and then evaporated from toluene three times. The residue is purified by chromatography, to give 3.26 g of the desired compound.

EXAMPLE 69

4,9-Dihydroxy-N,N,N-trimethyl-3,5,8,10-tetraoxa-4,9-diphosphaoctacosan-1-aminium, hydroxide, 4-(inner salt), 4,9-dioxide To a solution of 2.0 g of 2-hydroxyethyl methyl phosphoric acid, octadecyl ester in 75 ml of dry benzene, cooled in an ice bath under argon, is added with stirring 0.68 ml of triethylamine followed by a solution of 0.697 g of phosphoryl chloride in 5 ml of dry benzene. This mixture is stirred for 5 minutes, then the ice bath removed and stirring continued for 24 hours. The solvent is removed leaving a white amorphous solid.

This solid is slurried in 50 ml of dry acetonitrile, 10 ml of 33% trimethylamine in acetonitrile is added and this solution is transferred to a pressure bottle, rinsing with 5 ml of the trimethylamine solution. The bottle is sealed and the solution stirred at 65° C. overnight. The mixture is cooled and the insoluble material decanted, evaporated and the two solids combined. This solid is purified by chromatography, to give 0.21 g of the desired compound.

EXAMPLE 70

Phosphorodichloridic acid, hexadecyl ester

To a moisture protected solution of 28.4 ml of phosphorous oxychloride in 200 ml of carbon tetrachloride is added dropwise with stirring a solution of 50 g of 1-hexadecanol in 125 ml of carbon tetrachloride. After stirring at ambient temperature for 18 hours, the solvent is removed and the residue evaporated with toluene several times to give 71 g of the desired product as a vacuum dried water white oil.

EXAMPLE 71

Hexadecyl 2-(hexadecyloxy)-1-[[(4-methoxyphenyl) diphenylmethoxy]methyl]ethyl phosphoric acid, methyl ester To a solution of 7.5 g of 1-[(4-methoxyphenoxy)diphenylmethoxy]-3-hexadecyloxy-2-propanol in 40 ml of dry carbon tetrachloride is added 1.0 g of dimethylaminopyridine and 5.32 ml of triethylamine. A solution of 6.4 g of phosphorodichloridic acid, hexadecyl ester in 10 ml of dry carbon tetrachloride is added dropwise at a fast rate with water bath cooling. This mixture is stirred at room temperature overnight, then 4.57 g of phosphorodichloridic acid, hexadecyl ester and 1.8 ml of triethylamine are added and stirring continued for 48 hours. An 8.5 ml portion of triethylamine and 250 ml of methanol are added, the mixture is stirred for 2 hours and then diluted with 100 ml of sodium bicarbonate solution. This mixture is extracted three times with chloroform, the combined extracts dried and evaporated and the residue purified by chromatography, to give 6.44 g of the desired compound.

EXAMPLE 72

Hexadecyl 2-(hexadecyloxy)-1-(hydroxymethyl)ethyl phosphoric acid, methyl ester

A solution of 630 mg of hexadecyl 2-(hexadecyloxy)-1-[[(4-methoxyphenyl)diphenylmethoxy]methyl]ethyl phosphoric acid, methyl ester in 3 ml of methanol and 1.5 ml of chloroform is heated to boiling. The mixture is removed from the heat and 300 mg of ion exchange resin added. This mixture is stirred for 1 hour and 40 minutes, then filtered, diluted with chloroform, washed with aqueous sodium bicarbonate, dried and the solvent removed. The residue is chromatographed, to give 110 mg of the upper (less polar) isomer and 120 mg of the lower (more polar) isomer.

EXAMPLE 73

3,5,8,10-Tetraoxa-4,9-diphosphahexacosan-1-aminium, 7-[(hexadecyloxy)methyl]-4-hydroxy-9-methoxy-N,N,N-trimethyl- hydroxide, inner salt, 4,9-dioxide To a solution of 1.6 g of methyl hexadecyl 2-(hexadecyloxy)-1-(hydroxymethyl)ethyl phosphoric acid in 40 ml of carbon tetrachloride under an inert atmosphere is added 0.79 g of phosphonyl dichloride followed by 0.5 ml of triethylamine. The mixture is stirred at ambient temperature for 3 hours then stored in a refrigerator for 18 hours. After reaching ambient temperature, the mixture is filtered and the cake washed with toluene. The volatiles are removed and the residue dissolved in 50 ml of tetrahydrofuran and 50 ml of 0.5M sodium acetate. After stirring at ambient temperature for 2 hours, the volatiles are removed and the residue acidified with dilute hydrochloric acid then extracted with ether. The organic layer is washed with brine and dried. The volatiles are removed to give 1.6 g of a wax which is dissolved in 45 ml of chloroform, 50 ml of acetonitrile and 25 g of trimethylamine. The mixture is stirred in an oil bath of 70° C. for 4 hours. The volatiles are removed and the residue dissolved in 20 ml of chloroform, 20 ml of methyl alcohol and 2 ml of water. While stirring, 0.35 g of silver carbonate is rapidly added followed by continued stirring at ambient temperature for 17 hours. The mixture is filtered through diatomaceous earth and the cake washed with 1:1 methyl alcohol:chloroform. The volatiles are removed and the residue chromatographed on silica gel with 30% methyl alcohol:chloroform followed by 65:35:6 chloroform:methyl alcohol:water. The volatiles are removed and the residue dissolved in ether, cooled and filtered to give 310 mg of the desired product as a white solid.

EXAMPLE 74

3,5,8,10-Tetraoxa-4,9-diphosphahexacosan-1-aminium, 7-[(hexadecyloxy)methyl]-4-hydroxy-9-methoxy-N,N,N-trimethyl-, hydroxide, inner salt, 4,9-dioxide To a solution of 1.22 g of methyl hexadecyl 2-(hexadecyloxy)-1-(hydroxymethyl)ethyl phosphoric acid in 30 ml of carbon tetrachloride under an inert atmosphere is added 0.6 g of phosphonyl dichloride followed by 0.4 ml of triethylamine. The mixture is stirred at ambient temperature for 5 hours then filtered through diatomaceous earth. The cake is washed with toluene and the combined filtrates evaporated to a syrup which is stirred at ambient temperature for 1.5 hours with 40 ml of tetrahydrofuran and 40 ml of 0.5M sodium acetate. The tetrahydrofuran is evaporated and the aqueous residue acidified with dilute hydrochloric acid followed by ether extraction. The organic layer is washed with brine, dried and the solvent removed to give 1.6 g of a wax. The wax is dissolved in 35 ml of chloroform, 40 ml of a solution of 50 g of trimethylamine in 100 ml of acetonitrile and heated in an oil bath of 70° C. for 4 hours. The volatiles are removed and the residue stirred in a solution of 20 ml of chloroform, 20 ml of methyl alcohol and 2 ml of water containing 265 mg of silver carbonate at ambient temperature for 2 hours. The mixture is filtered through diatomaceous earth and the cake washed with 1:1 chloroform:methyl alcohol. The volatiles are removed and the residue columned on silica gel with 30% methyl alcohol-chloroform followed by 65:35:6 chloroform:methyl alcohol:water to give 287 mg of white wax after solvent evaporation and cooling the residue in ether.

EXAMPLE 75

3,5,8,10-Tetraoxa-4,9-diphosphahexacosan-1-aminium, 7-[(hexadecyloxy)methyl]-4,9-dihydroxy-N,N,N-trimethyl-, hydroxide, 4-inner salt), 4,9-dioxide To a stirred solution of 2.38 g of phosphoric acid, hexadecyl 2-(hexadecyloxy)-1-(hydroxymethyl)ethyl methyl ester, in 60 ml of carbon tetrachloride is added 1.17 g of phosphoryl dichloride and by 0.73 ml of triethylamine followed by stirring at ambient temperature for 3 hours and allowing to stand in a refrigerator for 18 hours. After reaching ambient temperature, the mixture is filtered and the cake washed with toluene. The filtrate is taken to dryness and the residue stirred at ambient temperature with a solution of 75 ml of tetrahydrofuran and 75 ml of 0.5M sodium acetate for 2 hours. The tetrahydrofuran is removed and the aqueous residue acidified with dilute hydrochloric acid and extracted with ether. The separated organic layer is washed with brine, dried and evaporated to a syrup which is stirred in a solution of 45 ml of chloroform and 50 ml of acetonitrile containing 25 g of trimethylamine at an oil bath temperature of 70° C. for 18 hours. The volatiles are removed and the residue stirred with 20 ml of chloroform, 20 ml of methyl alcohol and 2.85 mg of silver carbonate at ambient temperature for 2 hours. The mixture is filtered through diatomaceous earth and the cake washed with 1:1 chloroform:methyl alcohol. The volatiles are removed and the residue columned on silica gel with 30% methyl alcohol-chloroform and 65:35:6 chloroformmethyl alcohol-water. Fractions containing product are combined and evaporated. The residue is dissolved in ether and cooled in a refrigerator to give 560 mg of the desired product as a white solid.

EXAMPLE 76

Phosphorodichloridic acid, pentyl ester

To a tap water cooled solution of 79 g of phosphorous oxychloride in 200 ml of carbon tetrachloride is added dropwise with stirring a solution of 50 g of 1-pentanol in 125 ml of carbon tetrachloride. The temperature rises to 30° C. and stirring is continued for 18 hours. The solvent is evaporated and the syrup evaporated with toluene several times. The residue is distilled from a Kugelrohr still to give 108.7 g of the desired product as a colorless oil, B.P. 85°–90° C./0.3 mm.

EXAMPLE 77

Phosphoric acid, 2-(hexadecyloxy)-1-[[(4-methoxyphenyl)-diphenylmethoxy]methyl]ethyl methyl pentyl ester To a stirred ice bath cooled solution of 15 g of 1-[(4-methoxyphenoxy)diphenylmethoxy]-3-hexadecyloxy-2-propanol in 50 ml of carbon tetrachloride is added 2.1 g of dimethylaminopyridine followed by the addition of 8.2 ml of triethylamine. A solution of 7.31 g of phosphorodichloridic acid, pentyl ester in 10 ml of carbon tetrachloride is added dropwise, the cooling bath removed and the reaction stirred at ambient temperature for 66 hours. A solution of 10 ml of triethylamine and 500 ml of methyl alcohol is added followed by continued stirring for 2 hours. The reaction is diluted with 1500 ml of 5% sodium bicarbonate and extracted with chloroform. The organic layer is dried and the volatiles removed to give 21 g of an oil which is dry columned on silica gel with 1:4 ethyl acetate:hexanes. Product fractions are combined in chloroform and the solvent removed to give 10 g of the desired product as a yellow oil.

EXAMPLE 78

Phosphoric acid, 2-(hexadecyloxy)-1-(hydroxymethyl) ethyl methyl pentyl ester, more polar isomer Phosphoric acid, 2-(hexadecyloxy)-1-(hydroxymethyl) ethyl methyl pentyl ester, less polar isomer A solution of 10 g of phosphoric acid, 2-(hexadecyloxy)-1-[[(4-methoxyphenyl)-diphenylmethoxy]-methylethyl methyl pentyl ester in 100 ml of methyl alcohol and 50 ml of chloroform is brought to a boil, the heat removed and 5 g of Amberlite ®-15 resin carefully added. The reaction is stirred at ambient temperature for 2 hours, filtered to remove the resin and the cake washed well with 2:1 methyl alcohol:chloroform. The solvent is removed to give 9.7 g of a thick syrup. The product is chromatographed using dry column silica gel with 1:1 ethyl acetate:hexanes. Product fractions are combined and the solvents evaporated to give 1.38 g of a less polar isomer oily product and 1.46 g of a more polar isomer oily product.

EXAMPLE 79

2-Bromoethyl Phosphorodichloridate

To a stirred solution of 412.98 g of phosphorous oxychloride in 910 ml of carbon tetrachloride is added 224.4 g of 2-bromoethanol with stirring over 30 minutes. The temperature increases to 34° C. and the reaction is stirred under a dry atmosphere for 18 hours. The solvent is removed to a syrup which is evaporated with toluene several times. The residue is distilled to afford 161 g of the desired product as a colorless oil, B.P. 82° C./0.3 mm.

EXAMPLE 80

3,5,8,10-Tetraoxa-4,9-diphosphapentadecan-1-aminium, 7-[(hexadecyloxy)methyl]-4-hydroxy-9-methoxy-N,N,N-trimethyl-, hydroxide, 4-(inner salt),4,9-dioxide, more polar isomer 3,5,8,10-Tetraoxa-4,9-diphosphapentadecan-1-aminium, 7-[(hexadecyloxy)methyl]-4,9-dihydroxy-N,N,N-trimethyl-, hydroxide, 4-(inner salt), 4,9-dioxide, less polar isomer To a stirred solution of 1.46 g of phosphoric acid, 2-(hexadecyloxy)-1-(hydroxymethyl)ethyl methyl pentyl ester, lower diastereomer in 35 ml of carbon tetrachloride, cooled in an ice bath under argon, is added dropwise a solution of 1.0 g of 2-bromoethyl phosphorodichloridate in 1 ml of carbon tetrachloride followed by 0.7 ml of triethylamine. The bath is removed and the mixture stirred at ambient temperature for 1 hour followed by storing in a refrigerator for 18 hours. The mixture is brought to ambient temperature and filtered through diatomaceous earth. The cake is washed with toluene and the combined solvents evaporated. The residue is hydrolyzed by stirring for 2 hours at ambient temperature with 50 ml of tetrahydrofuran and 50 ml of 0.5M sodium acetate. The tetrahydrofuran is evaporated and the aqueous residue acidified with hydrochloric acid followed by ether extraction. The organic layer is washed with brine, dried and the solvent removed to give 1.8 g of a stiff oil which is dissolved in 40 ml of chloroform and 40 ml of a solution of 50 g of trimethylamine in acetonitrile then heated in an oil bath of 65° C. for 4 hours. The solvent is evaporated and the residue dissolved in 30 ml of methyl alcohol followed by stirring with 450 mg of silver carbonate at ambient temperature for 1.5 hours. The mixture is filtered and the filtrate evaporated to a residue which is chromatographed on silica gel and eluted with 30% methyl alcohol:chloroform, and then 65:35:6 chloroform:methyl alcohol:water. The solvent is evaporated to give 253 mg of the less polar isomer product as a glass. The column is further eluted with the same solvent system to give 275 mg of the more polar isomer product as a white solid.

EXAMPLE 81

3,5,8,10-Tetraoxa-4,9-diphosphapentadecan-1-aminium, 7-[(hexadecyloxy)methyl]-4-hydroxy-9-methoxy-N,N,N-trimethyl-, hydroxide, 4-(inner salt), 4,9-dioxide, less polar isomer To a solution of 1.28 g of phosphoric acid, 2-(hexadecyloxy)-1-(hydroxymethyl)ethyl methyl pentyl ester, upper diastereomer in 35 ml of carbon tetrachloride, cooled in an ice bath under an inert atmosphere is added rapidly dropwise 0.9 g of 2-bromoethyl phosphorodichloridate followed by the rapid dropwise addition of 0.6 ml of triethylamine. The bath is removed and the mixture stirred at ambient temperature for 1 hour then stored in the refrigerator for 18 hours. After reaching room temperature, the mixture is filtered through diatomaceous earth rinsing the cake with toluene. The solvents are removed and the residue stirred at room temperature with 50 ml of tetrahydrofuran and 50 ml of 0.5M sodium acetate for 2 hours. The tetrahydrofuran is removed and the aqueous residue acidified with hydrochloric acid and extracted with ether. The organic layer is washed with brine, dried and evaporated to give 1.9 g of a stiff oil, which is dissolved in 40 ml of chloroform and 40 ml of a solution containing 50 g of trimethylamine in 100 ml of acetonitrile. The mixture is heated in an oil bath of 65° C. for 4 hours. The solvent is removed and the residue stirred in 30 ml of methyl alcohol containing 400 mg of silver carbonate at ambient temperature for 1.5 hours. The mixture is filtered through diatomaceous earth and the filtrate evaporated to give 2 g of a glass which is chromatographed on silica gel with 30% methyl alcohol:chloroform and 65:35:6 chloroform:methyl alcohol:water. Fractions containing product are combined and the volatiles removed to give 300 mg of the desired product as a dried glass.

EXAMPLE 82

7-[(Chloroacetyl)oxy]-4-hydroxy-N,N,N-trimethyl-3,5,9-trioxa-4-phosphapentacosan-1-aminium, hydroxide, inner salt, 4-oxide A mixture of 500 mg of 4-hydroxy-N,N,N-tri-methyl-3,5,9-trioxa-4-phosphapentacosan-1-aminium, hydroxide, inner salt, 86.2 mg of anhydrous sodium acetate and 1.8 g of chloroacetic anhydride is stirred at reflux under argon in 25 ml of chloroform for 2 hours then stirred at room temperature for four days. An additional 500 mg of chloroacetic anhydride is added and the mixture stirred at reflux under argon for 5 hours. The solvent was removed in vacuo and the concentrate columned on silica gel with 30% methanol-chloroform. Further elution with 65:35:6 chloroform:methanol:water affords 155 mg of the desired product as a glass following solvent removal and drying in vacuum.

EXAMPLE 83

10-Bromo-7-[(hexadecyloxy)methyl]-4-hydroxy-N,N,N-trimethyl-9-oxo-3,5,8-trioxa-4-phosphahexacosan-1-aminium, hydroxide, inner salt, 4-oxide A solution of 455 mg of 4-hydroxy-N,N,N-trimethyl-3,5,9-trioxa-4-phosphapentacosan-1-aminium, hydroxide, inner salt, 4-oxide and 472 mg of 2-bromostearic acid in 15 ml of dichloromethane is stirred at room temperature under argon while 402 mg of dicyclohexylcarbodiimide is rapidly added followed by 23.8 mg of dimethylaminopyridine. Stirring is continued for 18 hours. The mixture is filtered and the solvent removed in vacuo to give 1.1 g of a glass. The product is chromatographed on silica gel using 30% methanol-chloroform. Further elution with 65:35:6 chloroform:methanol:water affords 422 mg of a glass which is triturated with ether and cooled to afford 332 mg of the desired product as a white amorphorous solid.

EXAMPLE 84

3,5,9-Trioxa-4-phosphapentacosan 1-aminium, 7-[(bromoacetyl)oxy]-4-hydroxy-N,N,N-trimethyl-, hydroxide, inner salt, 4-oxide A mixture of 500 mg of 3,5,9-trioxa-4-phosphapentacosan-1-aminium, 4-hydroxy, N,N,N-trimethyl, hydroxide, inner salt, 4-oxide, 86.2 mg of sodium acetate and 1.35 g of bromoacetic anhydride in 25 ml of chloroform is stirred at an oil bath of 70° C. for 5 hours then allowed to cool overnight. The solvent is removed and the residue columned on silica gel with 30% methyl alcohol:chloroform followed by 65:35:6 chloroform:methyl alcohol:water to give 198 mg of the desired product as a glass.

EXAMPLE 85

4-[2-(Acetyloxy)-3-(octadecyloxy)propoxy]-N,N,N-trimethyl-1-butanaminium bromide A solution of 580 mg of 4-[2-hydroxy-3-(octadecyloxy)-propoxy]-N,N,N-trimethyl-1-butanaminium bromide in 5 ml of acetic anhydride is stirred at reflux under inert gas for 15 minutes. Toluene is added and the solvents evaporated followed by several additional toluene evaporations. The residue is stirred with ether and stored at 0° C. for several days. The resulting solid is collected and dried to give 480 mg of the desired product.

EXAMPLE 86

3-(Pentyloxy)-1,2-propanediol

To a mixture of 18.6 g of hexane washed sodium hydride in 400 ml of toluene under inert gas is added dropwise over 1 hour a solution of 60 g of solketal in 100 ml of toluene. Stirring is continued for 30 minutes at ambient temperature and a solution of 57 g of 1-bromopentane in 100 ml of toluene is added dropwise. The mixture is heated at reflux for 1.5 hours and then allowed to cool at ambient temperature for 18 hours. A 500 ml volume of ice water is carefully added. The organic layer is separated, washed with saturated sodium chloride and dried. The solvent is removed and the residual oil stirred at reflux with 900 ml of methyl alcohol and 100 ml of 1N hydrochloric acid for 2 hours. The solvent is removed and the syrup dissolved in chloroform. The aqueous layer is removed and the organic layer dried and evaporated. The concentrate is vacuum distilled in a Kugelrohr apparatus to give 49.4 g (bp 85°–86° C./0.15 mm) of the desired product as a colorless oil.

EXAMPLE 87

1[(4-methoxyphenoxy)diphenylmethoxy]-3-(pentyloxy)-2-propanol

To an ice bath cooled solution of 48 g of 3-(pentyloxy)-1,2-propanediol in 150 ml of dry pyridine under inert gas is added at a rapid rate a warm solution of 127.92 g of p-methoxytrityl chloride in 165 ml of tetrahydrofuran. The mixture is stirred for an additional 20 minutes at ice bath temperature followed by 2 hours at ambient temperature and 18 hours in a refrigerator. The reaction mixture is filtered and the cake washed with ether. The combined filtrate and washings are evaporated to a residue which is dissolved in chloroform and washed with 10% sodium bicarbonate, water and dried to give a thick oil upon evaporation of the volatiles. The residue is purified by high pressure liquid chromatography on silica gel using 1:9 ethyl acetate:hexanes to give 96 g of the desired product as an oil.

EXAMPLE 88

Phosphoric Acid.
1-(4-methoxyphenyl)diphenylmethoxy]methyl]-2-(pentyloxy)ethyl methyl pentyl ester To a solution of 23.8 g of 1-[(4-methoxyphenoxy)diphenylmethoxy]-3-(pentyloxy)-2-propanol in 80 ml of dry carbon tetrachloride under inert gas is added 4.54 g of dimethylaminopyridine followed by 35.1 ml of triethylamine. While cooling in an ice bath, a solution of 31.44 g of phosphorodichloridic acid, pentyl ester in 45 ml of carbon tetrachloride is added dropwise at a moderate rate. The water bath is removed and stirring continued for 4 days. Added 16 ml of triethylamine and 790 ml of methyl alcohol followed by stirring at ambient temperature for 2 hours. Diluted with 2350 ml of 5% sodium bicarbonate and extracted with chloroform. The extract is dried and evaporated to an oil which is purified on silica gel with 30:70 ethyl acetate:hexanes to give 15.1 g of the desired product as a yellow thick oil.

EXAMPLE 89

Phosphoric acid, 1-(hydroxymethyl)-2 (pentyloxy)ethyl methyl pentyl ester

To a solution of 13.5 g of phosphoric acid, 1-[[(4-methoxyphenyl)diphenylmethoxy]-methyl]-2-(pentyloxy)ethyl methyl pentyl ester in 68 ml of chloroform and 136 ml of methyl alcohol heated to boiling is slowly added 6.8 g of Amberlyst ®-15 resin. The heat is removed and the mixture stirred at ambient temperature for 2 hours. The volatiles are removed and the residue dissolved in chloroform then washed with dilute sodium bicarbonate, dried and evaporated to an oily residue which is purified on silica gel using 1:1 ethyl acetate:hexanes to give 6 g of the desired compound as a colorless oil.

EXAMPLE 90

Phosphoric acid, 1-[[[(2-bromoethoxy]hydroxyphosphinyl]oxy]1methyl]-2-(pentyloxy]ethyl methyl pentyl ester To a stirred solution of 6.0 g of phosphoric acid 1-(hydroxymethyl)-2-(pentyloxy)ethyl methyl pentyl ester in 140 ml of carbon tetrachloride while cooling in an ice bath under inert gas is added very rapidly a solution of 5.8 g of 2-bromoethyl phosphorodichloridate in 6 ml of carbon tetrachloride. The ice bath is removed and stirring continued for 3 hours at ambient temperature. Added 100 ml of toluene, stirred for a short time and filtered. The cake is washed with additional toluene and the filtrates are evaporated to a residue which is stirred at ambient temperature for 1.5 hours with 125 ml of 0.5M sodium acetate and 125 ml of tetrahydrofuran. The tetrahydrofuran is removed to an aqueous residue which is cooled and acidified with hydrochloric acid until a gum separates. The ether extracts are dried and evaporated to a residue which is evaporated with toluene several times, then dried with a vacuum pump. The residue is purified on 100 g of magnesium silicate with chloroform followed by 10% methyl alcohol:chloroform. Fractions containing the desired product are evaporated to give 5.6 g of the desired product as a stiff oil.

EXAMPLE 91

3,5,8,10-Tetraoxa-4,9 diphosphapentadecan-1-aminium, 4-hydroxy-9-methoxy-N,N,N-trimethyl-7-[(pentyloxy)methyl]-, hydroxide, inner salt, 4,9-dioxide, more polar isomer 3,5,8,10-Tetraoxa-4,9-diphosphapentadecan-1-aminium, 4,9-dihydroxy-N,N,N-trimethyl-7-[(pentyloxy)methyl]-, hydroxide, 4-(inner salt), 4,9-dioxide, less polar isomer To 5.2 g of phosphoric acid, 1-[[[(2-bromoethoxy)hydroxyphosphinyl]oxy]methyl]-2-(pentyloxy)ethyl methyl pentyl ester in 115 ml of dry chloroform is added 130 ml of dry acetonitrile and 50 ml of anhydrous trimethylamine. The solution is heated at 62° C. for 4 hours and the solvents removed. The residue is dissolved in 70 ml of methyl alcohol and stirred with 1.4 g of silver carbonate at ambient temperature for 2 hours. The reaction mixture is filtered through diatomaceous earth followed by washing with methyl alcohol. The combined filtrates are evaporated to a glass which is purified by chromatography on silica gel eluting with 30% methyl alcohol:chloroform then chloroform:methyl alcohol:water, 65:35:6 to give 395 mg of the less polar isomer product as a glass. Further elution of the column gives 2.7 g of the second more polar isomer product as a glass.

EXAMPLE 92

(R)-4-](Hexadecyloxy)methyl]-2,2-dimethyl-1,3-dioxolane

To a mixture of 3.2 g of hexanes washed sodium hydride in 67 ml of dry toluene while stirring under inert gas is added dropwise over 1 hour a solution of 10.52 g of L-2,3-O-isopropylidene-sn-glycerol in 17 ml of dry toluene. Following 15 minutes of stirring, a solution of 24.1 g of hexadecylbromide in 17 ml of toluene is added dropwise over 20 minutes. The mixture is gradually heated to reflux followed by 1.5 hours at reflux and 18 hours at ambient temperature. The reaction mixture is filtered, the cake washed with toluene and the combined filtrates washed with water and brine then dried. The reaction mixture is filtered and the solvent removed to give 28.2 g of the desired product as a yellow oil.

EXAMPLE 93

(S)-3-(Hexadecyloxy)-1,2-propanediol

A mixture of 28.2 g of (R)-4-[(hexadecyloxy)methyl]-2,2-dimethyl-1,3-dioxolane in 189 ml of methyl alcohol and 21 ml of 1N hydrochloric acid is stirred at reflux for 2.5 hours followed by 12 hours at ambient temperature. The reaction is cooled, filtered and the cake washed with cold methyl alcohol then dried to give 20.3 g of the desired product as white plates, m.p. 63°–64° C.

EXAMPLE 94

(R)-1-(Hexadecyloxy)-3-[(4-methoxyphenyl)diphenyl methoxy]-2-propanol

To a solution of 15.34 g of (S)-3-(hexadecyloxy)-1,2-propanediol in 50 ml of pyridine is added dropwise with stirring a solution of 20.96 g of p-methoxytrityl chloride in 30 ml of tetrahydrofuran. Stirring is continued at ambient temperature for 2 hours followed by refrigeration for 18 hours. The mixture is filtered and the cake washed with ether. The combined filtrates are evaporated to a residue which is dissolved in chloroform and washed with 10% sodium bicarbonate and water then dried and evaporated to an oil which is purified by high pressure liquid chromatography on silica gel using 1:9 ethyl acetate:hexanes to give 28.44 g of the desired product as an oil.

EXAMPLE 95

Phosphoric acid, (R1-hexadecyl 2-(hexadecyloxy)-1-[[(4-methoxyphenyl)diphenylmethoxy]methyl]ethyl methyl ester To a stirred solution of 14 g of (R)-1-(hexadecyloxy)-3-[(4-methoxyphenyl)diphenylmethoxy]-2-propanol in 60 ml of carbon tetrachloride under inert gas is added 2 g of 4-dimethylaminopyridine and 14.24 ml of triethylamine. A solution of 21.94 g of phosphorodichloridic added dropwise at a rapid rate. Stirring is continued at ambient temperature for 4 days. A solution of 17 ml of triethylamine and 500 ml of methyl alcohol is added followed by stirring at ambient temperature for 2 hours. The reaction mixture is poured into 1800 ml of 10% sodium bicarbonate and extracted several times with chloroform. The combined extracts are dried and evaporated to a residue which is purified by high pressure liquid chromatography on silica gel using 1:7 ethyl acetate:hexanes to give 13 g of the desired product as an oil.

EXAMPLE 96

Phosphoric acid, hexadecyl 2-(hexadecyloxy)-1-(hydroxymethyl)ethyl methyl ester, (1S)-, upper diastereomer Phosphoric acid, hexadecyl 2-(hexadecyloxy)-1-hydroxymethyl)ethyl methyl ester, (1S)-, lower diastereomer To a solution of 13 g of phosphoric acid, (R)-hexadecyl 2-(hexadecyloxy)-1-[[(4-methoxyphenyl) methoxy]methyl]ethyl methyl ester, in 90 ml of methyl alcohol and 45 ml of chloroform brought to a gentle boil is added 7.7 g of Amberlyst ®-15 resin. The mixture is stirred at ambient temperature for 1.5 hours then filtered. The filtrate is evaporated to a residue which is dissolved in chloroform, washed with dilute sodium bicarbonate and dried. The solvent is evaporated to a residue which is purified by chromatography on silica gel using 1:1 ethyl acetate:hexanes to afford 3.6 g of an upper diastereomer and 3.1 g of lower diastereomer.

EXAMPLE 97

3,5,8,10-Tetraoxa-4,9-diphosphahexacosan-1-aminium, 7-[(hexadecyloxy)methyl]-4,9-dihydroxy-N,N,N-trimethylhydroxide, 4-(inner salt), 4,9-dioxide, more polar isomer To a solution of 3.1 g of phosphoric acid, hexadecyl 2-(hexadecyloxy)-1-hydroxy-methyl)ethylmethyl ester, (1S)-, more polar diastereomer in 50 ml of carbon tetrachloride stirred in an ice bath under an argon atmosphere is added rapidly 1.5 g of 2-bromoethyl phosphorodichloridate in 0.5 ml of carbon tetrachloride followed by the rapid addition of 0.95 ml of triethylamine. Stirring is continued at ambient temperature for 1.5 hours followed by storing in a refrigerator for 18 hours. The reaction mixture is filtered through diatomaceous earth and the cake washed with toluene. The combined filtrates are evaporated to a residue which is stirred with 110 ml of 0.5M sodium acetate and 110 ml of tetrahydrofuran for 1.5 hours. The tetrahydrofuran is evaporated and the aqueous residue acidified with 10% hydrochloric acid and extracted with ether. The ether is washed with brine, dried, then evaporated to a wax residue which is dissolved in 90 ml of chloroform and 100 ml of a solution of 50 g of trimethylamine in 100 ml of acetonitrile added. The mixture is stirred at reflux for 4 hours. The solvents are evaporated and the residue dissolved in 50 ml of chloroform and 50 ml of methyl alcohol containing 5 ml of water and 673 mg of silver carbonate then stirred at ambient temperature for 2 hours. The mixture is filtered through diatomaceous earth, washing with 1:1 methyl alcohol:chloroform. The solvents are evaporated to a glass which is purified by chromatography on silica gel by eluting with 30% methyl alcohol:chloroform followed by 65:35:6 chloroform:methyl alcohol:water. Fractions are combined and evaporated to a residue which is stirred with ether and filtered to give 0.74 g of the less polar isomer product as an amorphous solid. Further elution of the column with the same solvent mixture followed by evaporation of product fractions to a residue which is stirred with ether and filtered to give 0.87 g of the more polar isomer product as a white solid. The more polar isomer product (0.74 g) is purified by chromatography on silica gel with 30% methyl alcohol:chloroform followed by 65:35:6 chloroform:methyl alcohol:water. Fractions containing product are combined and evaporated to a residue which was stirred with ether and filtered to give 0.58 g of the desired product as a white amorphous solid.$[\alpha]_D^{26}=4.5°\pm0.3$.

EXAMPLE 98

3,5,8,10-Tetraoxa-4,9-diphosphahexacosan-1-aminium, (7R)-,7-[(hexadecyloxy)methyl]-4-hydroxy 9 methoxy-N,N,N-trimethyl-, hydroxide, inner salt, 4,9-dioxide, less polar diastereomer To a stirred solution of 3.6 g of phosphoric acid, (1S)-hexadecyl 2-(hexadecyloxy)-1-(hydroxymethyl-)ethyl methyl ester, less polar diastereomer in 50 ml of dry carbon tetrachloride while cooling in an ice bath under inert gas is added 1.8 g of 2-bromoethyl phosphorodichloridate followed by the rapid dropwise addition of 1.1 ml of triethylamine. The cooling bath is removed and the reaction stirred at ambient temperature for 3 hours followed by storing in a refrigerator for 18 hours. The reaction mixture is filtered and the filter cake washed with toluene. The combined filtrates are evaporated and the residue stirred with 110 ml of 0.5M sodium acetate and 110 ml of tetrahydrofuran at ambient temperature for 1.5 hours. The tetrahydrofuran is removed and the aqueous residue acidified with dilute hydrochloric acid followed by ether extraction. The ether extract is washed with brine, dried and evaporated to give a waxy residue which is dissolved in 90 ml of chloroform to which 100 ml of a solution of 50 g of trimethylamine in 100 ml of dry acetonitrile is added. The mixture is refluxed by heating in a 70° C. bath for 4 hours. The volatiles are removed and the residue dissolved in 60 ml of chloroform, 60 ml of methyl alcohol and 6 ml of water to which 782 mg of silver carbonate is added followed by stirring at ambient temperature for 2 hours. The mixture is filtered through diatomaceous earth and the cake washed with 1:1 methyl alcohol:chloroform. The combined filtrates are evaporated to a residue which is purified by chromatography on silica gel using 30% methyl alcohol:chloroform followed by 65:35:6 chloroform: methyl alcohol:water. Fractions containing the desired product are combined and evaporated to a residue which is stirred with ether and filtered to give 646 mg of less polar isomer product. Further elution followed by evaporation of solvents affords 896 mg of a residue $[\alpha]_D^{26}+3.2°\pm0.6$ c=1.55% in chloroform solvent. The less polar isomer product is further purified by chromatography on silica gel using 30% methyl alcohol:chloroform followed by 65:35:6 chloroform:methyl alcohol: water to give upon evaporation of solvents followed by additional evaporation with toluene and stirring the residue with ether, 480 mg of the less polar isomer produce as a white powder. $[\alpha]_D^{26}+4.7°\pm2$ c=4.235% in chloroform solvent.

EXAMPLE 99

3,5,9-Trioxa-4-phosphapentacosan-1-aminium, 7-[(bromoacetyl)oxy]-4-hydroxy-N,N,N-trimethyl-, hydroxide, inner salt, 4-oxide A mixture of 500 mg of 3,5,9-trioxa-4-phosphapentacosan-1-aminium, 4-hydroxy-N,N,N-trimethyl-, hydroxide, inner salt, 4-oxide, 86.2 mg of anhydrous sodium acetate and 1.35 g of bromoacetic anhydride in 25 ml of chloroform is stirred in an oil bath of 75° C. for 5 hours then allowed to cool over 18 hours. The chloroform is evaporated and the residue purified by chromatography on silica gel using 30% methyl alcohol:chloroform followed by chloroform:methyl alcohol:water to give 198 mg of the desired product as a glass.

EXAMPLE 100

Ethyl 2-[(hexadecyloxy]methyl]-2-propenoate

To a stirred solution of 1.9 g of hexadecanol in 40 ml of methylene chloride containing 700 mg of dimethylaminopyridine is added 500 mg of ethyl 2-bromomethyl-2-propenoate followed by continued stirring for 18 hours. The solvent is evaporated to give 2.4 g of the desired product.

EXAMPLE 101

Ethyl 3-(hexadecyloxy)-2-[(hexadecylthio)methyl]propanoate

To a stirred solution of 20 g of ethyl 2-[(hexadecyloxy)methyl]-2-propenoate in 60 ml of ethyl alcohol containing 10 ml of triethylamine is added 53 ml hexadecylmercaptan. Following stirring for 18 hours, the volatile components are removed and the residue is chromatographed by HPLC on silica gel using 9:1 hexanes:ethyl acetate. Fractions containing product are combined and the solvents evaporated to give 32.9 g of the desired product as a white waxy solid.

EXAMPLE 102

3-(Hexadecyloxy)-2-(hexadecylthio)methyl-1-propanol

To a slurry of 1.04 g of lithium borohydride in tetrahydrofuran at ambient temperature is added 29 g of ethyl 3-(hexadecyloxy)-2-[(hexadecylthio)methyl]-propanoate followed by heating at reflux for 18 hours. The mixture is poured into water containing a small amount of acid followed by extraction with ether to give after drying and evaporation, a residue which is columned on silica gel using 30:1 hexane:ethyl acetate. Fractions containing the product are evaporated to give 18.4 g of the desired product.

EXAMPLE 103

Phosphoric acid, 2-bromoethyl 3-(hexadecyloxy)-2-[(hexadecylthio)methyl]propyl ester A mixture of 15.0 g of 3-(hexadecyloxy)-2-[(hexadecylthio)methyl]-1-propanol, 9.6 g of phosphate and 5.7 ml of triethylamine in 100 ml of carbon tetrachloride is stirred at room temperature for 3 hours. Following filtration through diatomaceous earth, the solvents are evaporated and the residue stirred with 100 ml of 0.5M sodium acetate and 100 ml of tetrahydrofuran at ambient temperature for 18 hours. Dilute hydrochloric acid is added followed by extraction with ethyl acetate. The combined extracts are dried and evaporated to give 18.3 g of the desired product as a solid, m.p. 48°-50° C.

EXAMPLE 104

7-[(Hexadecylthio)methyl]-4-hydroxy-N,N,N-trimethyl-3,5,9-trioxa-4-phosphapentacosan-1-aminium, hydroxide, inner salt, 4-oxide A solution of 25.76 g of phosphoric acid, 2-bromoethyl]3-(hexadecyloxy)-2-[(hexadecylthio)methyl]propyl ester in 200 ml of acetonitrile, 150 ml of chloroform and 173 ml of trimethylamine is heated at 60° C. for 18 hours. The solvents are evaporated and the residue is stirred with 150 ml of methyl alcohol, 4.0 g of silver carbonate and 3.0 g of Amberlite ®IR-4B resin for 2 hours. The insolubles are filtered and the filtrate evaporated to a residue which is chromatographed on silica gel using 70:30 chloroform:methyl alcohol and 65:35:6 chloroform:methyl alcohol:water to give upon evaporation of fractions containing the product, a residue which is chromatographed on silica gel using high pressure liquid chromatography with 65:35:6 chloroform:methyl alcohol:water to give 8.5 g of the desired compound as a white solid.

EXAMPLE 105

Ethyl 2-[(hexadecyloxy)methyl]-2-propenoate

A solution of 400 mg of 1.1 g of hexadecanol and 550 mg of dimethylaminopyridine in 15 ml of methylene chloride is stirred at ambient temperature for 18 hours. The solvent is removed and the residue subjected to preparative thick layer chromatography using 25% ethyl acetate:petroleum ether to give 324 mg of the desired product as a gum.

EXAMPLE 106

2-[(Hexadecyloxy)methyl]-2-propen-1-ol

To a solution of 21 g of ethyl 2-[(hexadecyloxy)methyl]-2-propenoate in 400 ml of ether cooled to 0° C. under an inert atmosphere is added 2.25 ml of 1,2M DIBAL in hexanes over 30 minutes. The reaction is stirred at ambient temperature for 2 hours then cooled to 0° C. while 20 ml of saturated sodium sulfate is added dropwise. After filtering, the cake is washed with ether. The combined ether washings are dried and the solvent removed. The residue is crystallized from methyl alcohol:water to give 25.8 g of the desired product as a colorless solid.

EXAMPLE 107

Ethaniminium, 2-[[hydroxy[(2-methylenenonadecyl)oxy]phosphinyl]oxy]-N,N,N-trimethyl-, hydroxide, inner salt To a solution of 3.8 g of 2-[(hexadecyloxy)methyl]-2-propen-1-ol in 100 ml of carbon tetrachloride is added 3.91 g of 2-bromoethyl phosphorodichloridate and 1.64 g of triethylamine followed by storing in a refrigerator for 18 hours. The reaction mixture is filtered and the solvent removed. The residue is stirred with 100 ml of 0.5M sodium acetate and 100 ml of tetrahydrofuran for 1 hour. The tetrahydrofuran is removed and the residue acidified with dilute sulfuric acid followed by ether extraction. The organic layer is washed with brine and dried. The solvent is removed and the residue stirred at reflux in 60 ml of acetonitrile, 50 ml of chloroform and 20 ml of trimethylamine for 4 hours. The solvent is removed and the residue stirred with 100 ml of methyl alcohol, 10 g of Amberlite ® IR-4B resin and 1 g of silver carbonate then filtered. The solvent is evaporated and the residue chromatographed on silica gel eluting with 7:3 chloroform:methyl alcohol and then with 70:30:1 chloroform:methyl alcohol:water. The volatiles are removed and the fractions containing the desired product triturated with ether and filtered to give 2.4 g of the desired product as a white solid.

EXAMPLE 108

3,5,9-Trioxa-4-phosphapentacosan-1-aminium, 7-(boronomethyl)-4-hydroxy-N,N,N-trimethyl-, hydroxide, inner salt, 4-oxide To a stirred solution of 9 ml of 0.98M Borane in tetrahydrofuran at 0° C. under inert gas is added dropwise over 20 minutes a solution of 2.4 g of ethaniminium, 2-[[hydroxy[(2-methylenenonadecyl)oxy]phosphinyl]oxy]-N,N,N-trimethyl-, hydroxide, inner salt in 75 ml of methylene chloride. Stirring is continued for 1.5 hours. The volatiles are removed and methyl alcohol added to the residue. The methyl alcohol is removed by evaporation and the concentrate chromatographed on silica gel with 7:3 chloroform:methyl alcohol followed by 70:30:3.5 chloroform:methyl alcohol:water to give 0.72 g of the desired product as a white powder from ether trituration.

EXAMPLE 109

[2-(Hexadecyloxy)-1-(hydroxymethyl)-ethoxy]acetic acid

To a stirred slurry of 13.07 g of hexane washed sodium hydride in 200 ml of toluene is added dropwise a solution of 12.61 g of chloroacetic acid in 50 ml of toluene under an inert gas over 45 minutes. A solution of 65.5 g of 1-[(4-methoxyphenoxy)diphenylmethoxy]-3-hexadecyloxy-2-propanol in 100 ml of toluene is added dropwise over 30 minutes followed by reflux for 65 hours. The pH is adjusted to 4 with dilute hydrochloric acid and the mixture extracted with ether. The organic layer is washed with brine, dried and the solvent removed. The residue is stirred for 1 hour with 450 ml of methyl alcohol, 100 ml of chloroform and 20 g of Amberlite ® IR-4B resin. The solvents are evaporated and the residue chromatographed on silica gel by high pressure liquid chromatography using 4:1 hexane:ethyl acetate. Fractions containing product are evaporated to give 22.39 g of the desired product as a white solid.

EXAMPLE 110

2,5,7-Trioxa-6-phosphanonan-9-aminium, 1-carboxy-3-[(hexadecyloxy)methyl]-6-hydroxy-N,N,N-trimethyl-, hydroxide, inner salt, 6-oxide To a stirred solution of 22.39 g of [2-(hexadecyloxy)-1-(hydroxymethyl)-ethoxy]acetic acid in 150 ml of carbon tetrachloride is added 6.48 g of triethylamine and 11.62 g of 2-bromoethyl phosphorodichloridate. The mixture is stirred for 1.5 hours and filtered. The solvent is removed and the residue was stirred for 2 hours with 300 ml of 0.5M sodium acetate and 300 ml of tetrahydrofuran followed by acidification with hydrochloric acid and ether extraction. The ether extract is dried and evaporated to a residue which is refluxed with 250 ml of acetonitrile, 180 ml of chloroform, 80 g of trimethylamine and 20 g of Amberlite ® IR-4B resin for 4 hours. The solvent is removed and the residue chromatographed on silica gel with 9:1 chloroform:methyl alcohol followed by 70:30:3 chloroform:methyl alcohol:water to give 9.07 g of the desired product as a white solid after stirring the fraction concentrates with ether and filtering.

EXAMPLE 111

Ethyl 3-(hexadecylthio)propanoate

A solution of 15 g of hexadecylmercaptan, 3.0 g of ethyl acrylate and 2 ml of triethylamine is stirred at ambient temperature for 18 hours. The solvent is evaporated and the concentrate purified by high pressure liquid chromatography, to give 19.8 g of the desired product.

EXAMPLE 112

3-(Hexadecylthio)-1-propanol

To a slurry of 147 mg of lithium borohydride in 20 ml of tetrahydrofuran is added slowly with stirring 2.4 g of ethyl 3-(hexadecylthio)propanoate. The mixture is refluxed for 18 hours and poured into water. A few drops of hydrochloric acid is added followed by ether extraction. The organic layer is dried and evaporated to give 2.1 g of the desired product.

EXAMPLE 113

Phosphoric acid, 2-bromoethyl 3-(hexadecylthio) propyl ester

A mixture of 2.0 g of 3-(hexadecylthio)-1-propanol, 2.7 g of 2-bromoethyl phosphorodichloridate and 1.6 ml of triethylamine in 25 ml of carbon tetrachloride is stirred at room temperature for 3 hours. Following filtration through diatomaceous earth the solvents are evaporated and the residue stirred with 25 ml of 0.5M sodium acetate and 25 ml of tetrahydrofuran at ambient temperature for 18 hours. Dilute hydrochloric acid is added followed by extraction with ethyl acetate. The combined extracts are dried and evaporated to give 3.0 g of the desired product as a solid, m.p. 46°–49° C.

EXAMPLE 114

3,5-Dioxa-9-thia-4-phosphapentacosan-1-aminium, 4-hydroxy-N,N,N-trimethyl-, hydroxide, inner salt, 4-oxide A solution of 3.0 g of phosphoric acid, 2-bromoethyl 3-(hexadecylthio)propyl ester in 36 ml of acetonitrile and 33 ml of chloroform containing 31.4 ml of triethylamine is heated at 60° C. for 18 hours. The solvents are evaporated and residue is stirred with 1.0 g of silver carbonate and 1.0 g of Amberlite ®IR-4B in 35 ml of methyl alcohol for 2 hours. The insolubles are filtered and the filtrate evaporated to a residue which is chromatographed on silica gel using 70:30 chloroform:methyl alcohol and 65:35:6 chloroform:methyl alcohol:water to give upon evaporation of volatiles 1.5 g of the desired product as a white solid.

EXAMPLE 115

Ethyl 2-oxo-octadecanoate

A slurry of 40 ml of hexadecyl bromide in 250 ml of tetrahydrofuran containing 3.64 g of magnesium chips is put in a sonic bath. This solution is added dropwise to a stirred solution of 35.3 ml of diethyloxalate in 70 ml of tetrahydrofuran at −15° C. over 1 hour. The reaction mixture is poured into 3N hydrochloric acid and extracted with methylene chloride. The extract is dried and evaporated. The concentrate is purified by chromatography on silica gel using 5% ethyl acetate:petroleum ether. Fractions containing product are combined and evaporated. The residue is crystallized from petroleum ether to give 21.9 g of the desired product as a solid.

EXAMPLE 116

Ethyl 2,2-difluorooctadecanoate

To a solution of 14.2 g of ethyl 2-oxo-octadecanoate in 100 ml of methylene chloride at 0° C. is added 20 g of diethylamino sulfur trifluoride followed by stirring at ambient temperature for 72 hours. The mixture is partitioned between H₂O and hexane. The hexane layer is dried and evaporated to an oil which is purified by chromatography on silica gel using 0–25α ethylacetate in hexanes to give 6.9 g impure product and 7.9 g pure product as a waxy solid.

EXAMPLE 117

3.3-Difluoro-2-methyl-2-nonadecanol

To a solution of 6.9 g of ethyl 2,2-difluorooctadecanoate in 100 ml of ether at 0° C. is added 33 ml of methyl magnesium bromide dropwise with stirring. Following complete addition the reaction is allowed to reach room temperature and stirred for 30 minutes. The reaction mixture is washed with saturated ammonium chloride solution. The organic layer is washed with 10% hydrochloric acid, water and 10% sodium bicarbonate. The organic layer is dried and evaporated to an oil which is purified by chromatography on silica gel using 1-10% ethyl acetate:hexanes to give 3.8 g of the desired product as a solid following petroleum ether crystallization.

EXAMPLE 118

3 3-Difluoro-2-methyl-1-nonadecene

A solution of 160 mg of 3,3-difluoro-2-methyl-2-nonadecanol in 2 ml of pyridine containing 50 μl of phosphorous oxychloride is heated at 90° C. then allowed to cool to 50° C. An additional 250 μl of phosphorous oxychloride is added followed by heating at 90° C. for 2 hours. After allowing to stand at ambient temperature for 18 hours, the volatiles are removed and the concentrate partitioned between hexanes and 10% hydrochloric acid, The organic layer is washed with water and 10% sodium bicarbonate then dried and evaporated to a residue which is purified by chromatography on silica gel using hexane to give 140 mg of the desired product as an oil.

EXAMPLE 119

2-(Bromomethyl)-3.3-difluoro-1-nonadecene

A slurry of 140 mg of 3,3-difluoro-2-methyl-1-nonadecene in 2 ml of carbon tetrachloride containing 43 mg of N-bromosuccinimide and a catalytic amount of azobisisobutryonitrile is stirred at ambient temperature for 30 minutes. The mixture is filtered through a short pad of silica gel which is repeatedly washed with hexane. The combined filtrates are evaporated and the residue is purified on silica gel using hexanes to give 38 mg of the desired product as an oil.

EXAMPLE 120

Ethyl (3,3-difluoro-2-methylenenonadecyl)propanoate

To a slurry of 780 mg of hexane washed sodium hydride in 25 ml of tetrahydrofuran at 0° C. is added dropwise 2.2 ml of diethylmalonate. The cooling bath is removed and the reaction allowed to reach ambient temperature. A solution of 1.9 g of 2-(bromomethyl)-

3,3-difluoro-1-nonadecene in 10 ml of tetrahydrofuran is added dropwise over 30 minutes followed by stirring for an additional 30 minutes. Ether is added and the reaction washed with 10% hydrochloric acid, water and brine. The organic layer is dried and evaporated to a gum which is columned on silica gel using 2% ethyl acetate:petroleum ether to give 1.53 g of the desired product.

EXAMPLE 121

2-(3,3-Difluoro-2-methylenenonadecyl)-1,3-propanediol

To a slurry of 250 mg of lithium aluminum hydride in 10 ml of ether, cooled to 0° C. is added dropwise a solution of 1.48 g of ethyl (3,3-difluoro-2-methylenenonadecyl)propanoate in 10 ml of ether followed by warming to ambient temperature, heating at reflux for 3 hours, then allowing to cool to ambient temperature. The reaction mixture is washed with dilute hydrochloric acid, water and dilute sodium bicarbonate, dried and evaporated to a gum which is purified on silica gel using 40–60% ethyl acetate:hexanes. The fractions containing product are collected, evaporated and the residue crystallized from hexane giving 1.04 g of the desired product.

EXAMPLE 122

5 5,5-difluoro-2-(hexadecyloxy)methyl]-4-methylene-1-heneicosanol

To a slurry of 126 mg of hexane washed sodium hydride in 15 ml of N,N-dimethylformamide is added 990 mg of 2-(3,3-difluoro-2-methylenenonadecyl)-1,3propanediol with stirring. A 0.96 ml portion of hexadecylbromide is added followed by heating at 80° C. for 2 hours, then cooled over an hour. Ammonium chloride is added followed by evaporation of the solvent. The concentrate is dissolved in ether and washed with 10% hydrochloric acid, water and brine. The organic layer is dried and evaporated to a gum which is purified on silica gel using 1–100% ethyl acetate:hexanes to give 1.14 g of the desired product as a gum.

EXAMPLE 123

3,5,9-Trioxa-4-phosphapentacosan-1-aminium, 7-(3,3-difluoro-2-methylenenonadecyl)-4-hydroxy-N,N,N-trimethyl-, hydroxide, inner salt, 4-oxide A solution of 1.10 g of 5,5-difluoro-2-[(hexadecyloxy)methyl]-4-methylene-1-heneicosanol in 15 ml of carbon tetrachloride, containing 0.42 ml of triethylamine and 0.37 ml of 2-bromoethyl phosphorodichloridate is stirred at ambient temperature for 3 hours. The solvent is evaporated and the residue is stirred for 18 hours at ambient temperature with 25 ml of tetrahydrofuran and 25 ml of 0.5M sodium acetate. The tetrahydrofuran is evaporated, ether added followed by washing with 10% hydrochloric acid and water. The organic layer is dried and evaporated to a gum. Added 15 ml of chloroform and 40 ml of a solution of 50 g of trimethylamine in 100 ml of acetonitrile followed by heating at 60° C. for 3 hours. Evaporated the volatiles and purified the concentrate on silica gel using 3:7 methyl alcohol:chloroform followed by 5% water in 3:7 methyl alcohol:chloroform. Volatiles are removed and the concentrate evaporated with toluene and dried to give 1.0 g of the desired product as a gum.

EXAMPLE 124

3,5,9-Trioxa-4-phosphapentacosan-1-aminium, 7-(3,3-difluoro-2-oxononadecyl)-4-hydroxy-N,N,N-trimethyl-, hydroxide, inner salt, 4-oxide A solution of 500 mg of 3,5,9-trioxa-4-phosphapentacosan-1-aminium, 7-(3,3-difluoro-2-methylenenonadecyl)-4-hydroxy-N,N,N-trimethyl-, hydroxide, inner salt, 4-oxide in 20 ml of chloroform and 2 ml of ethyl alcohol is cooled at −40° C., treated with ozone until blue and flushed with oxygen. To the mixture is added 0.16 ml of trimethyl phosphite followed by evaporation. The concentrate is chromatographed on silica gel using 3:7 methyl alcohol:-chloroform followed by 5% water in 3:7 methyl alcohol:chloroform. Volatiles are removed to give 470 mg of the desired product.

EXAMPLE 125

3,5,9-Trioxa-4-phosphapentacosan-1-aminium, 7-(3,3-difluoro-2-hydroxynonadecyl)-4-hydroxy-N,N,N-trimethyl-, hydroxide, inner salt, 4-oxide To a stirred 0° C. solution of 200 mg of 3,5,9-trioxa-4-phosphapentacosan-1-aminium, 7-(3,3-difluoro-2-oxononadecyl)-4-hydroxy-N,N,N-trimethyl-, hydroxide, inner salt, 4-oxide in 3.5 ml of chloroform is added dropwise 1.0 ml of 1.0M borane-tetrahydrofuran complex followed by allowing to warm to ambient temperature over 1 hour. The volatiles are removed, methyl alcohol added and evaporated three times. The concentrate is chromatographed on silica gel with 3:7 methyl alcohol:chloroform followed by 5% water in 3:7 methyl alcohol:chloroform. Volatiles are removed to give 194 mg of the desired product.

EXAMPLE 126

(S)-4-[(Hexadecyloxy)methyl]-2,2-dimethyl-1,3-dioxolane

To a stirred mixture 3.38 g of hexane washed sodium hydride in 67 ml of dry toluene, under argon, is added dropwise 10.18 g of 1,2-0-isopropylidene-sn-glycerol in 17 ml of toluene. After 15 minutes, a solution of 25.7 g of hexadecylbromide in 17 ml of toluene is added dropwise over 20 minutes. The mixture is refluxed for 1.5 hours then stirred at ambient temperature for 18 hours. Ice is added followed by ice water. The organic layer was separated, washed with water, brine and dried. The solvent is removed to give 28 g of the desired product as a pale yellow oil.

EXAMPLE 127

(R)-3-[hexadecyloxy)-1,2-propanediol

A stirred mixture of 28 g of (S)-4-[(hexadecyloxy)methyl]-2,2-dimethyl-1,3-dioxolane in 190 ml of methyl alcohol and 21 ml of 1N hydrochloric acid is refluxed for 2 hours followed by cooling in an ice bath. The resulting solid is filtered and washed with cold acetone. The solid is crystallized from acetone to give 18.2 g of crystals which liquified at ambient temperature. The resulting oil is purified by chromatography on silica gel using 1:1 ethyl acetate:hexanes. Fractions containing product are combined and evaporated to a material which is stirred with acetone at −20° C. to give 4.1 g of crystalline solid, m.p. 65°–66° C.

EXAMPLE 128

(S)-1-(hexadecyloxy)-3-[(4-methoxyphenyl) diphenylmethoxy]-2-propanol

To a solution of 4.1 g of (R)-3-(hexadecyloxy)-1,2-propanediol in 15 ml of dry pyridine is added dropwise with stirring under inert gas a solution of 5.6 g of p-methoxytrityl chloride in 15 ml of tetrahydrofuran. Stirring is continued for 1.5 hours at ambient temperature then the reaction is stored in the refrigerator overnight. The reaction mixture is filtered and the cake washed with ether. The filtrate is evaporated to an oily residue which is dissolved in chloroform and washed with 10% sodium bicarbonate, water and then dried to give a stiff oil following evaporation of the solvent. The oil is purified by high pressure liquid chromatography on silica gel using 1:9 ethyl acetate:hexanes to give 7.6 g of the desired product as an oil.

EXAMPLE 129

Phosphoric acid, hexadecyl 2-(hexadecyloxy)-1-[[(4-methoxyphenyl)diphenylmethoxy]1methyl]ethyl methyl ester To a water bath cooled and stirred solution of 7.5 g of (S)-1-(hexadecyloxy)-3-[(4-methoxyphenyl)diphenylmethoxy]-2-propanol in 30 ml of carbon tetrachloride is added, with stirring under inert gas, 1.07 g of 4-dimethylaminopyridine and 7.63 ml of triethylamine. A solution of 11.75 g of phosphorodichloridic acid, hexadecyl ester in 5 ml of carbon tetrachloride is added at a rapid rate followed by washing the addition funnel with 5 ml of carbon tetrachloride. The reaction is stirred at ambient temperature for 3 days. Added 9.1 ml of triethylamine to the reaction mixture and continued stirring for 2 hours. A 965 ml solution of sodium bicarbonate (1 g/10 ml) is added to the reaction followed by three chloroform extractions. The combined extracts are dried and evaporated to give a dark oil which is purified by high pressure liquid chromatography on silica gel using 1:7 ethyl acetate:hexanes. Fractions containing product are combined to give 8.2 g of the desired compound.

EXAMPLE 130

Phosphoric acid, hexadecyl 2-(hexadecyloxy)-1-(hydroxymethyl)ethyl methyl ester, (1R)-, upper diastereomer Phosphoric acid, hexadecyl 2-(hexadecyloxy)-1-(hydroxymethyl-1ethyl methyl ester. (1R)- lower diastereomer To a solution of 8.2 g of phosphoric acid, (S)-hexadecyl 2-(hexadecyloxy)-1-[[(4-methoxyphenyl) diphenylmethoxy]methyl]ethyl methyl ester in 60 ml of methyl alcohol and 30 ml of chloroform, brought to a boil, is added 4,9 g of Amberlist ®-15 resin. The reaction is allowed to cool to ambient temperature while stirring over 90 minutes. The insolubles are filtered and the cake washed with 2:1 methyl alcohol:chloroform. The combined filtrates are evaporated and the residue dissolved in chloroform, washed with dilute sodium bicarbonate and dried. The volatiles are removed to give a yellow wax. The residue is purified by chromatography on silica gel using 1:1 ethyl acetate:hexane, giving two major products. The upper fractions are combined to give 2.31 g of phosphoric acid, hexadecyl 2-(hexadecyloxy)-1-(hydroxy-methyl)ethyl methyl ester, (1R)-, upper diasteromer of the desired product. The lower fractions are combined to give 2.06 g phosphoric acid, hexadecyl 2-(hexadecyloxy)-1-(hydroxymethyl-)ethyl methyl ester, (1R)-, lower diastereomer, of the desired product.

EXAMPLE 131

3,5,8,10-Tetraoxa-4 9-diphosphahexacosan-1-aminium, 7-[(hexadecyloxy)methyl]-4-hydroxy-9-methoxy-N,N,N-trimethyl-, hydroxide, inner salt, 4,9-oxide, (7S)-, lower diastereomer To a solution of 2.06 g of phosphoric acid, hexadecyl 2-(hexadecyloxy)-1-(hydroxy-methyl)ethyl methyl ester, (1R)-, lower diastereomer in 35 ml of carbon tetrachloride stirred in an ice bath under argon is added 1.02 g of 2-bromoethyl phosphorodichloridate in 2 ml of carbon tetrachloride followed by the rapid addition of 0.63 ml of triethylamine. The cooling bath is removed followed by stirring at ambient temperature for 2 hours. The reaction is stored in the refrigerator overnight, followed by filtering through diatomaceous earth. The filter cake is washed well with toluene and the combined filtrates evaporated to a residue which is stirred at ambient temperature with 80 ml of 0.5N sodium acetate and 80 ml of tetrahydrofuran for 2 hours. Evaporated the tetrahydrofuran and acidified the aqueous residue with hydrochloric acid then extracted with ether several times. The combined extracts are washed with brine, dried and the solvent evaporated. The residue is evaporated with toluene several times then dried under vacuum. The residue is dissolved in 75 ml of chloroform and 50 ml of a solution of 50 g of trimethylamine in 100 ml of acetonitrile added followed by heating at 65° C. for 4 acetonitrile added followed by heating at 65° C. for 4 hours. The solvents are removed and the residue dissolved in 38 ml of chloroform and 38 ml of methyl alcohol followed by adding 447 mg of silver carbonate. The reaction mixture is stirred at ambient temperature for 1.5 hours then filtered through diatomaceous earth. The cake is washed with 1:1 chloroform:methyl alcohol. The combined filtrates are evaporated and the residue purified by chromatography on silica gel using 30% methyl alcohol:chloroform and 65:35:6 chloroform:methyl alcohol:water. Product fractions are combined and evaporated to a residue which is stirred with ether and the resulting solid collected by filtration to give 420 mg of the desired product as a white amorphous powder.

EXAMPLE 132

3,5,8,10-Tetraoxa-4,9-diphosphahexacosan-1-aminium, 7-(hexadecyloxy)methyl]-4-hydroxy-9-methoxy-N,N,N-trimethyl-, hydroxide, inner salt, 4,9-dioxide, (7S)-, upper diastereomer A solution of 2.7 g of phosphoric acid, (1R)-hexadecyl 2-(hexadecyloxy)-1-(hydroxymethyl)ethyl methyl ester, upper diastereomer in 38 ml of chloroform, 38 ml of methanol and 3.8 ml of water is stirred with 502 mg of silver carbonate for 1.5 hours at ambient temperature. The mixture is filtered through diatomaceous earth and the cake washed with 1:1 chloroform:methyl alcohol. The combined filtrates are evaporated and the residue purified by chromatography on silica gel using 30% methyl alcohol:chloroform and 65:35:6 chloroform:methyl alcohol:water. The concentrate of product fractions is stirred with ether and the resulting solid collected by filtration to give 394 mg of the desired product as a white amorphous chloroform:methyl alcohol:water. The concentrate of product fractions is stirred with ether and the resulting solid collected by filtration to give 716 mg of the desired product as a white amorphous solid.

We claim:

1. A compound, including the individual R and S enantiomer and the racemic mixture, represented by the formula:

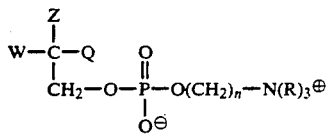

wherein:

A) n is an integer from 2 to 6;
B) R is selected from the group consisting of $C_1$-$C_4$ alkyl; and
C) Q is

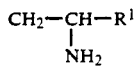

and W is hydrogen or hydroxyl, Z is $CH_2$—OX wherein $R^1$ and X are selected from the group consisting of $C_1$-$C_{24}$ alkyl.

2. A compound, including the individual R and S enantiomer and the racemic mixture, represented by the formula:

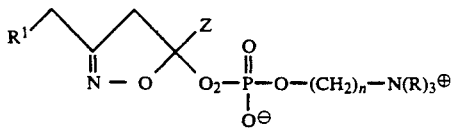

wherein:

A) n is an integer from 2 to 6;
B) R is selected from the group consisting of $C_1$-$C_4$ alkyl; and
C) Z is —$CH_2$—O—X wherein $R^1$ and X are selected from the group consisting of $C_1$-$C_{24}$ alkyl.

3. A pharmaceutical composition of matter in unit dosage form comprising an amount of a compound according to claim 1 effective to inhibit the biological effects of phospohlipase $A_2$ or the mediators produced as a result of its activity in association with a pharmaceutically acceptable carrier.

4. A pharmaceutical composition of matter in unit dosage form comprising an amount of a compound according to claim 2 effective to inhibit the biological effects of phospohlipase $A_2$ or the mediators produced as a result of its activity in association with a pharmaceutically acceptable carrier.

5. A method for inhibiting the biological effects of phospholipase $A_2$ or the mediators produced as a result of its activity which comprises administering to a mammal an effective amount of a compound according to claim 1.

6. A method for inhibiting the biological effects of phospholipase $A_2$ or the mediators produced as a result of its activity which comprises administering to a mammal an effective amount of a compound according to claim 2.

* * * * *